(12) United States Patent
Haeusser et al.

(10) Patent No.: US 11,484,239 B2
(45) Date of Patent: *Nov. 1, 2022

(54) SYSTEMS, DEVICES, COMPONENTS AND METHODS FOR DETECTING THE LOCATIONS OF SOURCES OF CARDIAC RHYTHM DISORDERS IN A PATIENT'S HEART

(71) Applicant: Ablacon Inc., Wheat Ridge, CO (US)

(72) Inventors: Philip Haeusser, Munich (DE); Peter Ruppersberg, Blonay (CH)

(73) Assignee: Ablacon Inc., Wheat Ridge, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/931,844

(22) Filed: Jul. 17, 2020

(65) Prior Publication Data

US 2020/0345261 A1 Nov. 5, 2020

Related U.S. Application Data

(63) Continuation-in-part of application No. 16/918,588, filed on Jul. 1, 2020, and a continuation-in-part of
(Continued)

(51) Int. Cl.
*A61B 5/318* (2021.01)
*A61B 5/316* (2021.01)
(Continued)

(52) U.S. Cl.
CPC ............ *A61B 5/316* (2021.01); *A61B 5/282* (2021.01); *A61B 5/287* (2021.01); *A61B 5/339* (2021.01);
(Continued)

(58) Field of Classification Search
CPC ........ A61B 5/367; A61B 5/341; A61B 5/7264
See application file for complete search history.

(56) References Cited

U.S. PATENT DOCUMENTS 9,808,171 B2 * 11/2017 Balachandran ........ A61B 5/061
10,143,374 B2 * 12/2018 Ruppersberg .......... A61B 5/287
(Continued)

FOREIGN PATENT DOCUMENTS

ES          2706537 B2    8/2020
WO    2019/063861 A1    4/2019

OTHER PUBLICATIONS

He et al, Video Target Tracking Based on Adaptive Kalman Filtering, Communications, Signal Processing, and Systems. CSPS 2019. Lecture Notes . . . , vol. 571, Springer, Singapore.
(Continued)

*Primary Examiner* — Eric D. Bertram
(74) *Attorney, Agent, or Firm* — Wooda Patent Law, P.C.

(57) ABSTRACT

Disclosed are various examples and embodiments of systems, devices, components and methods configured to detect a location of a source of at least one cardiac rhythm disorder in a patient's heart. In some embodiments, electrogram signals are acquired from a patient's body surface, and subsequently normalized, adjusted and/or filtered, followed by generating a two-dimensional spatial map, grid or representation of the electrode positions, processing the amplitude-adjusted and filtered electrogram signals to generate a plurality of three-dimensional electrogram surfaces corresponding at least partially to the 2D map, one surface being generated for each or selected discrete times, and processing the plurality of three-dimensional electrogram surfaces through time to generate a velocity vector or other type of map using one or more of optical flow, video tracking analysis, motion capture analysis, motion estimation analysis, data association and segmentation tracking analysis, particle tracking analysis, and single-particle tracking analysis methods corresponding at least partially to the 2D map. Trained atrial discriminative machine learning models that facilitate the foregoing systems and methods, and that pro-
(Continued)

vide predictions or results concerning a patient's condition, are also disclosed.

22 Claims, 45 Drawing Sheets
(30 of 45 Drawing Sheet(s) Filed in Color)

Related U.S. Application Data application No. 16/724,254, filed on Dec. 21, 2019, and a continuation-in-part of application No. 16/387,873, filed on Apr. 18, 2019, now Pat. No. 11,291,395, and a continuation-in-part of application No. 16/231,883, filed on Dec. 24, 2018, now Pat. No. 10,980,418, and a continuation-in-part of application No. 15/923,286, filed on Mar. 16, 2018, now Pat. No. 10,820,800, and a continuation-in-part of application No. 15/756,865, filed on Mar. 1, 2018, now Pat. No. 10,888,236, and a continuation-in-part of application No. 15/548,671, filed on Aug. 3, 2017, now Pat. No. 10,201,277, and a continuation-in-part of application No. 15/258,410, filed on Sep. 7, 2016, now Pat. No. 10,143,374.

(60) Provisional application No. 62/875,452, filed on Jul. 17, 2019.

(51) Int. Cl.
| | | |
|---|---|---|
| *A61B 5/00* | (2006.01) | |
| *A61B 5/282* | (2021.01) | |
| *A61B 5/287* | (2021.01) | |
| *A61B 5/339* | (2021.01) | |
| *A61B 5/341* | (2021.01) | |
| *A61B 5/361* | (2021.01) | |
| *A61B 5/367* | (2021.01) | |

(52) U.S. Cl.
CPC .............. *A61B 5/341* (2021.01); *A61B 5/361* (2021.01); *A61B 5/367* (2021.01); *A61B 5/7225* (2013.01); *A61B 5/7264* (2013.01); *A61B 5/7275* (2013.01)

(56) References Cited

U.S. PATENT DOCUMENTS

| | | | | |
|---|---|---|---|---|
| 10,201,277 | B2* | 2/2019 | Ruppersberg | A61B 5/742 |
| 10,806,343 | B2* | 10/2020 | Ruppersberg | A61B 18/1492 |
| 10,820,800 | B2* | 11/2020 | Ruppersberg | A61B 5/339 |
| 10,888,236 | B2* | 1/2021 | Ruppersberg | A61B 5/287 |
| 10,980,418 | B2* | 4/2021 | Ruppersberg | A61B 5/316 |
| 2015/0313491 | A1* | 11/2015 | Edwards | A61B 5/0036 |
| | | | | 600/374 |
| 2017/0027465 | A1* | 2/2017 | Blauer | A61B 5/6858 |
| 2017/0065198 | A1* | 3/2017 | Ruppersberg | A61B 5/316 |
| 2017/0178403 | A1* | 6/2017 | Krummen | G06T 17/20 |

OTHER PUBLICATIONS

Liu et al, 2018, Visual tracking in high-dimensional particle filter. PLOS One 13(8): e0201872.
Gall et al, Functional Categorization of Objects using Real-time Markerless Motion Capture, IEEE Conf. on Computer Vision and Pattern Recognition (CVPR''11), 1969-1976, 2011.
Zhu et al, "Real-Time Motion Capture: An Overview", Complex Intelligent and Software Intensive Systems (CISIS) 2016 10th International Conference on, pp. 522-525, 2016.
Strintzis et al, "Maximum likelihood motion estimation in ultrasound image sequences," in IEEE Signal Processing Letters, vol. 4, No. 6, pp. 156-157, Jun. 1997.
Golemati et al., "Ultrasound-Image-Based Cardiovascular Tissue Motion Estimation," in IEEE Reviews in Biomedical Engineering, vol. 9, pp. 208-218, 2016.
Lochmatter et al, "SwisTrack—A Flexible Open Source Tracking Software for Multi-Agent . . . ," 2008 IEEE/RSJ Int'l Conf. Intell. Robots and Systems, France 2008, pp. 4004-4010.
Correll et al, 2006, SwisTrack: A Tracking Tool for Multi-Unit Robotic and Biological Systems. IEEE International Conference on Intelligent Robots and Systems. 2185-2191.
Tinevez et al, 2016, TrackMate: An Open and Extensible Platform for Single-Particle Tracking. Methods. 115. 10.1016/j.ymeth.2016.09.016.
Smith et al, 2011, Interactive Computer-Assisted Tracking of Speckle Trajectories . . . Fusion, Biophysical journal. 101. 1794-804. 10.1016/j.bpj.2011.09.007.
Rios-Munoz et al., Real-time Rotational Activity Detection in Atrial Fibrillation. Front Physiol. Mar. 13, 2018;9:208 (1-17).
Rios-Munoz, Rotor Detection in Atrial Fibrillation. Doctoral Thesis. Universidad Cados III de Madrid. Jun. 2018 159 pages.

\* cited by examiner

◯ = Rotor Location

Pilot Study: 24 Patients from Hamburg

Electrographic Flow (EGF) Analysis Defines Therapy

- A- and B-type patients profit from targeted ablations of stable atrial sources
- C-type patients are cured by PVI only and do not additionally profit from targeted source ablation
- This finding leads emphasizing extracorporeal methods to prescreen AF patients. A pre-classification would funnel the patients to either rapid PVI procedures (single shot devices) or alternatively to full scale basket catheter EGF guided procedures.

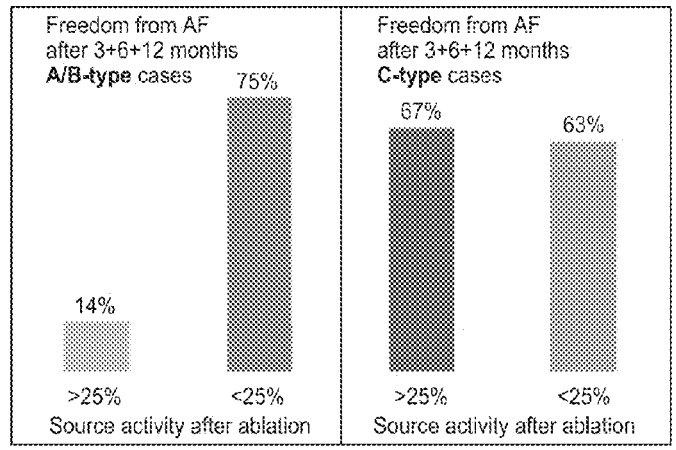

FIG. 11(g)

Example of Potential Distribution During the Sinus Rhythm P-Wave

| POS | patent # | resources |
|---|---|---|
| A | Pat19 | 39.00 |
| A | Pat23* | 24.80 |
| B | Pat10* | 18.10 |
| A | Pat22 | 16.70 |
| A | Pat16 | 14.90 |
| A | Pat24 | 12.20 |
| B | | |
| C | | |
| A | | |
| B | | |
| B | | |
| A | Pat18 | 11.20 |
| C | | |
| C | | |
| B | Pat21 | 10.00 |
| C | | |
| A | | |
| C | | |
| C | | |
| C | | |
| B | | |
| B | | |
| C | Pat04 | 6.20 |
| C | | |

Fig. 19

| Type | Patent | Indication |
|---|---|---|
| A | Pat23* | 93.00 |
| A | Pat16 | 64.40 |
| A | Pat18 | 55.50 |
| A | Pat14 | 50.40 |
| A | Pat19 | 49.30 |
| B | Pat10* | 32.20 |
| B | Pat21 | 29.20 |
| A | Pat22 | 28.50 |
| B | Pat05 | 22.70 |
| C | Pat03 | 22.40 |
| B | Pat01 | 21.90 |
| C | Pat04 | 21.80 |
| C | Pat09 | 20.70 |
| B | Pat08 | 20.60 |
| C | Pat06 | 20.10 |
| C | Pat07 | 19.00 |
| C | Pat12 | 18.70 |
| B | Pat13 | 18.60 |
| A | Pat02 | 18.00 |
| C | Pat15 | 17.70 |
| C | Pat11 | 17.60 |
| C | Pat17 | 17.00 |
| B | Pat20 | 16.80 |
| A | Pat24 | 9.10 |

Fig. 20

| Type | Activity | | Recurrence AF/AT after | |
|---|---|---|---|---|
| | Max | Final | 3 and 6 or | 12 months |
| A | BP19 | 93.50 | 93.50 | 1 | |
| A | Case83 | 79.90 | 79.90 | 1 | 1 |
| A | Case39 | 71.70 | 71.70 | 1 | 1 |
| A | BP03 | 81.50 | 67.20 | 1 | |
| B | | | | | |
| A | Case23 | 79.30 | 57.00 | 1 | 1 |
| A | Case47 | 54.90 | 54.90 | 1 | 1 |
| A | Case13 | 54.40 | 54.40 | 1 | 1 |
| A | | | | | |
| A | Case69 | 65.90 | 51.90 | 1 | 1 |
| A | Case50* | 50.80 | 50.80 | 1 | |
| B | Case87 | 50.30 | 50.30 | 1 | 1 |
| C | | | | | |
| B | Case40 | 60.20 | 45.90 | 1 | 1 |
| B | Case70 | 44.30 | 44.30 | 1 | 1 |
| A | Case36 | 41.90 | 41.90 | 1 | 1 |
| B | Case07 | 33.90 | 33.90 | 1 | |
| A | Case77 | 33.60 | 33.60 | 1 | 1 | 12 months |
| B | Case32 | 33.00 | 33.00 | 1 | 1 |
| A | Case67 | 46.20 | 30.70 | 1 | |
| C | | | | | |
| B | | | | | |
| B | Case18 | 30.20 | 30.20 | 1 | 1 |
| C | Case56 | 29.90 | 29.90 | 1 | |
| A | Case74 | 29.80 | 29.80 | 1 | |
| A | | | | | |
| B | Case17 | 29.30 | 29.20 | 1 | |
| B | Case84 | 28.50 | 28.50 | 1 | 1 |
| A | Case12 | 66.30 | 27.80 | 1 | |
| C | | | | | |
| A | Case99 | 32.20 | 27.90 | 1 | 1 |
| C | | | | | |
| C | Case24 | 26.60 | 26.60 | 2 | 1 |
| B | Case15 | 26.30 | 26.30 | 1 | 1 |
| B×C | Case52* | 25.90 | 25.90 | 1 | |
| B | Case89 | 25.00 | 25.00 | 1 | 1 |

SYSTEMS, DEVICES, COMPONENTS AND METHODS FOR DETECTING THE LOCATIONS OF SOURCES OF CARDIAC RHYTHM DISORDERS IN A PATIENT'S HEART

RELATED APPLICATIONS

This application is related to, and claims priority and other benefits from, U.S. Provisional Patent Application Ser. No. 62/875,452 entitled "Methods, Systems, Devices and Components for Detecting and/or Classifying Atrial Fibrillation in a Patient's Heart Using Non-invasive Body Surface Electrodes and Machine Learning Methods" to Haeusser et al. filed on Jul. 17, 2019 (hereafter "the 452 patent application").

This application is also a continuation-in-part of, and claims priority and other benefits from:

- U.S. patent application Ser. No. 15/258,410 to Ruppersberg filed on Sep. 7, 2016 (now U.S. Pat. No. 10,143, 374), which is entitled "Systems, Devices, Components and Methods for Detecting the Locations of Sources of Cardiac Rhythm Disorders in a Patient's Heart (hereafter "the '410 patent application").
- U.S. patent application Ser. No. 15/548,671 to Ruppersberg filed on Aug. 3, 2017 (now U.S. Pat. No. 10,201, 277), which is entitled "Systems, Devices, Components and Methods for Detecting the Locations of Sources of Cardiac Rhythm Disorders in a Patient's Heart" (hereafter "the '671 patent application");
- U.S. patent application Ser. No. 15/756,865 to Ruppersberg filed on Mar. 1, 2018 (now U.S. Pat. No. 10,888, 236), which is entitled "System for Analyzing Electrophysiological Data and Method for Analyzing Electrophysiological Data" (hereafter "the '865 patent application"),
- U.S. patent application Ser. No. 15/923,286 to Ruppersberg filed on Mar. 16, 2018 (now U.S. Pat. No. 10,820, 800), which is entitled "Systems, Devices, Components and Methods for Detecting the Locations of Sources of Cardiac Rhythm Disorders in a Patient's Heart and Classifying Same" (hereafter "the '286 patent application");
- U.S. Patent Application Ser. No. 16/231,883 to Ruppersberg filed on Dec. 24, 2018 (now U.S. Pat. No. 10,980, 418), which is entitled "Systems, Devices, Components and Methods for Detecting the Locations of Sources of Cardiac Rhythm Disorders in a Patient's Heart" (hereafter "the '883 patent application");
- U.S. patent application Ser. No. 16/387,873 to Ruppersberg filed on Apr. 18, 2019, which is entitled "Systems, Devices, Components and Methods for Detecting the Locations of Sources of Cardiac Rhythm Disorders in a Patient's Heart and Classifying Same" (hereafter "the '883 patent application");
- U.S. patent application Ser. No. 16/724,254 entitled "Systems, Devices, Components and Methods for Detecting the Locations of Sources of Cardiac Rhythm Disorders in a Patient's Heart" to Haeusser et al. filed on Dec. 21, 2019 (hereafter "the '254 patent application"), and U.S. patent application Ser. No. 16/918,588 entitled "Methods, Systems, Devices, and Components for Visualizing Electrographic Flow (EGF)" to Haeusser et al. filed on Dec. 21, 2019 (hereafter "the '588 patent application").

The respective entireties of each of the '452, '410, '671, '865, '286, '883, '873, '254, and '588 patent applications are hereby incorporated by reference herein.

FIELD OF THE INVENTION

Various embodiments described and disclosed herein relate to the field of medicine generally, and more particularly to diagnosing and treating cardiac rhythm disorders in a patient's heart using electrophysiological mapping, electrographic flow (EGF) and optical flow techniques, and other flow and tracking techniques, as well as in some embodiments using imaging, navigation, cardiac ablation and other types of medical systems, devices, components, and methods. Various embodiments described and disclosed herein also relate to systems, devices, components and methods for discovering with enhanced precision the location(s) of the source(s) of different types of cardiac rhythm disorders and irregularities in a patient's heart, such as, by way of example, active rotors, passive rotors, areas of fibrosis, breakthrough points and focus points.

BACKGROUND

Persistent atrial fibrillation (AF) is assumed to be caused by structural changes in atrial tissue, which can manifest themselves as multiwavelet re-entry and/or stable rotor mechanisms (see, e.g., De Groot M S et al., "Electropathological Substrate of Longstanding Persistent Atrial Fibrillation in Patients with Structural Heart Disease Epicardial Breakthrough," Circulation, 2010, 3: 1674-1682). Radio frequency (RF) ablation targeting such host drivers of AF is generally accepted as the best therapeutic approach. RF ablation success rates in treating AF cases are currently limited, however, by a lack of diagnostic tools that are capable of precisely determining the source (or type), and location, of such AF drivers. Better diagnostic tools would help reduce the frequency and extent of cardiac ablation procedures to the minimum amount required to treat AF, and would help balance the benefits of decreased fibrillatory burden against the morbidity of increased lesion load.

One method currently employed to localize AF drivers is the TOPERA® RhythmView® system, which employs a basket catheter having 64 electrodes arranged in an 8×8 pattern from which the system records unipolar electrograms or electrogram signals (EGMs). The RhythmView® algorithm creates a propagation map of the 64 electrodes through a phase analysis of EGM peaks after improving the signal to noise ratio through filtering and subtraction of a simulated compound ECG artifact. The RhythmView® algorithm detects where peak sequences between electrodes show a circular pattern candidate for a re-entry cycle and indicates those locations in a Focal Impulse and Rotor Map (FIRM) using A1 to H8 chess field coordinates for the electrodes. The resolution of the TOPERA system is limited by the spacing of the electrodes and consequently does not show the details of the AF drivers. In particular, the TOPERA system cannot show if a circular EGM wavefront is actively generated by a re-entry mechanism and is therefore is a driver of AF (i.e., an active rotor), or whether a circular EGM wavefront simply represents turbulence passively generated by an EGM wavefront hitting a barrier (i.e., a passive rotor). In addition, the TOPERA system does not show the direction of AF wavefront propagation, and does not provide the spatial or temporal resolution required to detect singularities associated with the generation of an active rotor.

A recent independent multicenter study ("OASIS, Impact of Rotor Ablation in Non-Paroxysmal AF Patients: Results from a Randomized Trial," Sanghamitra Mohanty, et al. and Andrea Natele, J Am Coll Cardiol. 2016) reported that the results obtained using TOPERA FIRM technology were inferior to those provided by non-specific ablation of the posterior wall of the left atrium. Moreover, the results suggested that FIRM based ablation is not sufficient for therapeutic success without pulmonary vein isolation (PVI) being performed in parallel. Although there are some questions about the methodology of this trial, many experts are convinced that the resolution and interpretability of the TOPERA system need to be improved.

In another approach to the problem, Toronto scientists recently presented a strategy to analyze EGM wave propagation using "Omnipolar Mapping," which seeks to measure beat-by-beat conduction velocity and direction (see, e.g., "Novel Strategy for Improved Substrate Mapping of the Atria: Omnipolar Catheter and Signal Processing Technology Assesses Electrogram Signals Along Physiologic and Anatomic Directions," D. Curtis Deno et al. and Kumaraswamy Nanthakumar; Circulation. 2015; 132:A19778). This approach starts with the time derivative of a unipolar EGM as measured by a set of electrodes having known distances to one other. Assuming constant velocity, the velocity and direction representing the best fit for a spatial derivative of the measured EGM are calculated and used to represent an estimate of the E field. According to a communication by Dr. Nanthakumar at the 2016 CardioStim Convention in Nice, France, however, this method remains incapable of dealing successfully with complex data sets, such as those obtained during an episode of AF.

AF is the most common supraventricular tachyarrhythmia worldwide and is associated with a significant health burden. Catheter ablation of pulmonary veins (PV) has been established as a therapeutic option for patients with symptomatic drug-refractory paroxysmal AF and results in high clinical success. However, the treatment of persistent and long-standing persistent AF is still challenging. A large number of patients present with recurrence of atrial tachyarrhythmia during mid- and long-term follow up. To achieve higher success rates, different ablation strategies have been reported, such as targeting additional AF sources. The initial results of focal impulse and rotor (FIRM) mapping for guiding catheter ablation of AF seemed to be promising. However, currently available systems for AF driver identification still have significant limitations, such as limited spatial resolution and difficulties in discriminating between active and passive rotors.

What is needed are improved means and methods of acquiring and processing intracardiac electrogram signals that reliably and accurately yield the precise locations and sources of cardiac rhythm disorders in a patient's heart. Doing so would enable cardiac ablation procedures to be carried out with greater locational precision, and would result in higher rates of success in treating cardiac rhythm disorders such as AF.

SUMMARY

Electrographical flow (EGF™) and other types of flow and tracking techniques and mapping represent novel and highly useful advances in atrial fibrillation detection and analysis technology. Flow and tracking mapping allows a full spatial and temporal reconstruction of electrographic potentials to be derived from endocardial unipolar electrogram data collected with a basket catheter. Flow and tracking mapping can also be used to reconstruct electrographic potentials, and in particular the locations of focal impulses and rotors, using body surface electrodes. Flow and tracking mapping allows AF drivers to be identified based on flow analysis, where sources of excitation occurring during AF can be characterized and monitored.

In one embodiment, there is provided a system configured to detect at least one location of at least one source of at least one cardiac rhythm disorder in a patient's heart, the system comprising at least one computing device; at least one data acquisition device operably connected to the at least one computing device or configured to provide as outputs therefrom at least one of intracardiac electrophysiological EP mapping signals (EP mapping signals) and body surface electrogram signals; a display or monitor operably connected to the at least one computing device and configured to visually display to the user one or more maps generated by the at least one computing device; wherein the computing device comprises at least one non-transitory computer readable medium configured to store instructions executable by at least one processor to determine the at least one location of the at least one source of the at least one cardiac rhythm disorder in the patient's heart, the computing device being configured to: (i) receive at least one of the intracardiac EP mapping signals and the body surface electrogram signals from at least one of a plurality of intracardiac electrodes located inside the patient's heart and a plurality of body surface electrodes located on the patient's body, where amplitudes of at least one of the intracardiac EP mapping signals and the body surface electrogram signals received by the at least one computing device have been at least one of conditioned, amplified, normalized, filtered, and adjusted by the data acquisition device before being provided to the computing device; (ii) assign or relate positional data corresponding to predetermined positions of at least one of the intracardiac electrodes in the patient's heart and the body surface electrodes on the patient's body to their respective corresponding: (1) intracardiac EP mapping signals and intracardiac electrodes, and (2) body surface electrogram signals and body surface electrodes; (iii) generate at least one spatial map of at least one of the intracardiac electrode positions and the body surface electrode positions; (iv) for each or selected discrete times over which at least one of the intracardiac EP mapping signals and the body surface electrogram signals are being processed, process at least one of the amplitude-adjusted intracardiac EP mapping signals and the amplitude-adjusted body surface electrogram signals to generate a plurality of electrogram surfaces or data grids, each such surface or data grid corresponding at least partially to the at least one spatial map, at least one surface or data grid being generated for each such time, and (v) using at least one of electrographic flow (EGF), video tracking analysis, motion capture analysis, motion estimation analysis, data association and segmentation tracking analysis, particle tracking analysis, and single-particle tracking analysis methods to process the plurality of electrogram surfaces or data grids through time to generate at least one map corresponding at least partially to the spatial map, the at least one map being configured to reveal the at least one location of the at least one source of the at least one cardiac rhythm disorder, the at least one map being shown to the user on the display or monitor.

Such an embodiment can further comprise one or more of: (a) the at least one processor and the at least one non-transitory computer readable medium being configured to determine, using a trained atrial discriminative machine learning model, predictions or results concerning atrial fibrillation in the patient's heart; (b) the trained atrial discriminative machine learning model having been trained at least partially using data obtained from a plurality of other previous patients, where intracardiac electrophysiological (EP) mapping signals for the other patients have been processed using one or more of electrographic flow (EGF), video tracking analysis, motion capture analysis, motion estimation analysis, data association and segmentation tracking analysis, particle tracking analysis, and single-particle tracking analysis methods to detect at least one of: (I) the presence of sources of atrial fibrillation in the other patients' hearts; (II) the locations of sources of atrial fibrillation in the other patients' hearts; (III) the activity levels of sources of atrial fibrillation in the other patients' hearts; (IV) the spatial variability levels of sources of atrial fibrillation in the other patients' hearts; (V) the flow angle stability levels of sources of atrial fibrillation in the other patients' hearts; and (VI) the classification of patients as at least one of types A, B and C; (c) paired data sets of body surface electrogram signals and the intracardiac EP mapping signals having been acquired simultaneously from at least some of the plurality of other patients and the paired data sets have been correlated to one another using the trained atrial discriminative machine learning model; (d) the trained atrial discriminative machine learning model being further configured to generate one or more of the following predictions or results for the patient using the conditioned electrogram signals and positional data corresponding to the patient: (1) Does the patient have atrial fibrillation or not? (2) If the patient has atrial fibrillation, determining at least one of the spatial variability level, the activity level, and the flow angle stability level associated with one or more sources detected in the patient's heart; (3) If the patient has atrial fibrillation, determining the locations of one or more sources detected in the patient's heart; (4) If the patient has atrial fibrillation, whether one or more activation sources detected in the patient's heart are characterized by chaotic flow; and (5) classification of the patient as one of types A, B and C; (e) the computing device being further configured to: (iv) process the conditioned electrogram data and positional data in the trained machine learning model to generate the one or more predictions or results; and (v) display the one or more predictions or results on the display or monitor to the user; (f) the plurality of electrogram surfaces being a plurality of three-dimensional electrogram surfaces that includes a first three-dimensional electrogram surface corresponding to a first EP mapping signal recording of a first duration of time and a second three-dimensional electrogram surface corresponding to a second EP mapping signal recording of a second duration of time, the second duration of time being greater than the first duration of time; (g) the first and second three-dimensional electrogram surfaces facilitating a determination of whether the patient's AF revealed in the map is characterized by one or more of: (a) atrial behavior exhibiting spatially and temporally stable rotors, drivers or sources (Type A); (b) atrial behavior where spatially stable rotors switch on and off (Type B), and (c) chaotic atrial behavior in which the rotors are spatially and temporally variable (Type C); (h) at least one of an activity value, a flow angle stability value, and a steadiness value being generated by the computing device for one or more sources corresponding to the at least one cardiac rhythm disorder revealed in the map; (i) at least one of the activity value, the flow angle stability value, and the steadiness value being displayed on the display or monitor; (j) on the basis of at least one of the generated activity values, flow angle stability values, and steadiness values the computing device determining whether to classify the patient as an A-type patient, a B-type patient, or a C-type patient; (k) the computing device being configured to determine whether the at least one map corresponds to an A-type patient, a B-type patient, or a C-type patient; (l) the electrogram surfaces or data grids comprising at least one three-dimensional surface; (l) the electrogram surfaces or data grids being generated by the computing device using Green's function; (m) the vector map generated by the computing device being configured to reveal a location in the patient's heart of one or more of: (a) an active rotor; (b) a passive rotor; (c) a breakthrough point, and (d) a focal point; (n) the EGF method being selected from the group consisting of a Horn-Schunck method, a Buxton-Buston method, a Black-Jepson method, a phase correlation method, a block-based method, a discrete optimization method, a Lucas-Kanade method, and a differential method of estimating optical flow.

In another embodiment, there is provided a method of detecting at least one location of at least one source of at least one cardiac rhythm disorder in a patient's heart using a system comprising at least one computing device, the computing device comprising at least one non-transitory computer readable medium configured to store instructions executable by at least one processor to determine the at least one location of the at least one source of the at least one cardiac rhythm disorder in the patient's heart, the system further comprising at least one of a plurality intracardiac electrodes and a plurality of body surface electrodes operably connected to the computing device through a data acquisition device and a monitor or screen operably connected to the computing device, the method comprising acquiring, using the data acquisition device, at least one of intracardiac electrophysiological mapping signals (EP mapping signals) and body surface electrogram signals using at least one of the intracardiac electrodes located within the patient's heart and the body surface electrodes located on one or more body surfaces of the patient; using at least one of the computing device and the data acquisition device, at least one of conditioning, filtering, normalizing and adjusting the amplitudes of at least one of the acquired EP mapping signals and the body surface electrogram signals; using the computing device, assigning positions or identifiers for each of at least one of the intracardiac electrodes and the body surface electrodes to corresponding to at least one of individual EP mapping signals and individual body surface electrogram signals; using the computing device and the assigned positions or identifiers, providing or generating a spatial map of at least one of the intracardiac electrode positions and the body surface electrode positions; using the computing device, for each or selected discrete times over which at least one of the EP mapping signals and the body surface electrogram signals are being processed, processing at least one of the amplitude-adjusted EP mapping signals and the amplitude-adjusted body surface electrogram signals to generate a plurality of electrogram surfaces or data grids corresponding at least partially to the spatial map, one surface or data grid being generated for each such time, and using the computing device, and using at least one of electrographic flow (EGF), video tracking analysis, motion capture analysis, motion estimation analysis, data association and segmentation tracking analysis, particle tracking analysis, and single-particle tracking analysis methods, processing the plurality of electrogram surfaces or data grids through time to generate a map corresponding at least partially to the spatial map, the map being configured to reveal on the monitor or display to a user the at least one location of the at least one source of the at least one cardiac rhythm disorder.

Such an embodiment can further comprise: (a) generating the electrograms surfaces or data grids using Green's function; (b) showing the at least one cardiac rhythm disorder as an active rotor, a passive rotor, a breakthrough point, or a focal point on the vector map; (c) the EGF method being selected from the group consisting of a Horn-Schunck method, a Buxton-Buston method, a Black-Jepson method, a phase correlation method, a block-based method, a discrete optimization method, a Lucas-Kanade method, and a differential method of estimating optical flow; (d) using a trained atrial discriminative machine learning model to provide predictions or results concerning atrial fibrillation in the patient's heart; (e) the trained atrial discriminative machine learning model having been trained at least partially using data obtained from a plurality of other previous patients, where intracardiac electrophysiological (EP) mapping signals for the other patients have been processed using at least of electrographic flow (EGF), video tracking analysis, motion capture analysis, motion estimation analysis, data association and segmentation tracking analysis, particle tracking analysis, and single-particle tracking analysis methods to detect at least one of: (I) the presence of sources of atrial fibrillation in the other patients' hearts; (II) the locations of sources of atrial fibrillation in the other patients' hearts; (III) the activity levels of sources of atrial fibrillation in the other patients' hearts; (IV) the spatial variability levels of sources of atrial fibrillation in the other patients' hearts; (V) the flow angle stability levels of sources of atrial fibrillation in the other patients' hearts; and (VI) the classification of patients as at least one of types A, B and C; (f) paired data sets of body surface electrogram signals and the intracardiac EP mapping signals having been acquired simultaneously from at least some of the plurality of other patients and the paired data sets have been correlated to one another using the trained atrial discriminative machine model; and (g) using the trained atrial discriminative machine learning model, generating one or more of the following predictions or results for the patient using the conditioned electrogram signals and positional data corresponding to the patient: (1) Does the patient have atrial fibrillation or not? (2) If the patient has atrial fibrillation, determining at least one of the spatial variability level, the activity level, and the flow angle stability level associated with one or more sources detected in the patient's heart; (3) If the patient has atrial fibrillation, determining the locations of one or more sources detected in the patient's heart; (4) If the patient has atrial fibrillation, whether one or more activation sources detected in the patient's heart are characterized by chaotic flow; and (5) classification of the patient as one of types A, B and C; (h)

Further embodiments are disclosed herein or will become apparent to those skilled in the art after having read and understood the claims, specification and drawings hereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Different aspects of the various embodiments will become apparent from the following specification, drawings and claims in which:

FIGS. 11(g) and 11(h) summarize EGF results and conclusions from EGF studies;

FIGS. 19 and 20 show data and statistics regarding a pilot study conducted in Hamburg, and FIGS. 21 and 22 show data and statistics corresponding to validation studies where FIRM data were ineffective and effective, respectively.

The drawings are not necessarily to scale. Like numbers refer to like parts or steps throughout the drawings.

DETAILED DESCRIPTIONS OF SOME EMBODIMENTS

Described herein are various embodiments of systems, devices, components and methods for diagnosing and treating cardiac rhythm disorders in a patient's heart using electrophysiological mapping or electrographic flow (EGF) techniques, as well as imaging, navigation, cardiac ablation and other types of medical systems, devices, components, and methods. Various embodiments described and disclosed herein also relate to systems, devices, components and methods for discovering with enhanced precision the location(s) of the source(s) of different types of cardiac rhythm disorders and irregularities. Such cardiac rhythm disorders and irregularities, include, but are not limited to, arrhythmias, atrial fibrillation (AF or A-fib), atrial tachycardia, atrial flutter, paroxysmal fibrillation, paroxysmal flutter, persistent fibrillation, ventricular fibrillation (V-fib), ventricular tachycardia, atrial tachycardia (A-tach), ventricular tachycardia (V-tach), supraventricular tachycardia (SVT), paroxysmal supraventricular tachycardia (PSVT), Wolff-Parkinson-White syndrome, bradycardia, sinus bradycardia, ectopic atrial bradycardia, junctional bradycardia, heart blocks, atrioventricular block, idioventricular rhythm, areas of fibrosis, breakthrough points, focus points, re-entry points, premature atrial contractions (PACs), premature ventricular contractions (PVCs), and other types of cardiac rhythm disorders and irregularities.

Various embodiments of optical flow (e.g., EGF), flow, and tracking techniques, methods, systems, devices, and components are described and disclosed herein, which involve the acquisition of intra-cardiac and/or body surface electrograms, and the subsequent processing and analysis of such electrograms to reveal the locations of sources of cardiac rhythm disorders in a patient's heart, such as rotors and sources that cause or contribute to AF. Some of the various techniques, methods, systems, devices, and components described and disclosed herein may be referred to collectively as pertaining to one or more of "EGF," "flow" and/or "tracking."

Systems and methods configured to detect in a patient's heart a location of a source of at least one cardiac rhythm disorder are disclosed herein. In the following description, for the purposes of explanation, numerous specific details are set forth in order to provide a thorough understanding of example embodiments or aspects. It will be evident, however, to one skilled in the art that an example embodiment may be practiced without necessarily using all of the disclosed specific details.

Figure 1A:
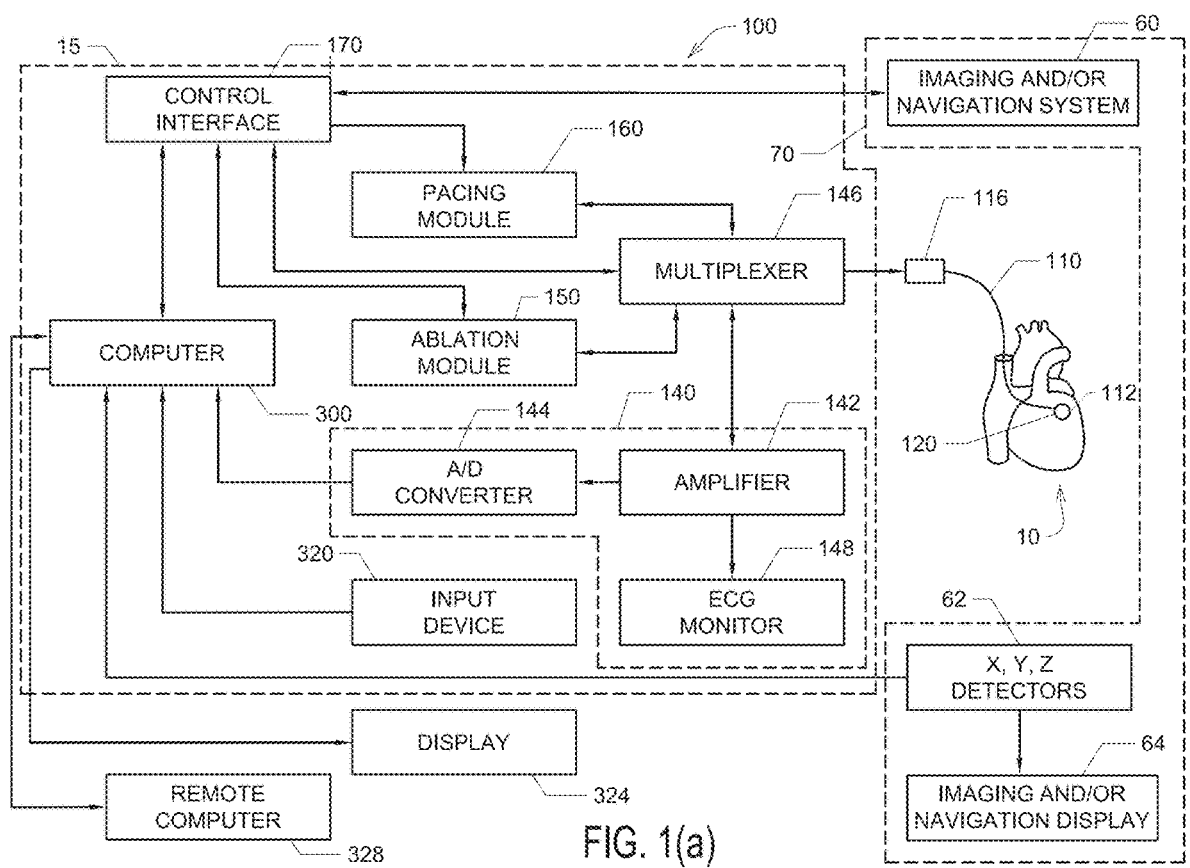
FIG. 1(a) shows one embodiment of a combined cardiac electrophysiological mapping (EP), pacing and ablation system 100.

Referring now to FIG. 1(a), there is illustrated one embodiment of a combined cardiac electrophysiological mapping (EP), pacing and ablation system 100. Note that in some embodiments system 100 may not include ablation module 150 and/or pacing module 160. Among other things, the embodiment of system 100 shown in FIG. 1(a) is configured to detect and reconstruct cardiac activation information acquired from a patient's heart relating to cardiac rhythm disorders and/or irregularities, and is further configured to detect and discover the location of the source of such cardiac rhythm disorders and/or irregularities with enhanced precision relative to prior art techniques. In some embodiments, system 100 is further configured to treat the location of the source of the cardiac rhythm disorder or irregularity, for example by ablating the patient's heart at the detected location.

The embodiment of system 100 shown in FIG. 1(a) comprises five main functional units: electrophysiological mapping (EP mapping unit) 140 (which is also referred to herein as data acquisition device 140), ablation module 150, pacing module 160, imaging and/or navigation system 70, and computer or computing device 300. Data acquisition, processing and control system 15 comprises data acquisition device 140, ablation module 150, pacing module 160, control interface 170 and computer or computing device 300. In one embodiment, at least one computer or computing device or system 300 is employed to control the operation of one or more of systems, modules and devices 140, 150, 160, 170 and 70. Alternatively, the respective operations of systems, modules or devices 140, 150, 160, 170 and 70 may be controlled separately by each of such systems, modules and devices, or by some combination of such systems, modules and devices.

Instead of being operably connected (e.g., through Bluetooth signals, a LAN or WAN network, or through the cloud), or directly connected, to computing device 300, data acquisition device 140 may be configured to provide as outputs therefrom saved or stored body surface electrogram signals, which can be, by way of example, saved or stored on a hard drive, in a memory, on a USB stick, or other suitable storage device, and where the saved or stored body surface electrogram signals are later or subsequently provided as inputs to computing device 300 for processing and analysis.

Computer or computing device 300 may be configured to receive operator inputs from an input device 320 such as a keyboard, mouse and/or control panel. Outputs from computer 300 may be displayed on display or monitor 324 or other output devices (not shown in FIG. 1(a)). Computer 300 may also be operably connected to a remote computer or analytic database or server 328. At least each of components, devices, modules and systems 60, 110, 140, 146, 148, 150, 170, 300, 324 and 328 may be operably connected to other components or devices by wireless (e.g., Bluetooth) or wired means. Data may be transferred between components, devices, modules or systems through hardwiring, by wireless means, or by using portable memory devices such as USB memory sticks.

During electrophysiological (EP) mapping procedures, multi-electrode catheter 110 is typically introduced percutaneously into the patient's heart 10. Catheter 110 is passed through a blood vessel (not shown), such as a femoral vein or the aorta, and thence into an endocardial site such as the atrium or ventricle of the heart 10.

It is contemplated that other catheters, including other types of mapping or EP catheters, lasso catheters, pulmonary vein isolation (PVI) ablation catheters (which can operate in conjunction with sensing lasso catheters), ablation catheters, navigation catheters, and other types of EP mapping catheters such as EP monitoring catheters and spiral catheters may also be introduced into the heart, and that additional surface electrodes may be attached to the skin of the patient to record electrocardiograms (ECGs).

When system 100 is operating in an EP mapping mode, multi-electrode catheter 110 functions as a detector of intra-electrocardiac signals, while optional surface electrodes may serve as detectors of surface ECGs. In one embodiment, the analog signals obtained from the intracardiac and/or surface electrodes are routed by multiplexer 146 to data acquisition device 140, which comprises an amplifier 142 and an A/D converter (ADC) 144. The amplified or conditioned electrogram signals may be displayed by electrocardiogram (ECG) monitor 148. The analog signals are also digitized via ADC 144 and input into computer 300 for data processing, analysis and graphical display.

In one embodiment, catheter 110 is configured to detect cardiac activation information in the patient's heart 10, and to transmit the detected cardiac activation information to data acquisition device 140, either via a wireless or wired connection. In one embodiment that is not intended to be limiting with respect to the number, arrangement, configuration, or types of electrodes, catheter 110 includes a plurality of 64 electrodes, probes and/or sensors A1 through H8 arranged in an 8×8 grid that are included in electrode mapping assembly 120, which is configured for insertion into the patient's heart through the patient's blood vessels and/or veins. Other numbers, arrangements, configurations and types of electrodes in catheter 110 are, however, also contemplated. In most of the various embodiments, at least some electrodes, probes and/or sensors included in catheter 110 are configured to detect cardiac activation or electrical signals, and to generate electrocardiograms or electrogram signals, which are then relayed by electrical conductors from or near the distal end 112 of catheter 110 to proximal end 116 of catheter 110 to data acquisition device 140.

Note that in some embodiments of system 100, multiplexer 146 is not employed for various reasons, such as sufficient electrical conductors being provided in catheter 110 for all electrode channels, or other hardware design considerations. In other embodiments, multiplexer 146 is incorporated into catheter 110 or into data acquisition device 140. In still further embodiments, multiplexer 146 is optional or not provided at all, and data acquisition device 140, ablation module 150, and/or pacing module 160 are employed separately and/or operate independently from one another. In addition, in some embodiments computing device 300 may be combined or integrated with one or more of data acquisition device 140, ablation module 150, and/or pacing module 160.

In one embodiment, a medical practitioner or health care professional employs catheter 110 as a roving catheter to locate the site of the location of the source of a cardiac rhythm disorder or irregularity in the endocardium quickly and accurately, without the need for open-chest and open-heart surgery. In one embodiment, this is accomplished by using multi-electrode catheter 110 in combination with real-time or near-real-time data processing and interactive display by computer 300, and optionally in combination with imaging and/or navigation system 70. In one embodiment, multi-electrode catheter 110 deploys at least a two-dimensional array of electrodes against a site of the endocardium at a location that is to be mapped, such as through the use of a Biosense Webster® PENTARAY® EP mapping catheter. The intracardiac or electrogram signals detected by the catheter's electrodes provide data sampling of the electrical activity in the local site spanned by the array of electrodes.

In one embodiment, the electrogram signal data are processed by computer 300 to produce a display showing the locations(s) of the source(s) of cardiac rhythm disorders and/or irregularities in the patient's heart 10 in real-time or near-real-time, further details of which are provided below. That is, at and between the sampled locations of the patient's endocardium, computer 300 may be configured to compute and display in real-time or near-real-time an estimated, detected and/or determined location(s) of the site(s), source(s) or origin)s) of the cardiac rhythm disorder(s) and/or irregularity(s) within the patient's heart 10. This permits a medical practitioner to move interactively and quickly the electrodes of catheter 110 towards the location of the source of the cardiac rhythm disorder or irregularity.

In some embodiments of system 100, one or more electrodes, sensors or probes detect cardiac activation from the surface of the patient's body as surface ECGs, or remotely without contacting the patient's body (e.g., using magneto-cardiograms). In another example, some electrodes, sensors or probes may derive cardiac activation information from echocardiograms. In various embodiments of system 100, external or surface electrodes, sensors and/or probes can be used separately or in different combinations, and further may also be used in combination with intracardiac electrodes, sensors and/or probes inserted within the patient's heart 10. Many different permutations and combinations of the various components of system 100 are contemplated having, for example, reduced, additional or different numbers of electrical sensing and other types of electrodes, sensors and/or transducers.

Continuing to refer to FIG. 1(a), EP mapping system or data acquisition device 140 is configured to condition the analog electrogram signals delivered by catheter 110 from electrodes A1 through H8 in amplifier 142. Conditioning of the analog electrogram signals received by amplifier 142 may include, but is not limited to, low-pass filtering, high-pass filtering, bandpass filtering, and notch filtering. The conditioned analog signals are then digitized in analog-to-digital converter (ADC) 144. ADC 144 may further include a digital signal processor (DSP) or other type of processor which is configure to further process the digitized electrogram signals (e.g., low-pass filter, high-pass filter, bandpass filter, notch filter, automatic gain control, amplitude adjustment or normalization, artifact removal, etc.) before they are transferred to computer or computing device 300 for further processing and analysis.

As discussed above, in some embodiments, multiplexer 146 is separate from catheter 110 and data acquisition device 140, and in other embodiments multiplexer 146 is combined in catheter 110 or data acquisition device 140.

In some embodiments, the rate at which individual electrogram and/or ECG signals are sampled and acquired by system 100 can range between about 0.25 milliseconds and about 8 milliseconds, and may be about 0.5 milliseconds, about 1 millisecond, about 2 milliseconds or about 4 milliseconds. Other sample rates are also contemplated. While in some embodiments system 100 is configured to provide unipolar signals, in other embodiments system 100 is configured to provide bipolar signals.

In one embodiment, system 100 can include a BARD® LABSYSTEM™ PRO EP Recording System, which is a computer and software driven data acquisition and analysis tool designed to facilitate the gathering, display, analysis, pacing, mapping, and storage of intracardiac EP data. Also, in one embodiment, data acquisition device 140 can include a BARD® CLEARSIGN™ amplifier, which is configured to amplify and condition electrocardiographic signals of biologic origin and pressure transducer input, and transmit such information to a host computer (e.g., computer 300 or another computer).

As shown in FIG. 1(a), and as described above, in some embodiments system 100 includes ablation module 150, which may be configured to deliver RF ablation energy through catheter 110 and corresponding ablation electrodes disposed near distal end 112 thereof, and/or to deliver RF ablation energy through a different catheter (not shown in FIG. 1(a)). Suitable ablation systems and devices include, but are not limited to, cryogenic ablation devices and/or systems, radiofrequency ablation devices and/or systems, ultrasound ablation devices and/or systems, high-intensity focused ultrasound (HIFU) devices and/or systems, chemical ablation devices and/or systems, and laser ablation devices and/or systems.

When system 100 is operating in an optional ablation mode, multi-electrode catheter 110 fitted with ablation electrodes, or a separate ablation catheter, is energized by ablation module 150 under the control of computer 300, control interface 170, and/or another control device or module. For example, an operator may issue a command to ablation module 150 through input device 320 to computer 300. In one embodiment, computer 300 or another device controls ablation module 150 through control interface 170. Control of ablation module 150 can initiate the delivery of a programmed series of electrical energy pulses to the endocardium via catheter 110 (or a separate ablation catheter, not shown in FIG. 1(a)). One embodiment of an ablation method and device is disclosed in U.S. Pat. No. 5,383,917 to Desai et al., the entirety of which is hereby incorporated by reference herein.

In an alternative embodiment, ablation module 150 is not controlled by computer 300, and is operated manually directly under operator control. Similarly, pacing module 160 may also be operated manually directly under operator control. The connections of the various components of system 100 to catheter 110, to auxiliary catheters, or to surface electrodes may also be switched manually or using multiplexer 146 or another device or module.

When system 100 is operating in an optional pacing mode, multi-electrode catheter 110 is energized by pacing module 160 operating under the control of computer 300 or another control device or module. For example, an operator may issue a command through input device 320 such that computer 300 controls pacing module 160 through control interface 170, and multiplexer 146 initiates the delivery of a programmed series of electrical simulating pulses to the endocardium via the catheter 110 or another auxiliary catheter (not shown in FIG. 1(a)). One embodiment of a pacing module is disclosed in M. E. Josephson et al., in "VENTRICULAR ENDOCARDIAL PACING II, The Role of Pace Mapping to Localize Origin of Ventricular Tachycardia," The American Journal of Cardiology, vol. 50, November 1982.

Computing device or computer 300 is appropriately configured and programmed to receive or access the electrogram signals provided by data acquisition device 140. Computer 300 is further configured to analyze or process such electrogram signals in accordance with the methods, functions and logic disclosed and described herein so as to permit reconstruction of cardiac activation information from the electrogram signals. This, in turn, makes it possible to locate with at least some reasonable degree of precision the location of the source of a heart rhythm disorder or irregularity. Once such a location has been discovered, the source may be eliminated or treated by means that include, but are not limited to, cardiac ablation.

In one embodiment, and as shown in FIG. 1(a), system 100 also comprises a physical imaging and/or navigation system 70. Physical imaging and/or navigation device 60 included in system 70 may be, by way of example, a 2- or 3-axis fluoroscope system, an ultrasonic system, a magnetic resonance imaging (MRI) system, a computed tomography (CT) imaging system, and/or an electrical impedance tomography EIT) system. Operation of system 70 be controlled by computer 300 via control interface 170, or by other control means incorporated into or operably connected to imaging or navigation system 70. In one embodiment, computer 300 or another computer triggers physical imaging or navigation system 60 to take "snap-shot" pictures of the heart 10 of a patient (body not shown). A picture image is detected by a detector 62 along each axis of imaging, and can include a silhouette of the heart as well as a display of the inserted catheter 110 and its electrodes A1-H8 (more about which is said below), which is displayed on imaging or navigation display 64. Digitized image or navigation data may be provided to computer 300 for processing and integration into computer graphics that are subsequently displayed on monitor or display 64 and/or 324.

In one embodiment, system 100 further comprises or operates in conjunction with catheter or electrode position transmitting and/or receiving coils or antennas located at or near the distal end of an EP mapping catheter 110, or that of an ablation or navigation catheter 110, which are configured to transmit electromagnetic signals for intra-body navigational and positional purposes.

In one embodiment, imaging or navigation system 70 is used to help identify and determine the precise two- or three-dimensional positions of the various electrodes included in catheter 110 within patient's heart 10, and is configured to provide electrode position data to computer 300. Electrodes, position markers, and/or radio-opaque markers can be located on various potions of catheter 110, mapping electrode assembly 120 and/or distal end 112, or can be configured to act as fiducial markers for imaging or navigation system 70.

Medical navigation systems suitable for use in the various embodiments described and disclosed herein include, but are not limited to, image-based navigation systems, model-based navigation systems, optical navigation systems, electromagnetic navigation systems (e.g., BIOSENSE® WEBSTER® CARTO® system), and impedance-based navigation systems (e.g., the St. Jude® ENSITE™ VELOCITY™ cardiac mapping system), and systems that combine attributes from different types of imaging AND navigation systems and devices to provide navigation within the human body (e.g., the MEDTRONIC® STEALTHSTATION® system).

In view of the structural and functional descriptions provided herein, those skilled in the art will appreciate that portions of the described devices and methods may be configured as processes, methods, data processing systems, and/or computer methods. Accordingly, these portions of the devices and methods described herein may take the form of a hardware embodiment, a software embodiment, or an embodiment combining software and hardware, such as shown and described with respect to computer system 300 illustrated in FIG. 1(b). Furthermore, portions of the devices and methods described herein may be a process or method stored in a computer-usable storage medium having computer readable program code on the medium. Any suitable computer-readable medium may be utilized including, but not limited to, static and dynamic storage devices, hard disks, optical storage devices, and magnetic storage devices.

Certain embodiments of portions of the devices and methods described herein are also described with reference to block diagrams of methods, processes, and systems. It will be understood that such block diagrams, and combinations of blocks diagrams in the Figures, can be implemented using computer-executable instructions. These computer-executable instructions may be provided to one or more processors of a general purpose computer, a special purpose computer, or any other suitable programmable data processing apparatus (or a combination of devices and circuits) to produce a machine, such that the instructions, which executed via the processor(s), implement the functions specified in the block or blocks of the block diagrams.

These computer-executable instructions may also be stored in a computer-readable memory that can direct computer 300 or other programmable data processing apparatus to function in a particular manner, such that the instructions stored in the computer-readable memory result in an article of manufacture including instructions which implement the function specified in an individual block, plurality of blocks, or block diagram. The computer program instructions may also be loaded onto computer 300 or other programmable data processing apparatus to cause a series of operational steps to be performed on the computer or other programmable apparatus to produce a computer implemented process such that the instructions which execute on computer 300 or other programmable apparatus provide steps for implementing the functions specified in the an individual block, plurality of blocks, or block diagram.

Figure 1B:
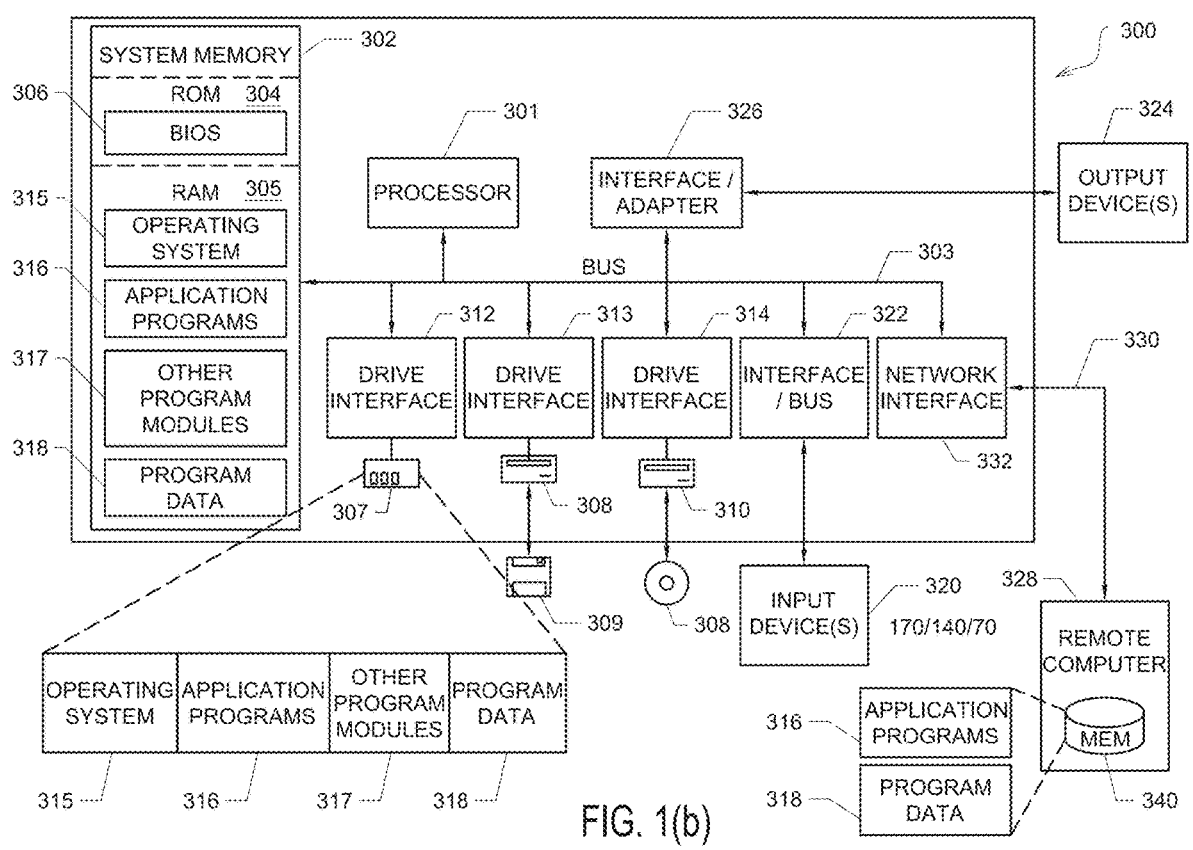
FIG. 1(b) shows one embodiment of a computer system 300.

In this regard, FIG. 1(b) illustrates only one example of a computer system 300 (which, by way of example, can include multiple computers or computer workstations) that can be employed to execute one or more embodiments of the devices and methods described and disclosed herein, such as devices and methods configured to acquire and process sensor or electrode data, to process image data, and/or transform sensor or electrode data and image data associated with the analysis of cardiac electrical activity and the carrying out of the combined electrophysiological mapping and analysis of the patient's heart 10 and ablation therapy delivered thereto.

Computer system 300 can be implemented on one or more general purpose computer systems or networked computer systems, embedded computer systems, routers, switches, server devices, client devices, various intermediate devices/nodes or standalone computer systems. Additionally, computer system 300 or portions thereof may be implemented on various mobile devices such as, for example, a personal digital assistant (PDA), a laptop computer and the like, provided the mobile device includes sufficient processing capabilities to perform the required functionality.

In one embodiment, computer system 300 includes processing unit 301 (which may comprise a CPU, controller, microcontroller, processor, microprocessor or any other suitable processing device), system memory 302, and system bus 303 that operably connects various system components, including the system memory, to processing unit 301. Multiple processors and other multi-processor architectures also can be used to form processing unit 301. System bus 303 can comprise any of several types of suitable bus architectures, including a memory bus or memory controller, a peripheral bus, or a local bus. System memory 302 can include read only memory (ROM) 304 and random-access memory (RAM) 305. A basic input/output system (BIOS) 306 can be stored in ROM 304 and contain basic routines configured to transfer information and/or data among the various elements within computer system 300.

Computer system 300 can include a hard disk drive 303, a magnetic disk drive 308 (e.g., to read from or write to removable disk 309), or an optical disk drive 310 (e.g., for reading CD-ROM disk 311 or to read from or write to other optical media). Hard disk drive 303, magnetic disk drive 308, and optical disk drive 310 are connected to system bus 303 by a hard disk drive interface 312, a magnetic disk drive interface 313, and an optical drive interface 314, respectively. The drives and their associated computer-readable media are configured to provide nonvolatile storage of data, data structures, and computer-executable instructions for computer system 300. Although the description of computer-readable media above refers to a hard disk, a removable magnetic disk and a CD, other types of media that are readable by a computer, such as magnetic cassettes, flash memory cards, digital video disks and the like, in a variety of forms, may also be used in the operating environment; further, any such media may contain computer-executable instructions for implementing one or more parts of the devices and methods described and disclosed herein.

A number of program modules may be stored in drives and RAM 303, including operating system 315, one or more application programs 316, other program modules 313, and program data 318. The application programs and program data can include functions and methods programmed to acquire, process and display electrical data from one or more sensors, such as shown and described herein. The application programs and program data can include functions and methods programmed and configured to process data acquired from a patient for assessing heart function and/or for determining parameters for delivering a therapy and/or assessing heart function, such as shown and described herein with respect to FIGS. 1-10(f).

A health care provider or other user may enter commands and information into computer system 300 through one or more input devices 320, such as a pointing device (e.g., a mouse, a touch screen, etc.), a keyboard, a microphone, a joystick, a game pad, a scanner, and the like. For example, the user can employ input device 320 to edit or modify the data being input into a data processing method (e.g., only data corresponding to certain time intervals). These and other input devices 320 may be connected to processing unit 301 through a corresponding input device interface or port 322 that is operably coupled to the system bus, but may be connected by other interfaces or ports, such as a parallel port, a serial port, or a universal serial bus (USB). One or more output devices 324 (e.g., display, a monitor, a printer, a projector, or other type of display device) may also be operably connected to system bus 303 via interface 326, such as through a video adapter.

Computer system 300 may operate in a networked environment employing logical connections to one or more remote computers, such as remote computer 328. Remote computer 328 may be a workstation, a computer system, a router, or a network node, and may include connections to many or all the elements described relative to computer system 300. The logical connections, schematically indicated at 330, can include a local area network (LAN) and/or a wide area network (WAN).

When used in a LAN networking environment, computer system 300 can be connected to a local network through a network interface or adapter 332. When used in a WAN networking environment, computer system 300 may include a modem, or may be connected to a communications server on the LAN. The modem, which may be internal or external, can be connected to system bus 303 via an appropriate port interface. In a networked environment, application programs 316 or program data 318 depicted relative to computer system 300, or portions thereof, may be stored in a remote memory storage device 340.

Figure 2:
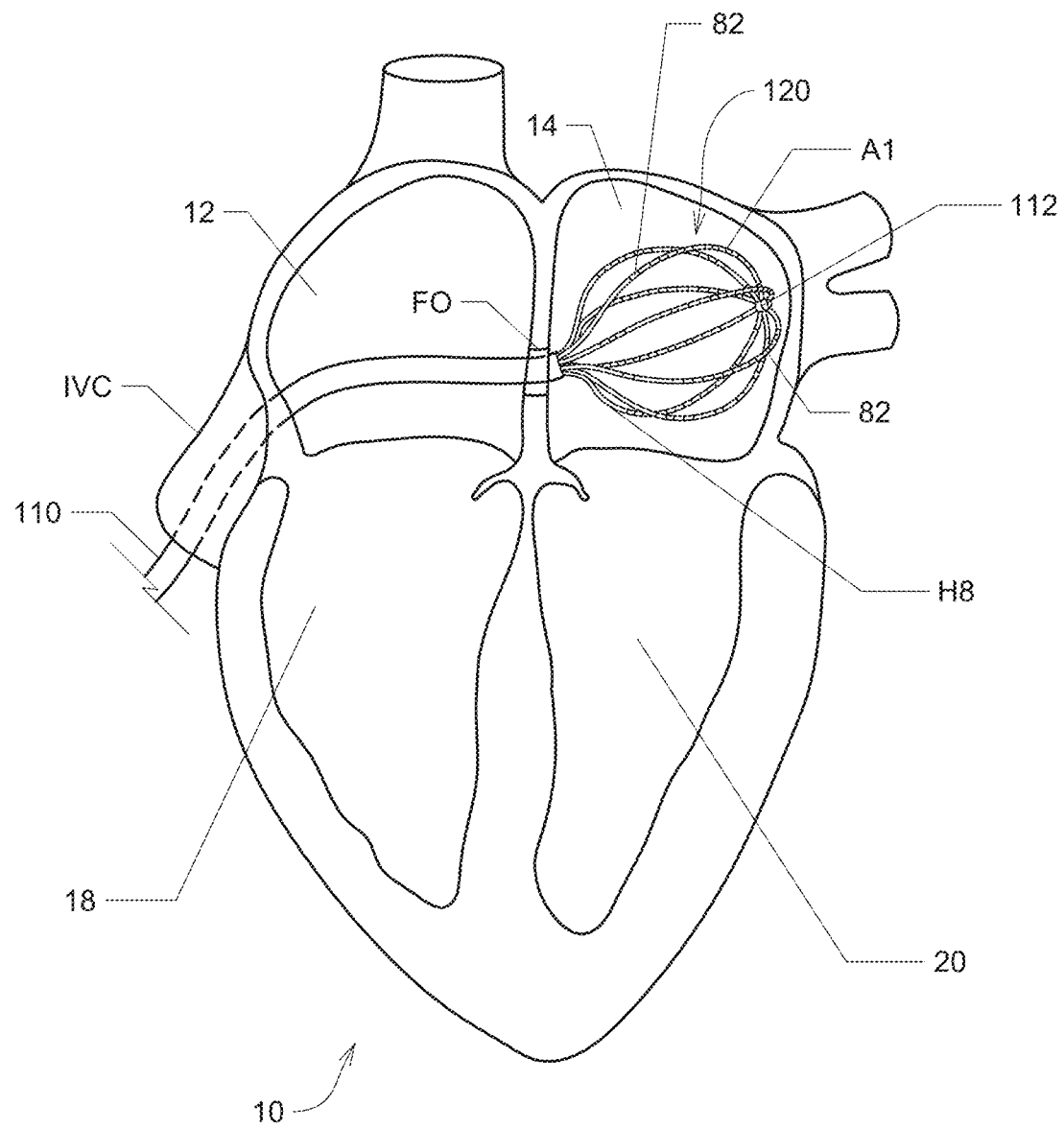
FIG. 2 shows an illustrative view of one embodiment of a distal portion of catheter 110 inside a patient's left atrium 14.

Referring now to FIG. 2, there is shown an illustrative view of one embodiment of a distal portion of catheter 110 inside a patient's left atrium 14. As shown in FIG. 2, heart 10 includes right atrium 12, left atrium 14, right ventricle 18, and left ventricle 20. Mapping electrode assembly 120 is shown in an expanded or open state inside left atrium 13 after it has been inserted through the patient's inferior vena cava and foramen ovalen ("IVC" and "FO" in FIG. 2), and in one embodiment is configured to obtain electrogram signals from left atrium 12 via an 8×8 array of electrodes A1 through H8, which as shown comprises individual electrodes 82. Mapping electrode assembly and catheter 110 may also be positioned within the patient's right atrium 12, left ventricle 18 and right ventricle 20.

Figure 3:
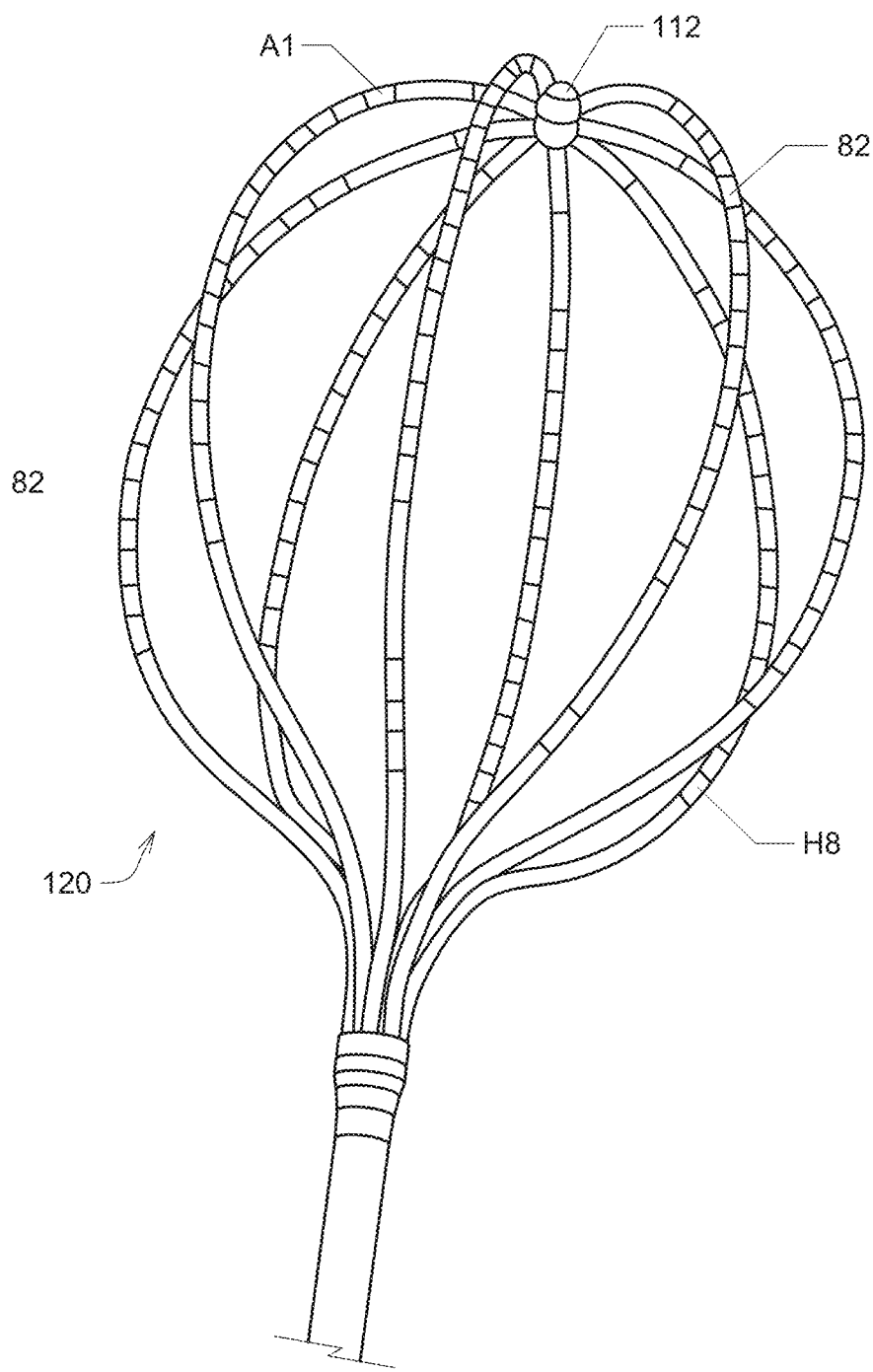
FIG. 3 shows an illustrative embodiment of a mapping electrode assembly 120.

FIG. 3 shows an illustrative embodiment of a mapping electrode assembly 120, which in FIG. 3 forms a distal portion of a Boston Scientific® CONSTELLATION® full contact mapping catheter. The CONSTELLATION EP catheter permits full-contact mapping of a patient's heart chamber, and may also be employed to facilitate the assessment of entrainment, conduction velocity studies, and refractory period in a patient's heart 10. Mapping electrode assembly 120 shown in FIG. 3 permits the simultaneous acquisition of longitudinal and circumferential signals for more accurate 3-D mapping, and features a flexible basket design that conforms to atrial anatomy and aids aid in accurate placement. Sixty-four electrodes A1 through H8 (or individual electrodes 82) can provide comprehensive, real-time 3-D information over a single heartbeat.

Figure 4:
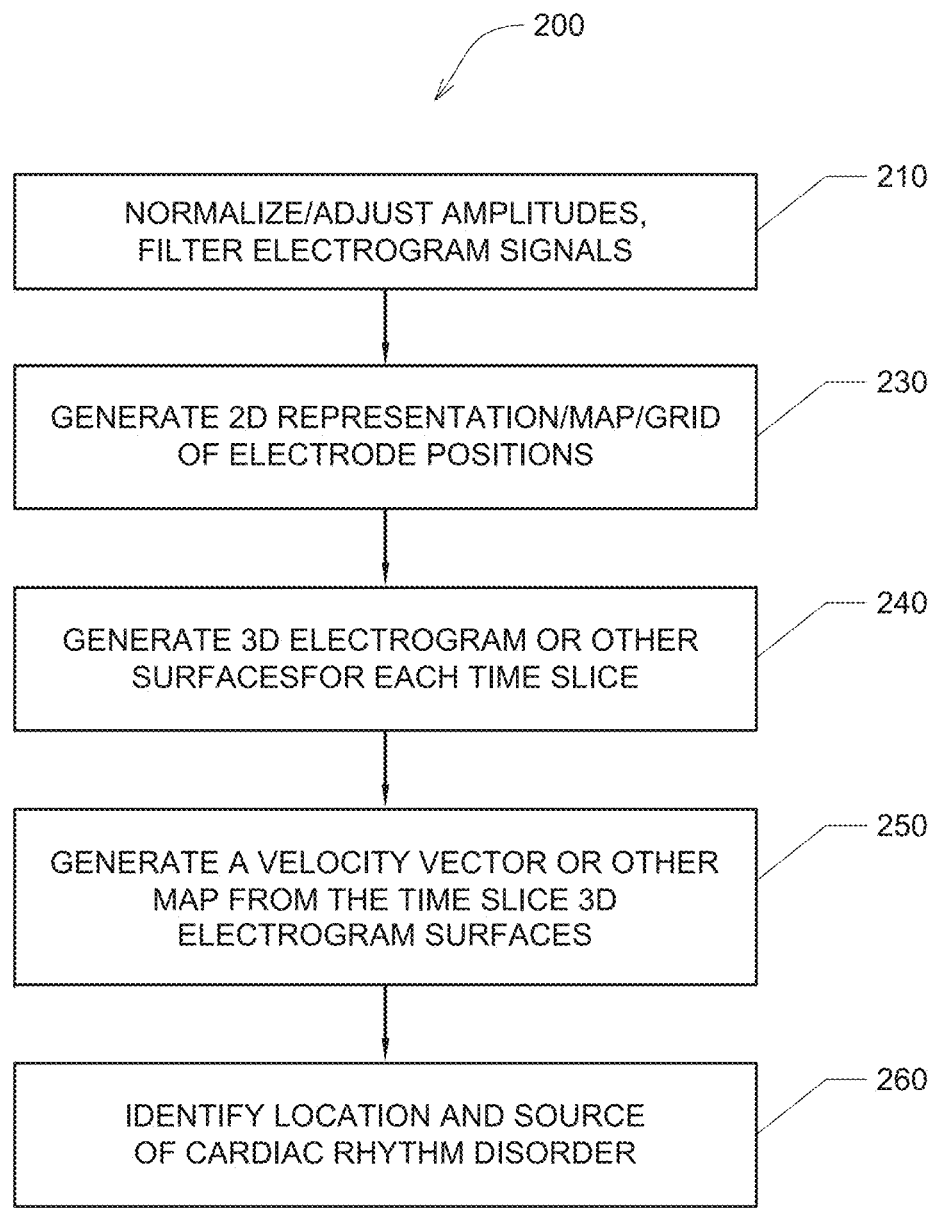
FIG. 4 shows one embodiment of a method 200 of detecting a location of a source of at least one cardiac rhythm disorder in a patient's heart.

FIG. 4 shows one embodiment of a method 200 of detecting a location of a source of at least one cardiac rhythm disorder in a patient's heart. At step 210, the amplitudes of electrogram signals acquired from electrodes located inside a patient's heart are normalized or adjusted. At step 230, positions A1 through H8 corresponding to each of the electrodes of mapping electrode assembly 120 are assigned to the individual electrogram signals that have been acquired. At step 230, a two-dimensional (2D) spatial map of electrode positions A1 through H8 is generated or provided. In some embodiments, a three-dimensional (3D) spatial map of electrode positions A1 through H8 is generated or provided. (As discussed above, fewer or more than 64 electrodes may be used to measure electrogram signals and/or surface ECGs, and electrode arrays other than 8×8 or rectangular grids are contemplated in the various embodiments.)

For discrete or selected times over which the electrogram signals are being analyzed and processed, at step 240 the amplitude-adjusted electrogram signals are processed to generate a plurality of three-dimensional electrogram surfaces (which according to one embodiment may be smoothed electrogram surfaces) corresponding at least partially to the 2D (or 3D) map, one surface being generated for each such discrete time. At step 250, the plurality of three-dimensional electrogram surfaces that have been generated through time are processed to generate a velocity vector or other type of map corresponding at least partially to the 2D (or 3D) map, which in some embodiments can also be called a three-dimensional electrographic flow or EGF map. (Note that generating other types of maps is also contemplated herein, including, but not limited to, generating maps using video tracking, motion capture, motion estimation, SwisTrack, particle tracking, and single-particle tracking techniques, more about which is said below.) The velocity vector map or EGF map, or other type of map, is configured to reveal the location of the source of the at least one cardiac rhythm disorder. In a subsequent optional step (not shown in FIG. 4), method 200 further comprises ablating or otherwise treating patient's heart 10 at the location of the source of the cardiac rhythm disorder indicated by the velocity vector or other type of map.

Method 200 outlined in FIG. 4 presents one embodiment of a method of processing electrogram signals provided by one or more mapping catheters so as to transform time domain waveform information into space domain information, and then calculate velocity vector maps that correspond to normalized space potential profile movements for each point in space. For reasons that are explained below, method 200 has the advantages that it is robust against artifacts and provides a virtual resolution that is higher than the actual electrode density employed to acquire the EP mapping data through the use of a fitting method that determines the most likely mean spatial velocity map derived from hundreds of individual samples of amplitude patterns recorded by the mapping electrodes.

As described above, in step 210 of FIG. 4 the amplitudes of electrogram signals acquired from electrodes located inside the patient's heart are normalized or otherwise adjusted. In step 240, the amplitude-adjusted electrogram signals are processed across a 2D or 3D map to generate a plurality of three-dimensional electrogram surfaces, one surface being generated for each such discrete time. In one embodiment, the resulting individual time-slice surfaces can be strung together sequentially to provide a time-varying depiction of electrical activation occurring over the portion of the patient's heart that has been monitored. According to embodiments that have been discovered to be particularly efficacious in the field of intracardiac EP monitoring and data processing and analysis, at least portions of the electrogram surfaces are found to correspond to estimated wave shapes, and are generated using Green's function, which in some embodiments, and by way of non-limiting example, may be combined with two-or three-dimensional bi-harmonic spline interpolation functions to generate such surfaces.

In one embodiment, electrogram signal data acquired from the patient's heart 10 are not equidistantly sampled. For example, in one such embodiment, electrogram signal data acquired from the patient's heart 10 are not equidistantly sampled by mapping electrode assembly 120, and instead are assigned their respective chessboard locations A1 through H8 as approximations of electrode locations in a cylindrical 2D projection of a grid representative of the interior surface of the patient's heart that is being mapped. In many applications, it has been discovered that such approximations of electrode locations yield perfectly usable and accurate results when steps 230 through 250 are carried out after steps 210 and 230.

In another embodiment, when superimposing the acquired electrogram signal data onto a 2D or 3D map or grid in step 230, the electrogram signal data may be associated with their actual or more accurately estimated positions in the 2D projection of the grid using positional data provided by, for example, imaging or navigation system 70. Resampling of electrogram signals on the grid may also be carried out. Gridding may also be carried out such as by convolution-type filtering, Kriging, and using splines. Most gridding techniques operate on an equidistant grid and solve the equations governing the gridding process with either finite difference or finite element implementations.

One approach that has been discovered to work particularly well with electrogram signal data is to determine the Green's function associated with each electrogram value assigned to a given chessboard location, and then construct the solution as a sum of contributions from each data point, weighted by the Green's function evaluated for each point of separation. Biharmonic spline interpolation, which as described above may be employed in conjunction with Green's function, has also been discovered to work especially well in the context of processing and analyzing electrogram signal data. In some embodiments, undesirable oscillations between data points are removed by interpolation with splines in tension, also using Green's function. A Green's function technique for interpolation and surface fitting and generation of electrogram signal data has been found to be superior to conventional finite-difference methods because, among other things, the model can be evaluated at arbitrary x,y locations rather than only on a rectangular grid. This is a very important advantage of using Green's function in step 240, because precise evenly-spaced-apart grid locations, resampling of electrogram signals, and finite-difference gridding calculations are not required to generate accurate representations of electrogram surfaces in step 240.

In one embodiment, Green's function $G(x; x')$ is employed in step 240 for a chosen spline and geometry to interpolate data at regular or arbitrary output locations. Mathematically, the solution is $w(x)=\text{sum } \{c(i) G(x'; x(i))\}$, for $i=1, n$, and a number of data points $\{x(i), w(i)\}$. Once the n coefficients $c(i)$ have been calculated, the sum may be evaluated at any output point x. A selection is made between minimum curvature, regularized, or continuous curvature splines in tension for either 1-D, 2-D, or 3-D Cartesian coordinates or spherical surface coordinates. After removing a linear or planar trend (i.e., in Cartesian geometries) or mean values (i.e., spherical surfaces) and normalizing residuals, a least-squares matrix solution for spline coefficients $c(i)$ may be determined by solving the n by n linear system $w(j)=\text{sum-over-i } \{c(i) G(x(j); x(i))\}$, for $j=1, n$; this solution yields an exact interpolation of the supplied data points. For further details regarding the methods and mathematics underlying Green's function, see, for example: (1) "Moving Surface Spline Interpolation Based on Green's Function," Xingsheng Deng and Zhong-an Tang, Math. Geosci (2011), 43:663-680 ("the Deng paper"), and (2) "Interpolation with Splines in Tension: A Green's Function Approach," Paul Wessel and David Bercovici, Mathematical Geology, 77-93, Vol. 30, No. 1, 1998 ("the Wessel paper"). The respective entireties of the Deng and Wessel papers are hereby incorporated by reference herein.

Still further details regarding the use of Green's function in interpolating and generating surfaces may be found in: Interpolation by regularized spline with tension: I. Theory and implementation, Mitasova, H., and L. Mitas, 1993, Math. Geol., 25, 641-655; Parker, R, L., 1994, Geophysical Inverse Theory, 386 pp., Princeton Univ, Press, Princeton, N.J.; Sandwell, D. T., 1987, Biharmonic spline interpolation of Geos-3 and Seasat altimeter data, Geophys. Res. Lett., 14, 139-142; Wessel, P., and J. M. Becker, 2008, Interpolation using a generalized Green's function for a spherical surface spline in tension, Geophys. J. Int, 174, 21-28, and Wessel, P., 2009, A general-purpose Green's function interpolator, Computers & Geosciences, 35, 1247-1254. Moving Surface Spline Interpolation Based on Green's Function, Xingsheng Deng, Zhong-an Tang, Mathematical Geosciences, August 2011, Volume 43, Issue 6, pp 663-680.

Note, however, that a number of different surface smoothing, surface fitting, surface estimation and/or surface/data interpolation processing techniques may be employed in step 240 of FIG. 4, which are not limited to Green's function, or use in conjunction with Green's function, and which include, but are not limited to, inverse distance weighted methods of interpolation, triangulation with linear interpolation, bilinear surface interpolation methods, bivariate surface interpolation methods, cubic convolution interpolation methods, Kriging interpolation methods, Natural Neighbor or "area-stealing" interpolation methods, spline interpolation techniques (including bi-harmonic spline fitting techniques and "spline with barriers" surface interpolation methods), global polynomial interpolation methods, moving least squares interpolation methods, polynomial least square fitting interpolation methods, simple weighted-average operator interpolation methods, multi-quadric biharmonic function interpolation methods, and artificial neural network interpolation methods. See, for example: "A brief description of natural neighbor interpolation (Chapter 2)," in V. Barnett. Interpreting Multivariate Data. Chichester: John Wiley. pp. 21-36.), and "Surfaces generated by Moving Least Squares Methods," P. Lancaster et al., Mathematics of Computation, Vol. 37, No. 155 (July 1981), 141-158).

As described above, in step 250 of FIG. 4, the plurality of three-dimensional electrogram surfaces may be processed through time to generate a velocity vector map or EGF map, or other type of map, corresponding at least partially to the 2D (or 3D) map, the velocity vector or other type of map being configured to reveal the location of the source of the at least one cardiac rhythm disorder. According to embodiments that have been discovered to be particularly efficacious in the field of intracardiac EP monitoring and subsequent data processing and analysis, at least portions of the velocity vector map are generated using one or more optical flow analysis and estimation techniques and methods. Such optical flow analysis techniques may include one or more of Horn-Schunck, Buxton-Buston, Black-Jepson, phase correlation, block-based, discrete optimization, Lucas-Kanade, and differential methods of estimating optical flow. From among these various optical flow estimation and analysis techniques and methods, however, the Horn-Schunck method has so far been discovered to provide superior results in the context of processing and analyzing cardiac electrogram signals, for reasons that are discussed in further detail below.

Two papers describe the Horn-Schunck method particularly well: (1) "SimpleFlow: A Non-iterative, Sublinear Optical Flow Algorithm," Michael Tao et al., Eurographics 2012, Vol. 31 (2012), No. 2 ("the Tao paper"), and (2) "Horn-Schunck Optical Flow with a Multi-Scale Strategy," Enric Meinhardt-Llopis et al., Image Processing On Line, 3 (2013), pp. 151-172 ("the Meinhardt-Llopis paper"). The respective entireties of the Tao and Meinhardt-Llopis papers are hereby incorporated by reference herein.

In "Determining Optical Flow," by B. K. P. Horn and B. G. Schunck, Artificial Intelligence, Vol. 17, pp. 185-204, 1981, the entirety of which is also hereby incorporated by reference herein, a method for finding an optical flow pattern is described which assumes that the apparent velocity of a brightness pattern varies smoothly throughout most of an image. The Horn-Schunck method assumes smoothness in flow over most or all of an image. Thus, the Horn-Schunck method attempts to minimize distortions in flow and prefers solutions which exhibit smoothness. The Horn-Schunck method of estimating optical flow is a global method which introduces a global constraint of smoothness to solve the aperture problem of optical flow.

A description of some aspects of conventional application of the Horn-Schunck method is set forth in U.S. Pat. No. 6,480,615 to Sun et al. entitled "Motion estimation within a sequence of data frames using optical flow with adaptive gradients," the entirety of which is also hereby incorporated by reference herein. As described by Sun et al., the Horn-Schunck computation is based on the observation that flow velocity has two components, and that a rate of change of image brightness requires only one constraint. Smoothness of flow is introduced as a second constraint to solve for optical flow. The smoothness constraint presumes there are no spatial discontinuities. As a result, Horn and Schunck excluded situations where objects in an image occlude or block one another. This is because at object boundaries of an occlusion in an image, discontinuities in reflectance appear.

In conventional optical flow analysis, image brightness is considered at pixel (x,y) in an image plane at time t to be represented as a function I(x,y,t). Based on initial assumptions that the intensity structures of local time-varying image regions are approximately constant under motion for at least a short duration, the brightness of a particular point in the image is constant, so that dI/dt=0. Based on the chain rule of differentiation, an optical flow constraint equation (I) can be represented as follows:

$$Ix(x,y,t) \cdot u + Iy(x,y,t) \cdot v + It(x,y,t) = 0,$$

where $Ix = \partial I(x,y,t)/\partial x$ = horizontal spatial gradient of the image intensity;

$Iy = \partial I(x,y,t)/\partial y$ = vertical spatial gradient of the image intensity;

$It = \partial I(x,y,t)/\partial t$ = temporal image gradient of the image intensity;

$u = dx/dt$ = horizontal image velocity (or displacement); and $v = dy/dt$ = vertical image velocity (or displacement).

The above optical flow equation is a linear equation having two unknowns, (i.e., u and v). The component of motion in the direction of the brightness gradient is known to be $It/(Ix^2+Iy^2)^{1/2}$. However, one cannot determine the component of movement in the direction of the iso-brightness contours at right angles to the brightness gradient. As a consequence, the optical flow velocity (u,v) cannot be computed locally without introducing additional constraints. Horn and Schunck therefore introduce a smoothness constraint. They argue that if every point of the brightness pattern can move independently, then there is little hope of recovering the velocities. However, if opaque objects of finite size are undergoing rigid motion or deformation, neighboring points on the objects should have similar velocities. Correspondingly, the velocity field of the brightness patterns in the image will vary smoothly almost everywhere.

Advantages of the Horn-Schunck method include that it yields a high density of flow vectors, the flow information missing in inner parts of homogeneous objects is filled in from the motion boundaries. On the negative side, the Horn-Schunck method can be sensitive to noise.

The foregoing discussion regarding how the Horn-Schunck optical flow technique typically focuses on conventional applications, where the brightness or intensity of an object changes over time (which is where the term "optical flow" is derived from). Here, the brightness or intensity of an object is not the issue at hand. Instead, the amplitudes of electrogram signals, and how they change shape and propagate in time and space over a patient's heart, are sought to be determined. One underlying objective of method 200 is to produce a vector velocity map, which is a representation of electrographical flow (and not optical flow) within a patient's heart. Instead of looking for differences or changes in optical brightness or intensity, changes in the velocity, direction and shape of electrical signals (i.e., changes in electrographical flow) across a patient's heart are determined. That is, method 200 does not process optical measurement data corresponding to intensity or brightness, but processes electrical measurement data corresponding to amplitude, potential shape, and/or voltage.

One reason why method 200 works so well in detecting the locations of the sources of cardiac rhythm disorders and irregularities is that ion channels in a patient's heart produce action potential voltages that are relatively constant (except in areas of fibrosis). As described above, the Horn-Schunck method assumes "brightness constancy" as one of its key constraints. The normalized/amplitude-adjusted electrogram signals provided by step 210 help satisfy this key constraint of the Horn-Schunck method so that this method may be applied successfully in step 250.

In addition, because of the stability imparted to electrographical flow solutions determined using the Horn-Schunck method, artifacts and noise are generally low in velocity vector maps generated in step 250. In fact, it is believed that the Horn-Schunck method may generally be applied with greater success to electrographical flow data than to optical data because of the unique nature of action potential signals in the human heart, and the manner in which electrogram signals are processed and conditioned before an optical flow analysis is performed on them as described and disclosed herein.

Method 200 described and disclosed herein also does not employ spatial derivatives of electrical potentials (as is done by Deno et al. and Kumaraswamy Nanthakumar using "omnipolar" signals) or time derivatives of electrogram signals (as is done in the TOPERA system). Time derivatives of signals are known to increase noise. Method 200 has as its key inputs the potentials of electrogram signals (not their derivatives). As a result, method 200 is notably free from the effects of spurious noise and artifacts introduced by time-derivative data processing techniques, including in step 250.

In another embodiment, the velocity vector map of step 250 is generated using the Lucas-Kanade optical flow method, which is a differential method for optical flow estimation developed by Bruce D. Lucas and Takeo Kanade. It assumes that the flow is essentially constant in a local neighbourhood of a pixel under consideration, and solves the basic optical flow equations for all the pixels in that neighborhood using least squares criteria. By combining information from several nearby pixels, the Lucas-Kanade method can often resolve the inherent ambiguity of the optical flow equation. It is also less sensitive to image noise than point-wise methods. On the other hand, since it is a purely local method, it cannot provide flow information in the interior of uniform regions of the image. See "An Iterative Image Registration Technique with an Application to Stereo Vision," Bruce D. Lucase, Takeo Kanade, Proceedings of Imaging Understanding Workshop, pp. 121-130 (1981), the entirety of which is hereby incorporated by reference herein.

In yet another embodiment, various aspects of the Horn-Schunck and Lucas-Kanade methods are combined to yield an optical flow method that exhibits the local methods inherent in Lucas-Kanade techniques and the global methods inherent in the Horn-Schunck approach and its extensions. Often local methods are more robust under noise, while global techniques yield dense flow fields. See, for example, "Lucas/Kanade Meets Horn/Schunck: Combining Local and Global Optic Flow Methods," Andrés Bruhn, Joachim Weickert, Christoph Schnörr, International Journal of Computer Vision, February 2005, Volume 61, Issue 3, pp 211-231, the entirety of which is hereby incorporated by reference herein.

Various embodiments of method 200 feature several advantages with respect to prior art systems and methods that generate intracardiac images and attempt to detect the locations of cardiac rhythm disorders or irregularities. A key underlying assumption of signal processing techniques that employ Hilbert Transform, Discrete Fourier Transforms (DFTs) or Fast Fourier Transforms (FFTs) is that the signal to be transformed is periodic. As is well known in the field of digital signal processing, this underlying basic assumption is frequently incorrect, and can lead to problems such as spectral leakage. Contrariwise, in some embodiments of method 200, an underlying assumption is that the electrical activity in a patient's heart is based upon ion channel activation, which is a stochastic and non-periodic process, and so strictly periodic behaviour is not assumed or required in subsequent data processing and manipulation steps.

Indeed, none of steps 210, 230, 240, or 250 of method 200 absolutely requires the use of Hilbert or Fourier transforms to process data. Instead, in some embodiments each of these steps can be carried out in the time domain without the need for frequency domain or quadrature conversion. For example, in step 210 the amplitudes of the various traces or electrograms can be normalized or adjusted in the time domain according to a selected standard deviation. In another example, rotors detected by method 200 are not assumed to be singularities in a phase map (as is assumed in techniques based upon frequency domain or Hilbert transform signal processing). This key difference also explains why the rotational direction of a rotor can be revealed or detected accurately by method 200 (and not at all, or very unsatisfactorily, using the frequency domain or Hilbert transforms of other methods employed to detect rotors). Note that in some embodiments, however, Hilbert, DFT and/or FFT signal processing components may be or are included in the data processing flow of method 200 (e.g., DSP filtering, deconvolution, etc.).

Continuing to refer to FIG. 4, and in particular to step 250 thereof, as mentioned above techniques other than optical flow or EGF can be employed to generate flow or vector maps or other suitable visual or digital representations, including, but not limited to, generating maps, images, or representations using video tracking, motion capture, motion estimation, SwisTrack, particle tracking, and single-particle or other suitable particle tracking techniques.

Video (or visual) tracking involves locating one or more moving objects or events over time using consecutive video frames or stills generated, according to one embodiment, from video or other visual representations of the plurality of sequential three-dimensional electrogram surfaces generated in step 240. Video tracking is used to correlate or associate target events or objects in consecutive video frames. Correlation or association can be difficult when the objects or events are moving quickly relative to the frame rate, or where a tracked object or event changes orientation or direction over time (which, in the case of rotors and other types of sources of cardiac rhythm disorders, is to be expected). Consequently, video tracking techniques can employ motion models that describe how an image of a target or event might change for different possible motions of the object or event. Such motion models can be computationally intensive.

Some pertinent examples of motion models for use in video tracking include, but are not limited to: (a) 2D transformation for planar events or objects (e.g., affine transformation or homography) of an image of the object or event (e.g., the initial frame); (b) defining aspects depending on an object's or event's 3D position and orientation; (c) dividing key frames into macroblocks for video compression; and (d) defining motion of an object or event by the positions of nodes of a mesh.

In some embodiments, a video or visual tracking algorithm is employed to analyze sequential video or image frames, and outputs the movement of targets or events between frames. A number of different algorithms can be employed for this purpose. Typically, there major components of a video or visual tracking system include target representation and localization, and filtering and data association. Target representation and localization provide tools for identifying a moving object or event. Accurately locating and tracking a target object or event can depend on the suitability and robustness of the selected video or visual algorithm, some examples of which include, but are not limited to: (a) kernel-based tracking (e.g., mean-shift tracking), which is an iterative localization procedure based on maximizing a similarity measure such as a Bhattacharyya coefficient; (b) contour tracking, which involves the detection of object boundaries (e.g., active contours, or a condensation or conditional density propagation algorithm).

Filtering and data association involves incorporating prior information about a scene or object, taking into account object or event dynamics, and evaluating different explanations. Such methods permit the tracking of complex objects or events. Some common video or visual tracking filtering algorithms include, but are not limited to: (a) Kalman filters (see, for example, He F., Zhen J., Wang Z, (2020) Video Target Tracking Based on Adaptive Kalman Filter. In: Liang Q., Wang W., Liu X., Na Z., Jia M., Zhang B. (eds) Communications, Signal Processing, and Systems. CSPS 2019. Lecture Notes in Electrical Engineering, vol 571. Springer, Singapore, the entirety of which is hereby incorporated by reference herein); and (b) particle filters (see, for example, Liu J, Chen Y, Zhou L, Zhao L (2018) Visual tracking in high-dimensional particle filter. PLOS ONE 13(8): e0201872, https://doi.org/10.1371/journal.pone.0201872, the entirety of which is hereby incorporated by reference herein).

Sometimes considered subsets of video or visual tracking techniques are motion capture, motion estimation, SwisTrack, particle tracking, and single-particle tracking methods, algorithms, and techniques, some embodiments of which find application in step 250 of method 200 shown in FIG. 4.

Motion capture or motion tracking involves recording or capturing the movement of objects or events. In motion capture sessions, movements of objects or events should be sampled at spatial and temporal frequencies or rates sufficiently above the pertinent Nyquist frequency associated with the events or objects to permit accurate and reliable reconstruction of the movement of the objects or events from frame to frame. Because the objects or events of interest originate inside or on a patient's heart 10, markerless motion capture or tracking techniques are generally preferred, which do not require objects or events of interest to wear special equipment or tags for tracking. Some computer algorithms have been designed which can be adapted to permit system 300 to analyze video or image inputs and identify pertinent cardiac disorder events or objects, breaking them down into their constituent parts for tracking. For further technical details regarding motion capture or tracking techniques, methods and algorithms, see, for example: (a) Functional Categorization of Objects using Real-time Markerless Motion Capture to Gall et al., IEEE Conference on Computer Vision and Pattern Recognition (CVPR'11), 1969-1976, 2011, the entirety of which is hereby incorporated by reference herein, and (b) Xudong Zhu, Kin Fun Li, "Real-Time Motion Capture: An Overview", Complex Intelligent and Software Intensive Systems (CISIS) 2016 10th International Conference on, pp. 522-525, 2016, the entirety of which is hereby incorporated by reference herein.

Motion estimation involves determining motion vectors describing the transformation of one 2D image to another, where adjacent or nearby images or frames in a sequence are employed. Difficulties in doing so can ensue because the motion described actually occurs in in three dimensions while the resulting images are a projection of a 3D scene onto a 2D plane. In the context of revealing cardiac rhythm disorders and their associated objects and/or events, useful motion vectors need to relate to specific portions of the resulting images and the cardiac wall(s) associated therewith. Translational, rotational, and/or other types of models can be used to approximate motion between or along frames. As employed herein, the term "motion estimation" is not strictly synonymous, and according to the embodiment in questions may not be synonymous, with the term "optical flow," which instead is described in detail above. Motion estimation involves finding corresponding points between two images or video frames. In motion estimation, matching metrics are typically employed to measure how similar two corresponding points in different frames are. Selection of a matching metric technique or process sometimes involves consideration of what the final estimated motion is, and/or the optimization strategy that has been used in the estimation process.

Methods for finding motion vectors include pixel-based methods ("direct methods") and feature-based methods ("indirect methods"). Direct methods include, but are not limited to, block-matching algorithms, phase correlation and frequency domain methods, pixel recursive algorithms, while indirect methods include corner detection and matching corresponding features between frames (which typically employ one or more statistical functions such as RANSAC applied over a pertinent area of one or more images). For further technical details regarding motion estimation techniques, methods and algorithms, see, for example: (a) M. G. Strinzis and I. Kokkinidis, "Maximum likelihood motion estimation in ultrasound image sequences," in IEEE Signal Processing Letters, vol. 4, no. 6, pp. 156-157, June 1997, doi: 10.1109/97.586034, the entirety of which is hereby incorporated by reference herein, and (b) S. Golemati, A. Gastounioti and K. S. Nikita, "Ultrasound-Image-Based Cardiovascular Tissue Motion Estimation," in IEEE Reviews in Biomedical Engineering, vol. 9, pp. 208-218, 2016, doi: 10.1109/RBME.2016.2558147, the entirety of which is hereby incorporated by reference herein.

SwisTrack is a data association and segmentation tracking tool that can be configured to use images or frames as input sources. In one embodiment, and by way of non-limiting example, SwisTrack uses Intel's OpenCV library for fast image processing and contains interfaces for USB, FireWire and GigE cameras, as well as AVI files. SwisTrack has a flexible architecture that permits users to track marked and markerless objects or events (or "agents"). In SwisTrack, "components" are connected in a component pipeline and configured. Each component then performs one processing step, which can be visualized in real-time. Position and trajectory information can be retrieved via TCP/IP in NMEA 0183 format. Such data can easily be recorded for post-processing, or used in a real-time fashion. SwisTrack has mainly been developed by the Distributed Intelligent Systems and Algorithms Laboratory (DISAL) and the LPM Vision Group at EPFL in Lausanne, Switzerland. Version 4 of SwisTrack is an open source project for simultaneous tracking of multiple objects or events. SwisTrack's broad range of pre-implemented algorithmic components allows it to be used in a variety of experimental applications. Advanced users can implement additional customized modules, which extend the functionality of existing components within the provided interface. For further technical details regarding the data association and segmentation techniques and algorithms employed in the SwisTrack tracking tool, see, for example: (a) T. Lochmatter, P. Roduit, C. Cianci, N. Correll, J. Jacot and A. Martinoli, "SwisTrack—A Flexible Open Source Tracking Software for Multi-Agent Systems," 2008 IEEE/RSJ International Conference on Intelligent Robots and Systems, Nice, France, 2008, pp. 4004-4010, doi: 10.1109/IROS.2008.4650937, the entirety of which is hereby incorporated by reference herein, and (b) Correll, Nikolaus & Sempo, Grégory & Lopez de Meneses, Yuri & Halloy, Jose & Deneubourg, Jean-Louis & Martinoli, A. (2006). SwisTrack: A Tracking Tool for Multi-Unit Robotic and Biological Systems. IEEE International Conference on Intelligent Robots and Systems. 2185-2191. 10.1109/IROS.2006.282558.

Particle tracking, and its subset single-particle tracking (SPT), involve the observation of the motion of individual or multiple particles within a given medium, A particle's coordinates' time series, which can be expressed in two dimensions (x, y) or three dimensions (x, y, z), is a trajectory. A trajectory is typically analyzed using statistical methods to extract information about the underlying dynamics of a particle's motion. Once images have been obtained, single-particle tracking is mainly a two-step process. First, particles are detected in the images. Then, localized different particles in different images are connected to obtain individual trajectories.

TrackMate is one embodiment and example of a tool that can be used to perform SPT. SPT provides an image analysis challenge where the goal is to segment and follow over time labeled, spot-like structures. Each spot is segmented in multiple frames and its trajectory is reconstructed by assigning it an identity over such frames, which form a track. The resulting tracks can then be visualized. TrackMate can also be configured to yield further analysis and results, such as particle or object velocity, total displacement, rotational characteristics, etc. Though these objects may be represented by an X,Y,Z,T coordinate arrays, TrackMate can compute numerical features for each particle, spot or object, given its coordinates and a radius. For instance, the mean, max, min and median intensity can be computed for each such particle, spot or object, as well as the estimated radius and orientation for each such particle, spot or object, which permits the evolution of each feature of an object to be observed over time. For further technical details regarding particle and single-particle tracking techniques, methods and algorithms, see, for example: (a) Tinevez, Jean-Yves & Perry, Nick & Schindelin, Johannes & Hoopes, Genevieve & Reynolds, Gregory & Laplantine, Emmanuel & Bednarek, Sebastian & Shorte, Spencer & Eliceiri, Kevin. (2016). TrackMate: An Open and Extensible Platform for Single-Particle Tracking. Methods. 115. 10.1016/j.ymeth.2016.09.016, the entirety of which is hereby incorporated by reference herein, and (b) Smith, Matthew & Karatekin, Erdem & Gohlke, Andrea & Mizuno, Hiroaki & Watanabe, Naoki & Vavylonis, Dimitrios. (2011). Interactive, Computer-Assisted Tracking of Speckle Trajectories in Fluorescence Microscopy: Application to Actin Polymerization and Membrane Fusion. Biophysical journal. 101. 1794-804. 10.1016/j.bpj.2011.09.007, the entirety of which is hereby incorporated by reference herein.

Figure 5A:
FIG. 5(a) shows a simple rotor model.

Referring now to FIG. 5(a), there is shown a simple rotor model. This model was used to generate simulated ECG signals sensed by an 8×8 array of virtual electrodes. The simple rotor model shown in FIG. 5(a) is from "Chaste: An Open Source C++ Library for Computational Physiology and Biology," Gary R. Mirams, et al. PLOS Computational Biology, Mar. 14, 2013, Vol. 9, Issue 3, e1002970, the entirety of which is hereby incorporated by reference herein.

Figure 5B:
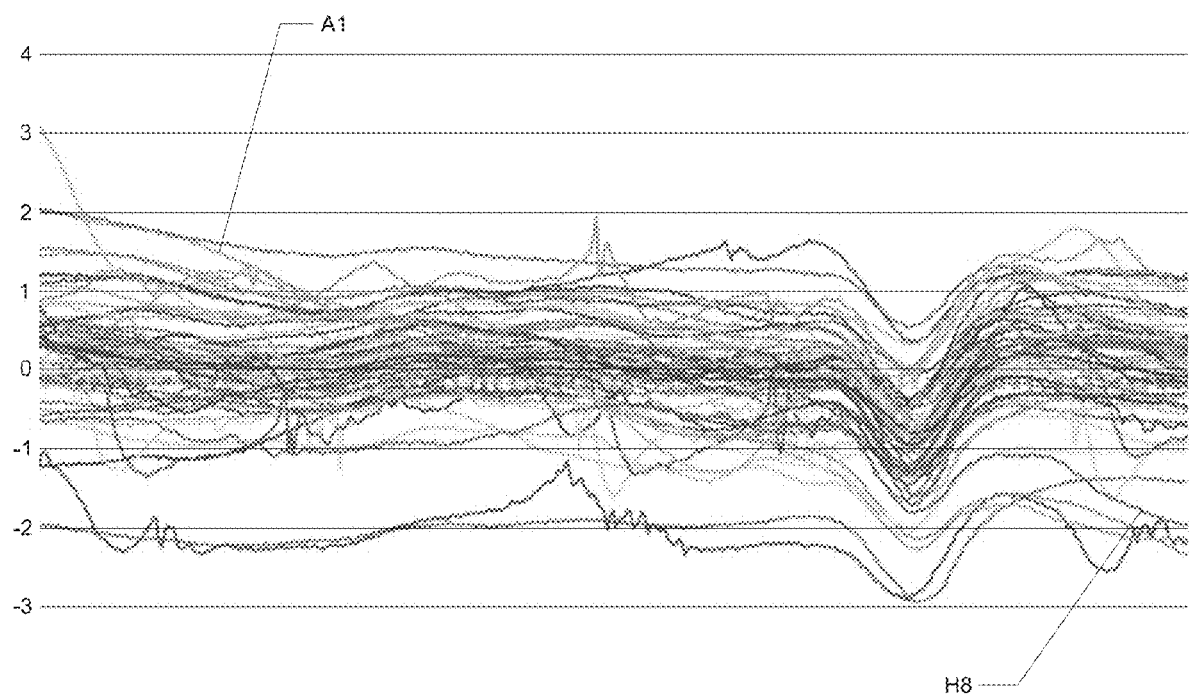
FIG. 5(b) shows sensed artifacts in electrogram signals.

FIG. 5(b) shows artifacts in electrogram signals derived from actual patient data, where 400 msec. traces were recorded using a 64-electrode basket catheter located in the left atrium of a patient suffering from atrial fibrillation. As shown in FIG. 5(b), the sensed artifacts in the electrogram signals include DC offsets of several millivolts that shift with time, a common far-field ventricular depolarization superimposed on the local potentials sensed by individual electrodes, and noise. Moreover, the amplitudes of the various sensed electrogram signals shown in FIG. 5(b) will be seen to vary considerably. These amplitude variations result at least in part on from varying degrees to which individual electrodes touch, or are physically is coupled to, the patient's endocardial surface. Electrogram signals corresponding to electrodes in loose, poor or no contact with a patient's endocardium may be an order of magnitude smaller than those where electrodes are well coupled to the endocardial surface.

Figure 5C:
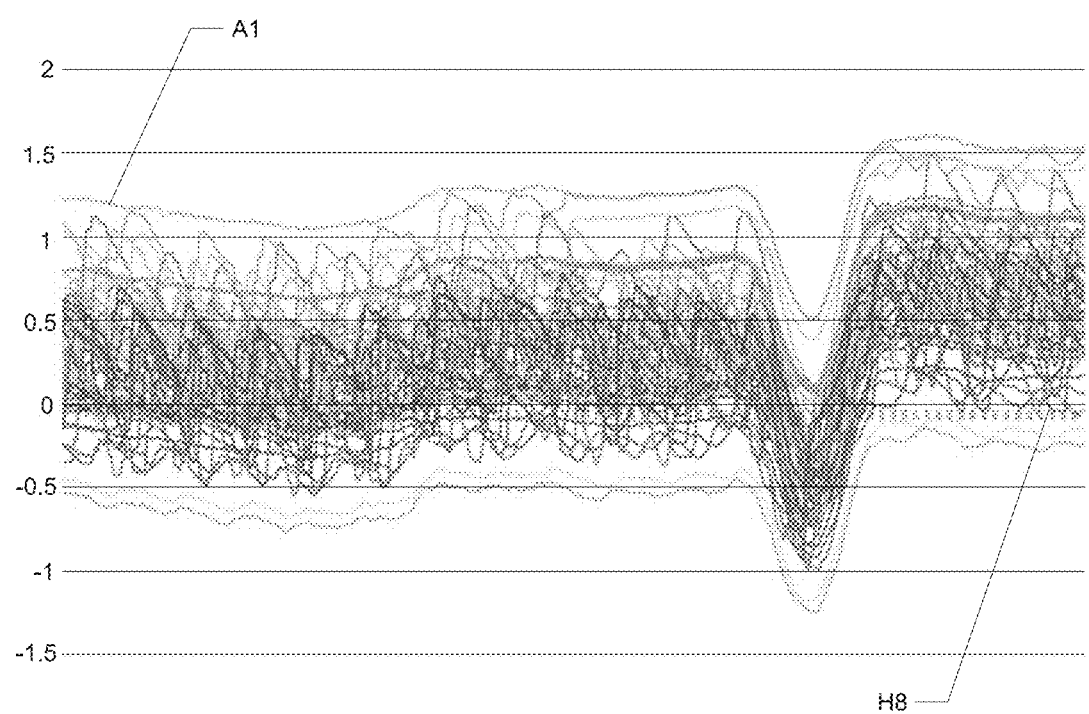
FIG. 5(c) shows the artifacts of FIG. 5(b) superimposed on simulated ECG signals.
Figure 5D:
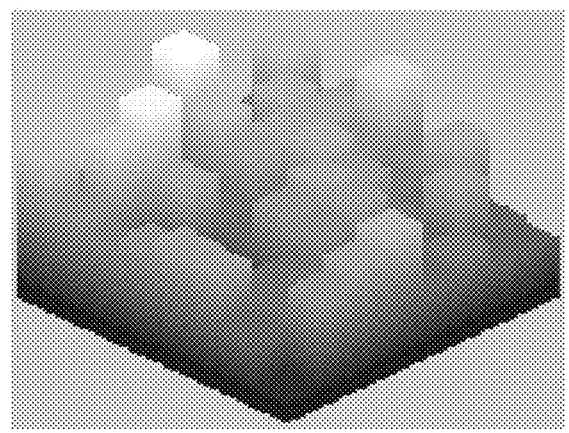
FIG. 5(d) shows a box plot corresponding to an 8×8 array of 64 electrode signals.

FIG. 5(c) shows the artifacts of FIG. 5(b) superimposed on the simulated ECG signals generated from the rotor model of FIG. 5(a), FIG. 5(d) shows a box plot corresponding to the 8×8 array of 64 electrode signals shown in FIG. 5(a) at a selected common time for all traces. Because of the artifacts from FIG. 5(b) introduced into the electrogram signals of FIG. 5(c), the box plot of FIG. 5(d) appears quite irregular and chaotic, and the original spiral shape of the underlying rotor of FIG. 5(a) is not discernible to the eye.

The data shown in FIG. 5(c) were used to perform an analysis in accordance with method 200, which was carried out in three main steps: (1) normalization/adjustment/filtering of electrogram signals; (2) generating three-dimensional smoothed electrogram surfaces for discrete times or time slices from the normalized/adjusted/filtered electrogram signals generated in the first main step, and (3) generating a velocity vector map based on the smoothed electrogram surfaces generated in the second main step.

Figure 5E:
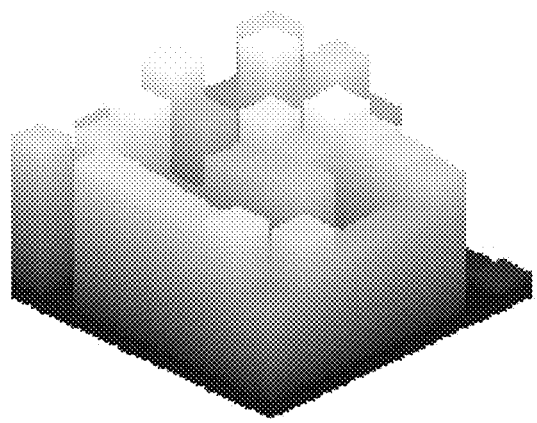
FIG. 5(e) shows the data of FIG. 5(d) after they have been subjected to an electrode signal normalization, adjustment and filtering process.

Described now is one embodiment and illustrative example of the first main step of the method 200 (normalization/adjustment/filtering of electrogram signals), Referring now to FIG. 5(e), there are shown the data of FIG. 5(d) after they have been subjected to one embodiment of an electrode signal normalization, adjustment and filtering process. After normalization and filtering, the simple rotor structure shown in FIG. 5(a) becomes visible in FIG. 5(e). Uniform electrode signal amplitude minima and maxima were first calculated and then applied to individual electrogram signals to generate individual amplitude equalized electrogram signals. Unwanted artifacts such as ventricular depolarization signals were removed from the individual equalized electrogram signals by first averaging all electrogram signals to generate a common electrogram artifact signal, which was then subtracted from each of the equalized individual electrogram signals. The resulting equalized artifact-compensated electrogram signals were then high-pass filtered between 5 and 20 Hz to remove DC offsets from the electrogram signals such that the resulting filtered electrogram signals were approximately zeroed around the X (time) axis. These results are shown in FIG. 5(e).

Next, a sliding time window ranging between about 0.1 seconds and about to 1 second in length was applied to each filtered electrogram signal to generate individual amplitude-adjusted electrogram signals. (In some embodiments, the length of the sliding time window corresponds to, or is less than, the slowest repetition frequency expected to be present.) The resulting sliding-window amplitude-adjusted electrogram signals were then stored for later use to generate image backgrounds in velocity vector maps, where they could be used to show low amplitude areas indicative of valve defects/artifacts, loose electrode contact, and/or areas of fibrosis in the patient's myocardium. In the sliding-window amplitude-adjusted electrogram signals, the respective minima and maxima of each position of the sliding time window were used to normalize the amplitude values of all signals between zero and one (or 0 and 255 on an 8-bit integer numeric scale). Because the maximum and minimum values occurred at different time points for electrodes placed in different locations, this process yielded spatial information regarding action potential wave patterns for each sampled time point (more about which is said below).

Now we describe one embodiment and illustrative example of the second main step of the method 200 (generating three-dimensional electrogram surfaces for discrete times or time slices, or estimation of spatial wave shapes). The second step of method 200 takes the spatial distributions of all electrodes and their normalized voltage values at discrete times (e.g., the data represented by the box plots corresponding to selected discrete times within the selected time window over which electrogram signals were acquired and measured), and estimates or generates from such data or box plots corresponding to given discrete times respective continuous voltage surfaces (or action potential waveform estimates) in space. Because the electrode pattern density is limited, and depending on the method that is used to generate the estimated voltage surfaces, the estimated surfaces typically deviate to some extent from "true" surfaces. Such deviations are usually relatively small in magnitude, however, since the spatial size of the action potential wave given by its velocity (e.g., 0.5 to 1 m/sec.) times the action potential duration (e.g., 0.1 to 0.2 sec.) is much larger (e.g., 0.05 m) than the electrode spacing (e.g., about 1 mm to about 10 mm), and thus spatial aliasing generally does not occur. The electrode grid provided by catheter 110 thus permits relatively good estimates of action potential wave shapes or wavefronts in the form of smoothed electrogram surfaces to be obtained as they propagate across the myocardium. On the other hand, because of the fast sampling rate (which can, for example, range between about 0.25 milliseconds and about 8 milliseconds, and which in some embodiments is nominally about 1 millisecond), changes in the spatial shape or expression of the action potential wavefront from one sample to the next are typically relatively small (e.g., about 1 mm) compared to the electrode distances (which in some embodiments nominally range between about 2 mm and about 7 mm). Thus, method 200 is capable of detecting spatial changes in action potential wavefronts or wave shapes using time domain information (i.e., small amplitude changes between time samples) to estimate changes in the spatial domain (where relatively small shifts in action potentials occur at given electrode measurement locations).

Figure 5F:
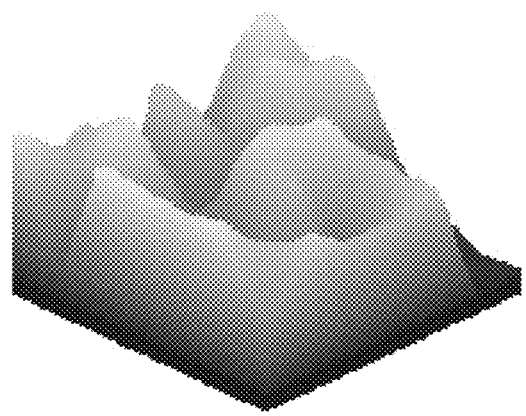
FIG. 5(f) shows a surface generated from the data shown in FIG. 5(e)

One embodiment of a method for estimating action potential wavefronts or wave shapes employs an 8×8 rectangular electrode grid (e.g., TOPERA®-like) model, which operates in two principal steps. First, each electrode/electrogram signal value at a discrete moment in time defines the height of its respective box in the "chess field" box plots shown in FIGS. 5(d) and 5(e). Second, a smoothed electrogram surface is generated for each box plot (or discrete slice of time) by calculating for each horizontal x-y point (typically on a 300×300 grid) an average of neighboring z-values (or electrical potentials) in the box plot. In 3D models that take assumed or actual electrode positions and spacing into account (using, e.g., information from a navigation or imaging system), smoothed electrogram surfaces are generated using 2D biharmonic spline interpolation techniques in combination with Green's function. Using the foregoing simple averaging approach, the smoothed electrogram surface of FIG. 5(f) was generated from the data shown in FIG. 5(e). As shown in FIG. 5(f), a spatial wave shape estimate of a rotor appears prominently in the forward center portion of the resulting smoothed surface, which tracks closely the original spiral wave shown in FIG. 5(a).

Described now is one embodiment and illustrative example of the third main step of method 200 (generating a velocity vector map based on the electrogram surfaces). The third main step of method 200 uses the action potential wave shape estimates or electrogram surfaces generated at discrete times or time splices provided by the second main step to calculate a velocity vector map. For each sample interval a spatial wave shape or smoothed surface is calculated according to the second main step described above. Since the wave shapes differ only by a small delta between individual samples, and minimum and maximum values are normalized, shift vectors can be calculated at a spatial resolution that is higher than the spatial resolution of the electrodes (e.g., 30×30 samples). Since individual shifts between samples may differ according to random error, a velocity vector fit can be generated using 40 to 100 samples, where an average of observed shift vectors of the action potential wave shape care calculated. If the angle of a rotating wavefront is shifted by a few degrees per sample, the vector arrows will exhibit a circular pattern and in fact can resolve circles that are much smaller than inter-electrode distances. In one embodiment, the third main step of the method employs a vector pattern equation that best fits the observed movement of the evaluated spatial element or wavefront. In one embodiment that has been discovered to provide excellent results, and as described above, the velocity vector map is calculated using the Horn-Schunck optical flow method described above. That is, in one embodiment the Horn-Schunck optical flow method is used in the third main step of method 200 to estimate the velocity and direction of wavefronts or wave shapes between sampled times. Velocities of 40 to 100 samples are typically averaged to yield the most stable results.

Figure 5G:
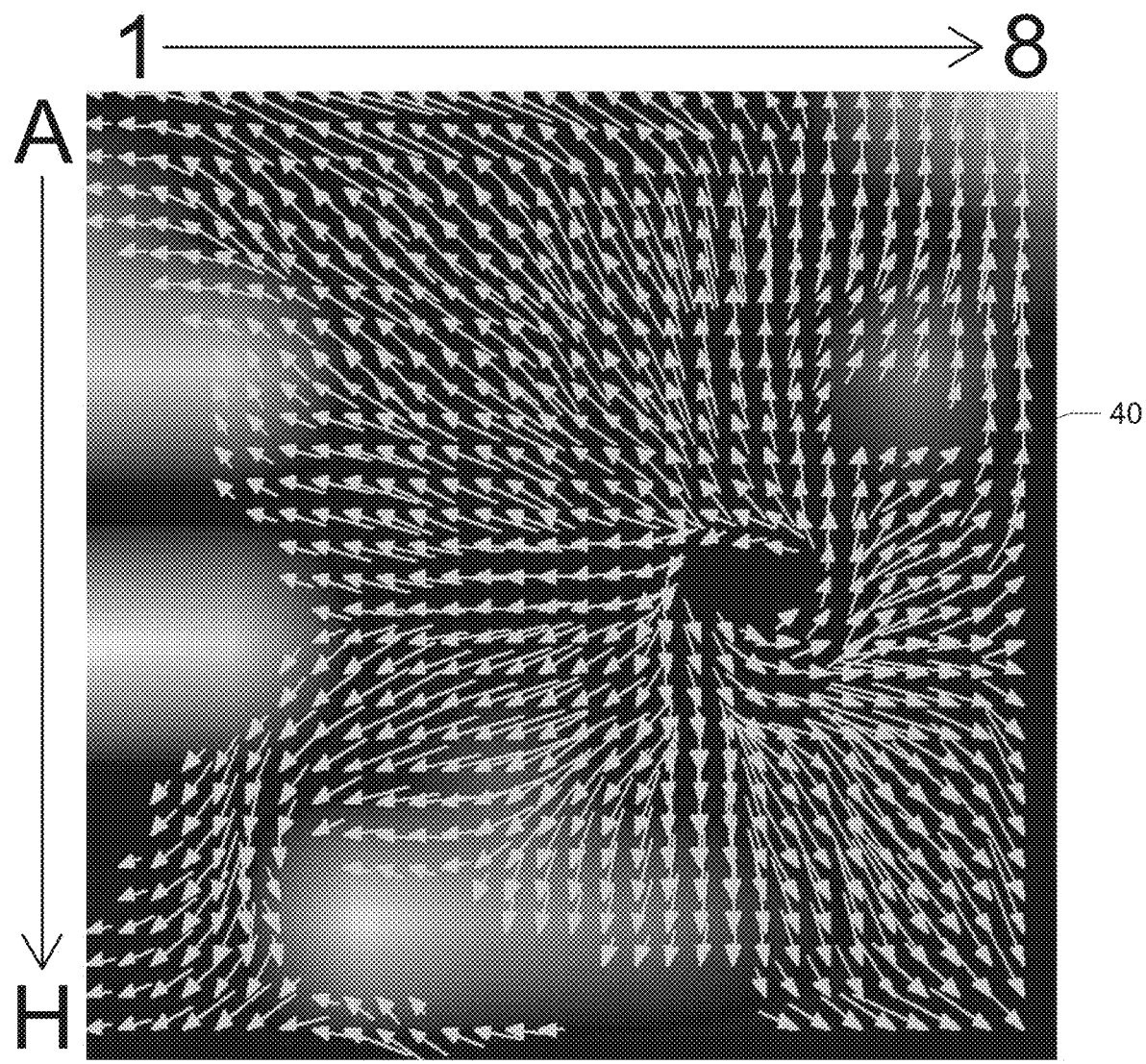
FIG. 5(g) shows wavefront velocity vectors.

FIG. 5(g) shows the resulting wavefront velocity vectors, which are shown in FIG. 5(g) and elsewhere in the Figures as arrows 40 having directions and magnitudes associated therewith, calculated from a series of 60 averaged time slices of smoothed surfaces samples corresponding to the data shown in FIG. 5(f). An active rotor is distinctly visible in the right-hand central portion of FIG. 5(g), where arrows are flowing tightly in a counterclockwise direction. In FIG. 5(g), action potential wavefronts are seen to be moving outwardly away from the detected active rotor (as would be expected in the case of an active rotor)).

Figure 6A:
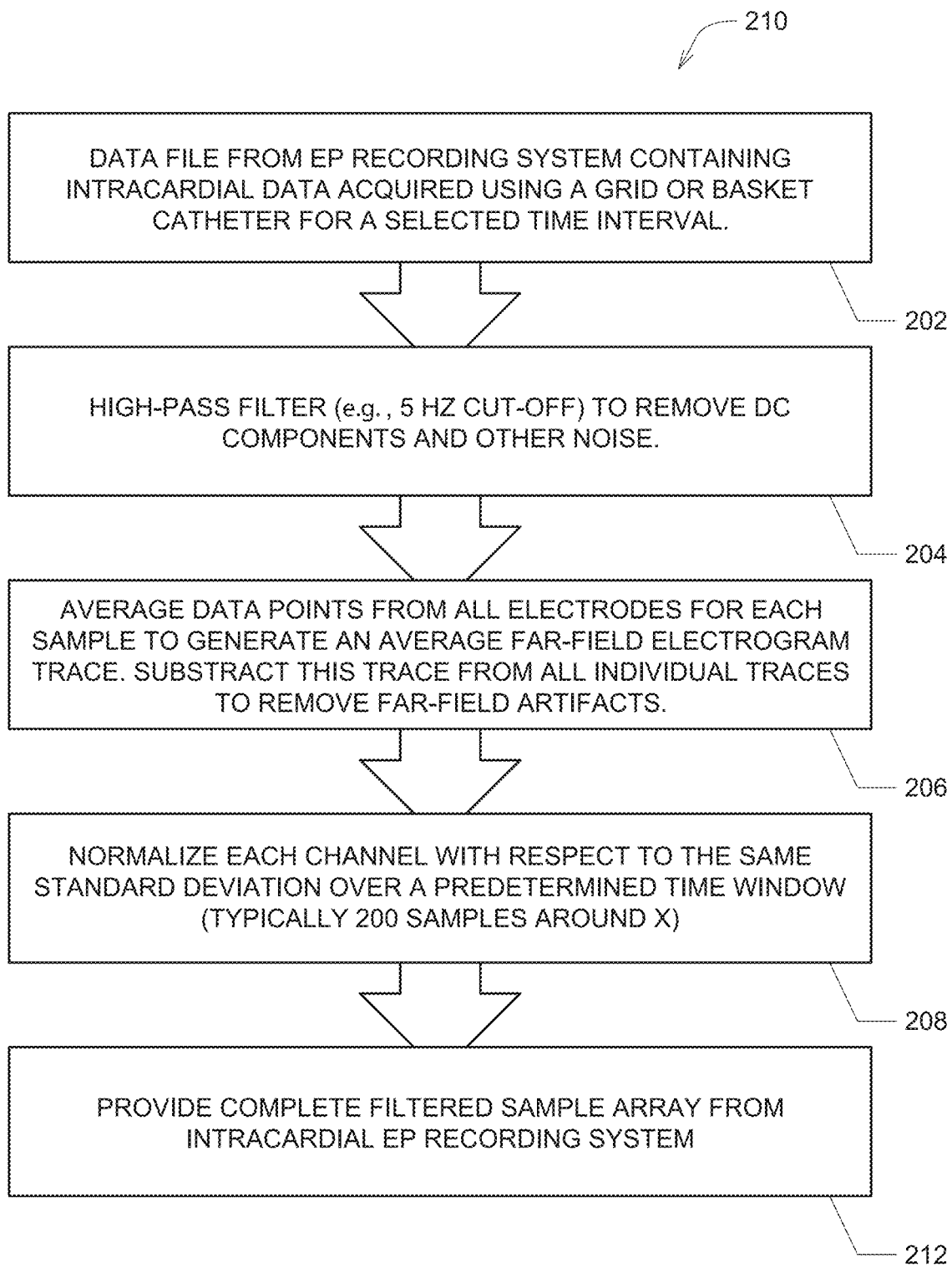
FIGS. 6(a) through 6(c) show details regarding one embodiment of a method 200 shown in FIG. 4.
Figure 6B:
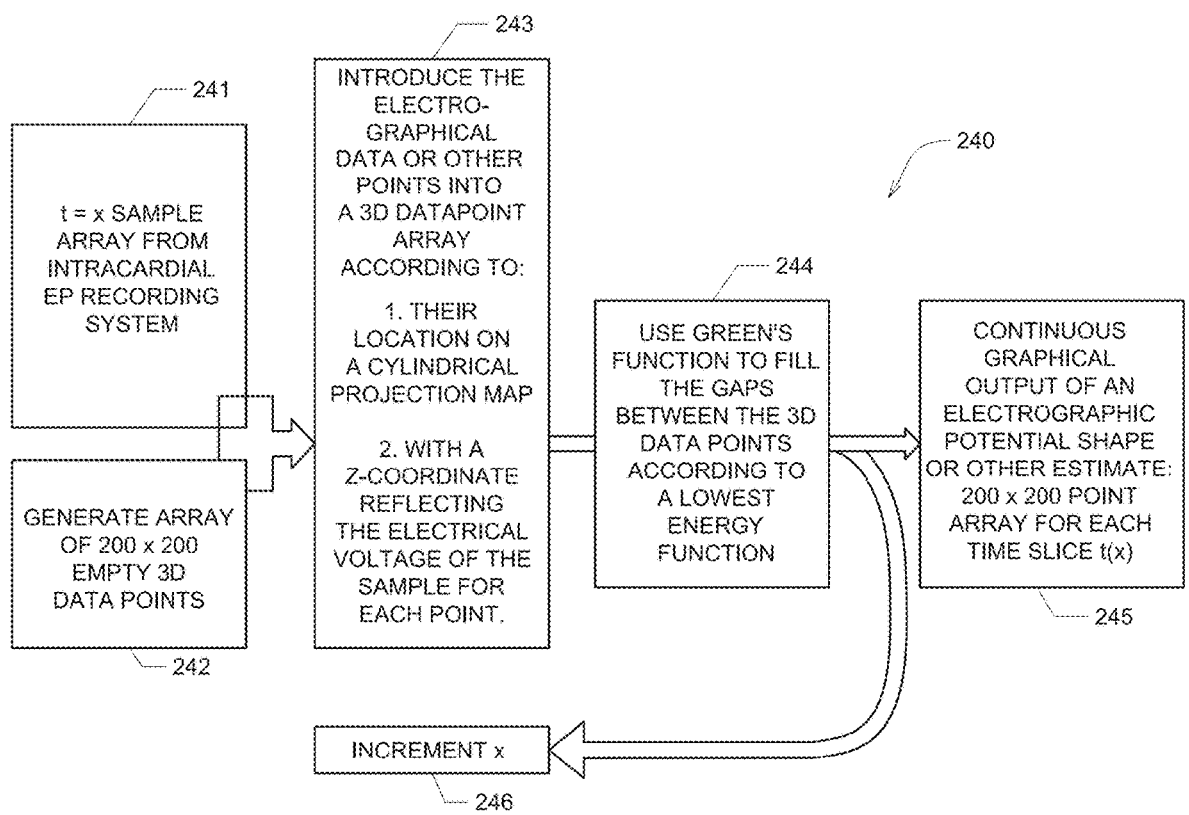
Figure 6C:
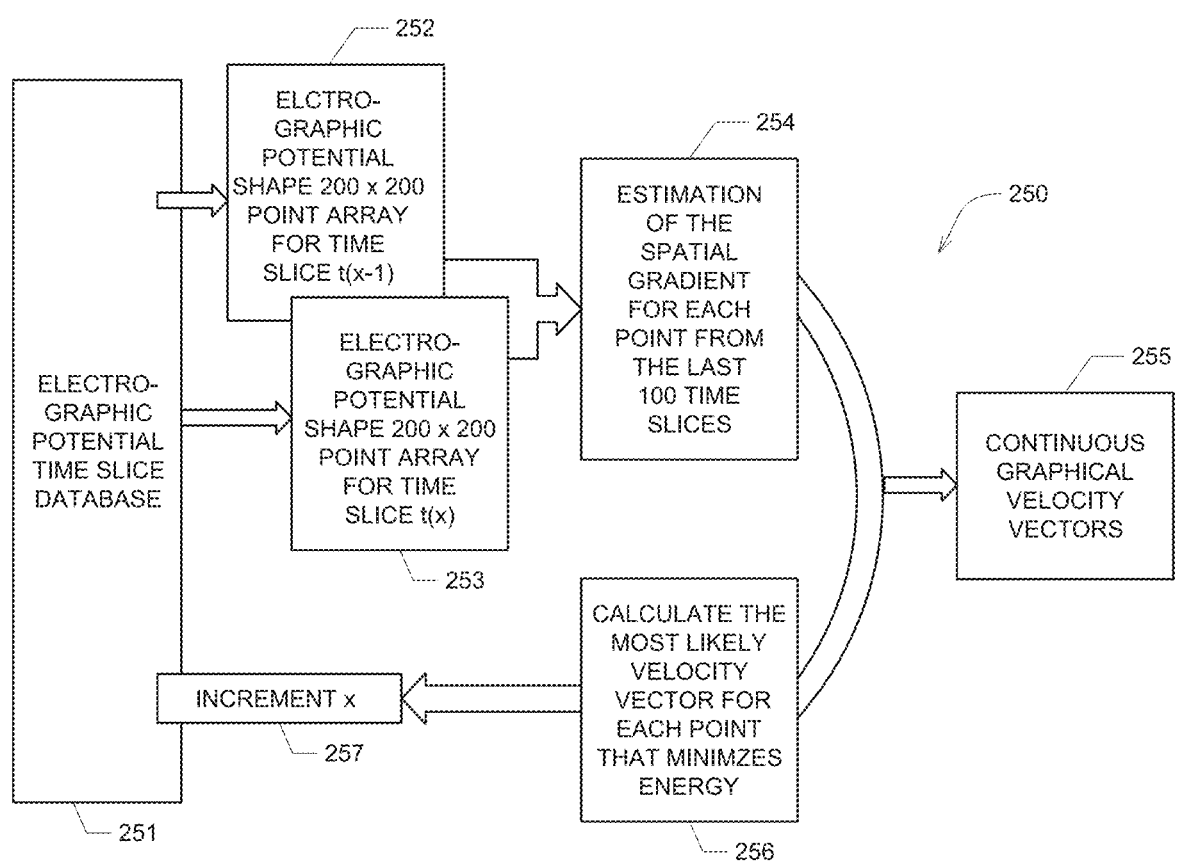

Referring now to FIGS. 6(a), 6(b) and 6(c), and with further reference to FIG. 4, there are shown some of the individual steps corresponding to the three main steps 230, 240 and 250 carried out according to one embodiment of method 200 disclosed and described herein.

FIG. 6(a) shows one embodiment of steps 202 through 212 of main step 210 of FIG. 4 ("normalize/adjust amplitudes, filter electrogram signals). In FIG. 6(a), step 202 is shown as comprising receiving a data file corresponding to the EP recording of electrogram signals from a basket or other type of EP recording catheter positioned in a patient's heart 10. The time interval over which such electrogram signals are recorded inside the patient's heart 10 may, of course, vary according to, among other things, the requirements of the diagnosis, examination, monitoring and/or treatment that is to be performed, and/or the suspected or known cardiac rhythm disorder from which the patient suffers. Illustrative, but non-limiting, examples of such time intervals range between about a second and one minute or more. Bad or poor fidelity traces or electrograms may be selectively removed or edited at this stage.

At step 204, a high-pass filter is applied to the acquired EP data to remove DC offsets, as well as other undesirable low-frequency noise. In one embodiment, a 5 Hz high-pass filter is applied, although other filters, including band-pass filters, are contemplated, including, but not limited to, 10 Hz high-pass filters, 5-20 Hz band-pass filters, and 5-50 Hz band-pass filters. Notch- and low-pass filtering may also be applied in step 204. Hanning, trapezoidal and other digital filtering and/or Fast Fourier Transform (FFT) filtering techniques may also be applied.

At step 206, an average far-field electrogram signal is generated by stacking and averaging all electrogram traces. In the case of atrial EP recordings, the resulting estimate of a far-field ventricular depolarization is subtracted from each trace individually, thereby removing or at least reducing the far-field component therefrom.

At step 208, the amplitudes of individual filtered electrogram signals are normalized with respect to a given standard deviation occurring over a predetermined time window (e.g., a moving window of 200 samples around a time value "x").

At step 212, a complete filtered sample array from the grid or basket catheter is provided as an output from first main step 210.

Referring now to FIG. 6(b), there is shown one embodiment of the second main step 230 of method 200 shown in FIG. 4 (processing amplitude-adjusted electrogram signals across the 2D or 3D representation, map or grid to generate a plurality of three-dimensional electrogram surfaces, one surface being generated for each selected or predetermined discrete time or time slice).

In FIG. 6(b), second main step 240 is shown as including steps 241 and 243, which according to one embodiment are performed in parallel or near-parallel, At step 241, digitally sampled and processed electrogram signals from step 212 of FIG. 6(a) are provided, and at step 242 an array of 200×200 empty 3D data points are generated, which correspond to the 2D or 3D representation, map or grid which is to be generated (or has already been generated). In one embodiment, such a representation, map or grid is formed by making a cylindrical projection representation, map or grid that corresponds to an approximate estimate or calculated map of the region of the patient's myocardial wall where the electrogram signals were acquired and measured (see step 243) by catheter 110. Positional data from imaging or navigation system 70 can be provided at this stage to improve the positional accuracy of the individual locations within such grid where electrogram signals were acquired. In one embodiment, for each time slice or sampled time, a Z-value or electrical potential corresponding to the normalized, adjusted and/or filtered measured voltage of each individual electrogram is assigned a location in the representation, map or grid.

At step 244, Green's function, or another suitable surface generating method, is used to generate a surface of Z-values for each time slice or sampled time (more about which is said below). In one embodiment, the surface corresponding to the Z-values is smoothed.

At step 245, the calculated surface corresponding to each time slice or sampled time is provided as an output, with, for example, a 200×200 array of smoothed data points corresponding to the smoothed surface being provided for each time slice or sampled time. Note that in some embodiments the intervals at which time slices are selected, or the individual time slices themselves, may be predetermined, or may be selected automatically or by the user.

FIG. 6(c) shows step 250 corresponding to one embodiment of the third main step of FIG. 4 (processing the plurality of three-dimensional electrogram surfaces generated through time to generate a velocity vector or other map corresponding at least partially to the 2D or 3D map) carried out, by way of non-limiting example, using optical flow analysis and estimation techniques described and disclosed elsewhere herein, and/or using the video tracking, motion capture, motion estimation, SwisTrack, particle tracking, and/or single-particle tracking methods, techniques and algorithms described and disclosed elsewhere herein. As regards optical flow analysis and estimation techniques, in FIG. 6(c), third main step 250 is shown as including step 251, which in one embodiment entails sequentially accessing the individual surfaces generated for selected time slices and/or discrete times in step 240. At steps 252 and 253, adjacent time slices are analyzed and processed sequentially. In step 254, a spatial gradient corresponding to each point of the representation, map or grid is calculated say over, for example, the last 100 time slices. At step 255, a continuous graphical output of calculated flow vectors can be provided as a real-time or near-real-time output. At step 256, the most likely flow vector magnitude (or velocity) and direction for each point that minimizes energy is calculated. At step 257, X (or time) is incremented, and the foregoing calculations are repeated and refined, the final output of which is a vector velocity map of the type shown, by way of non-limiting example, in FIGS. 5(g), 7(e), 7(i), 7(j), 7(k), 7(l), 8, 9, 10(a), 10(c), and 10(e).

FIGS. 7(a) through 7(j) show the results of processing simulated atrial cardiac rhythm disorder data using the optical flow methods and techniques described and disclosed above, where the concept of analyzing complex rotor structures was applied to a data set of simulated data. The simulated data shown in FIG. 7(a) primarily comprised stable active and passive rotors, as described in Carrick et al. in "Prospectively Quantifying the Propensity for Atrial Fibrillation: A Mechanistic Formulation," R. T. Carrick, P. S. Spector et al.; Mar. 13, 2015, PLOS ONE, DOI:10.1371, journal.pone.0118746, the entirety of which is hereby incorporated by reference herein. From Carrick, et al.'s video corresponding to the foregoing publication, and referring now to FIG. 7(a) herein, stable rotor data were recorded for a frame delineated by the indicated blue square, where there are seven rotors. The recording was accomplished using the luminance of the video frame in an 8×8 matrix with an 8-bit signal depth, thereby to simulate electrogram signal data acquired using a conventional 64-electrode 8×8 basket catheter. The overall video comprised 90 frames. All data shown in FIG. 7(a) were taken from frame 60. Signal amplitudes from frame 60 are shown in the chess field and box plots of FIGS. 7(b) and 7(c), respectively.

Figure 7A:
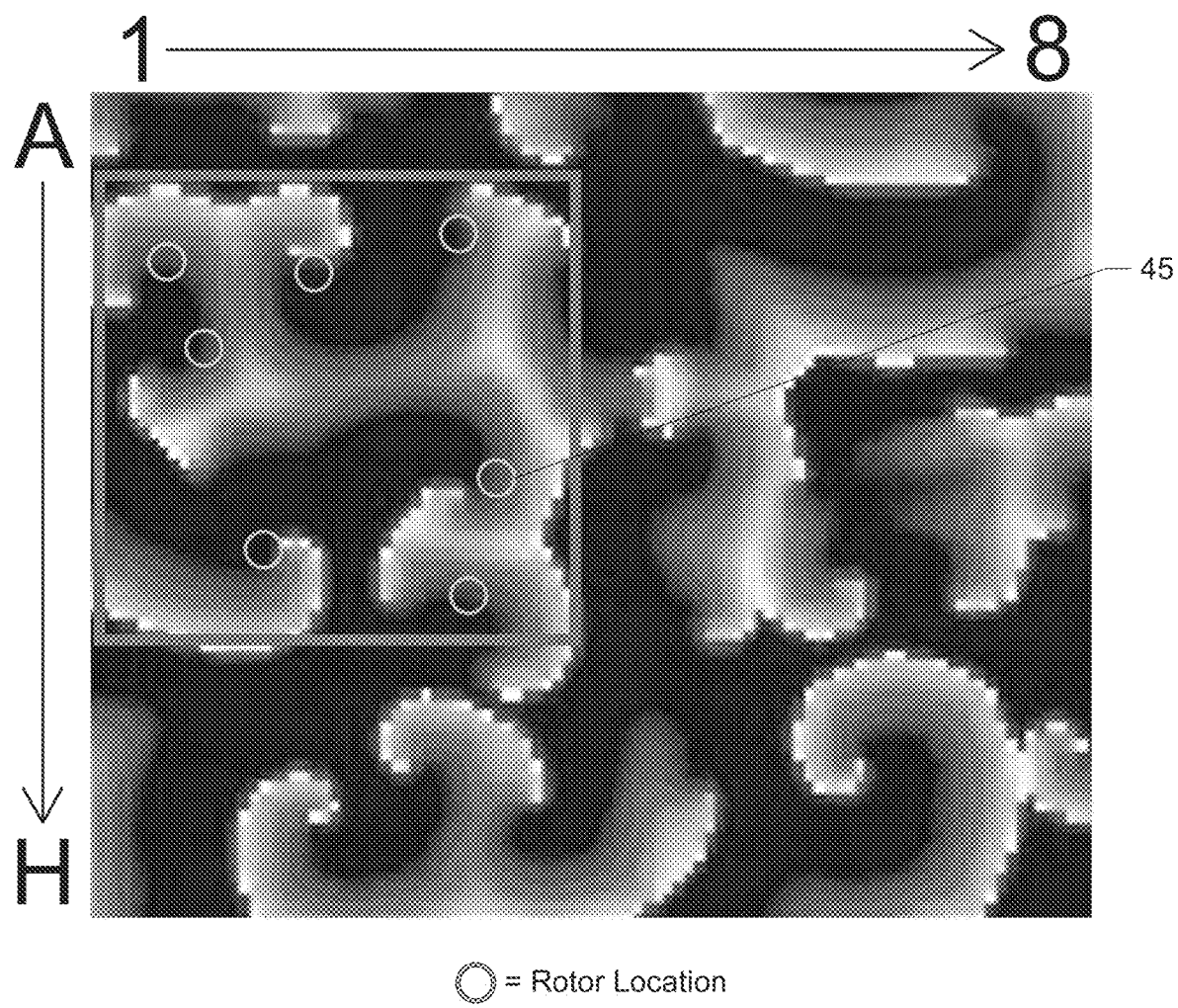
FIGS. 7(a) through 7(j) show the results of processing simulated atrial cardiac rhythm disorder data in accordance with one embodiment of method 200.

In FIG. 7(a), 7 rotors are shown as green circles 45 lying within the blue rectangle. In FIG. 7(b), a box plot of 8×8 matrix amplitudes is shown having amplitudes corresponding to frame 60. FIG. 7(d) shows the estimated wavefront or smoothed surface corresponding to frame 60. FIG. 7(e) shows the vector velocity map generated from the data corresponding to FIG. 7(a) (which was generated on the basis of all 90 frames or times slices). Reference to FIG. 7(e) shows that seven active rotors (marked as green circles 45) are apparent, as are two passive rotors (marked as red stars 46).

Figure 7B:
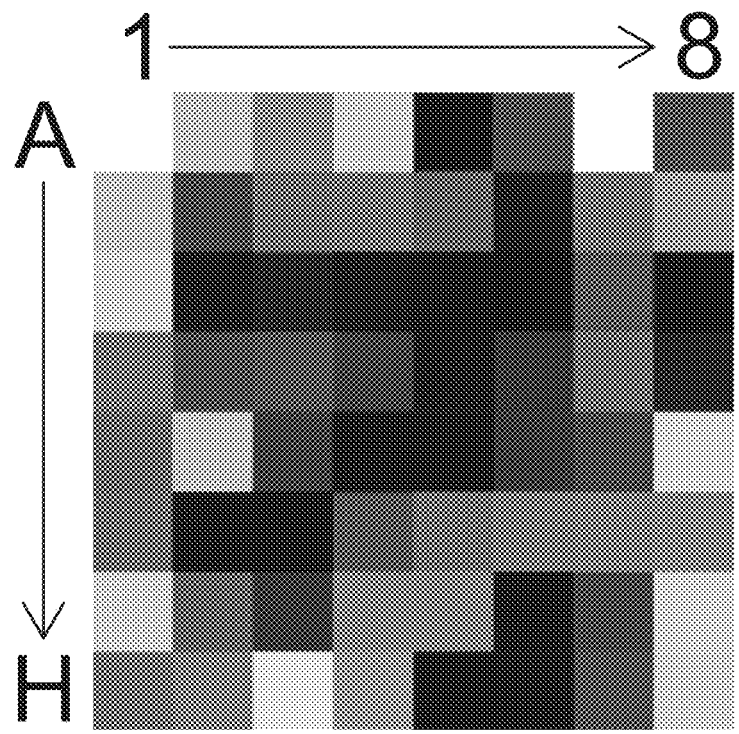
Figure 7C:
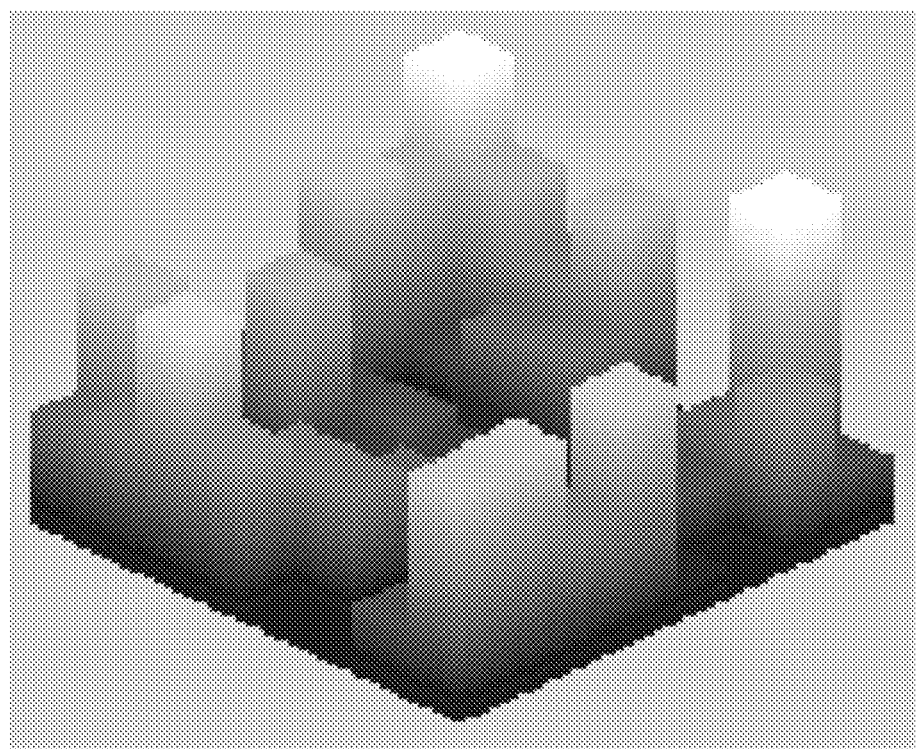
Figure 7D:
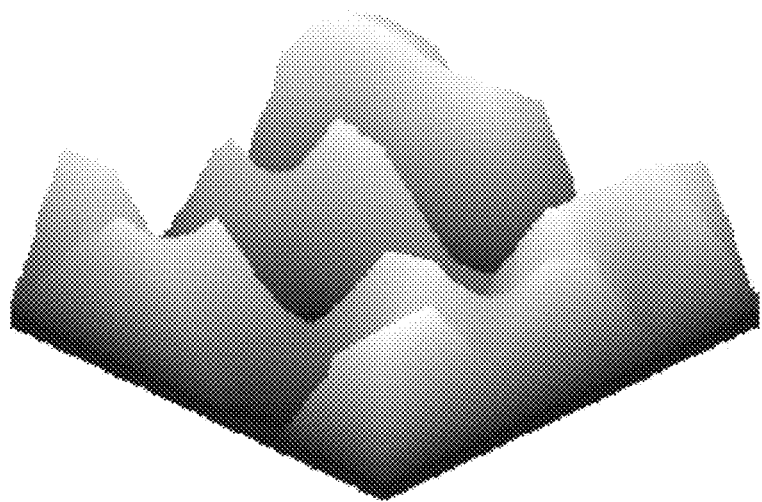
Figure 7E:
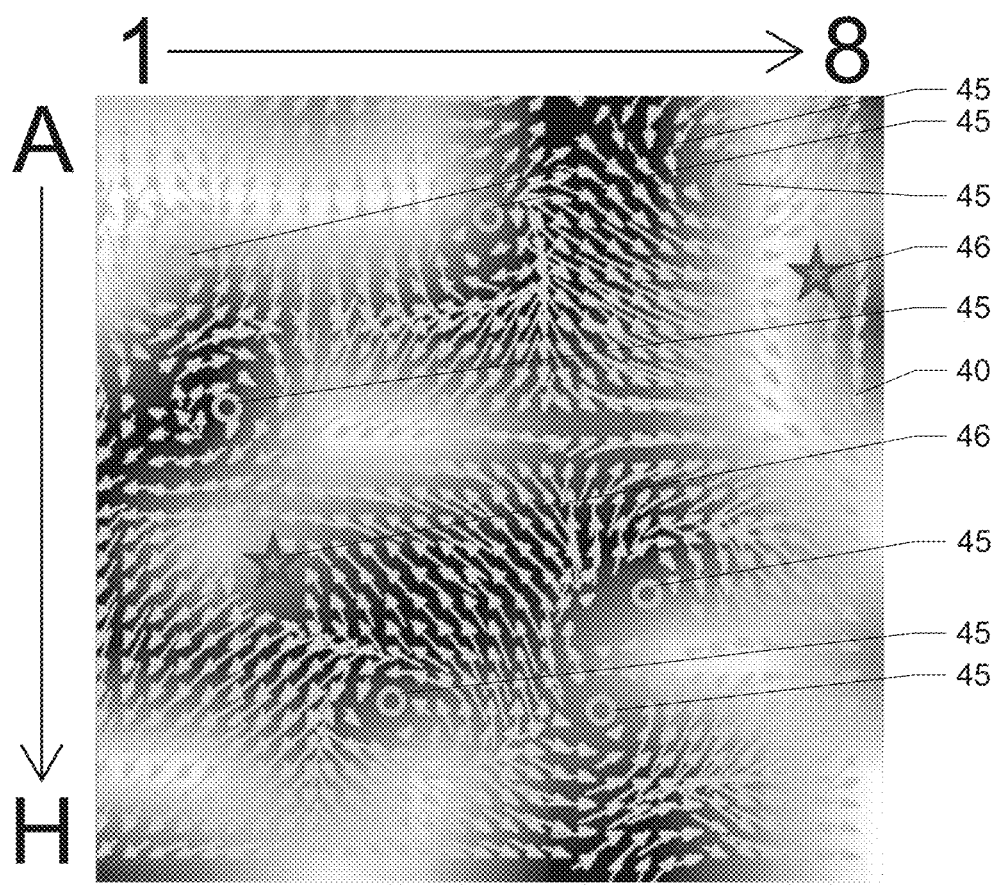

Referring now to FIGS. 7(b) and 7(c), it will be seen that the 2D and 3D box patterns shown therein provide rough estimates of the spatial wavefronts shown in FIG. 7(a). In FIG. 7(d), however, the original data shown in FIG. 7(a) are reproduced fairly accurately, and also provide a good input to the vector velocity map of FIG. 7(e) (which nicely reveals the 7 active rotors visible in FIG. 7(a)). The yellow vector arrows in FIG. 7(e) not only show the rotational centers of the individual rotors, but also show that active rotors indicated by green circles are driving sources of the wave fronts because the calculated vectors of the active rotors always point centrifugally away from the rotor centers. In contrast, the two red stars shown in FIG. 7(e) indicate the locations of passive rotors or flow turbulences that, while circular in shape, have centripetal vector directions to at least on one side of the rotor centers associated therewith.

Discrimination between active and passive rotors is critical to making proper therapeutic decisions regarding the delivery of ablation therapy, which should only target structures underlying the drivers of atrial fibrillation (namely, active rotors only, and not passive rotors).

Next, the effects of typical artifact disturbances on the signals of the 64 channels of data shown In FIGS. 7(a) through 7(d) were determined by introducing simulated variable amplitude DC-offset noise and artifacts into the electrogram signals. The objective was to test the extent to which such artifacts and noise might impair or disable the ability of method 200 to detect rotors in the data.

Figure 7F:
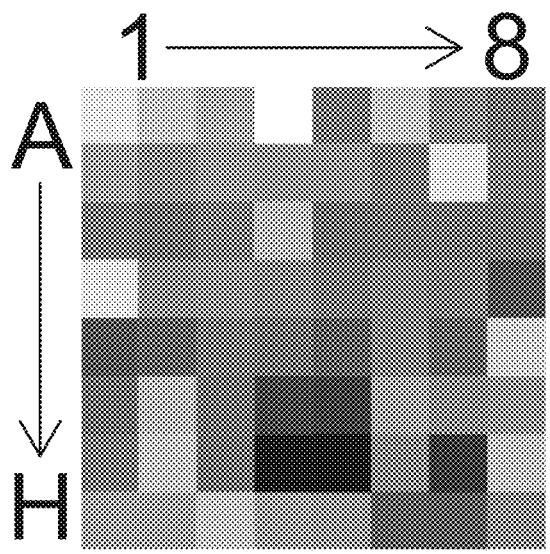
Figure 7G:
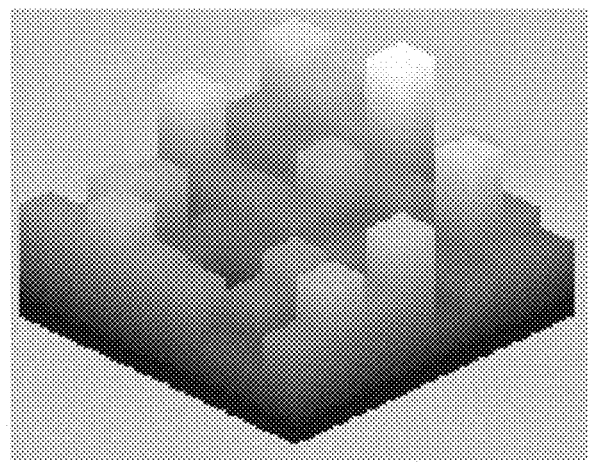
Figure 7H:
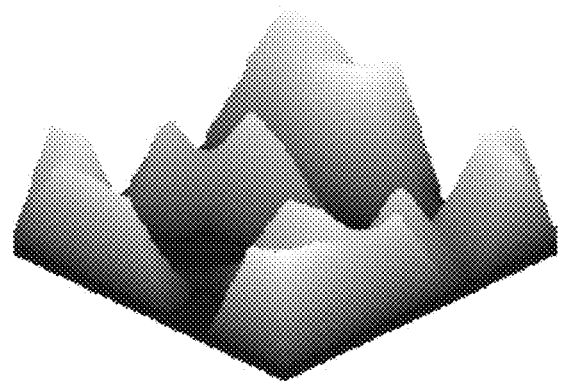

FIGS. 7(f) and 7(g) show the same box plot data as FIGS. 7(b) and 7(c), respectively, but with the foregoing-described superimposed and introduced artifacts. That is, FIGS. 7(f) and 7(g) show the chess field and box plots of the disturbed electrogram signals corresponding to frame 60. After filtering and normalization in step 210, the original rotor structure shown in FIG. 7(a) once again becomes visible in FIG. 7(h) following completion of the main second step 240 of the method.

Figure 7I:
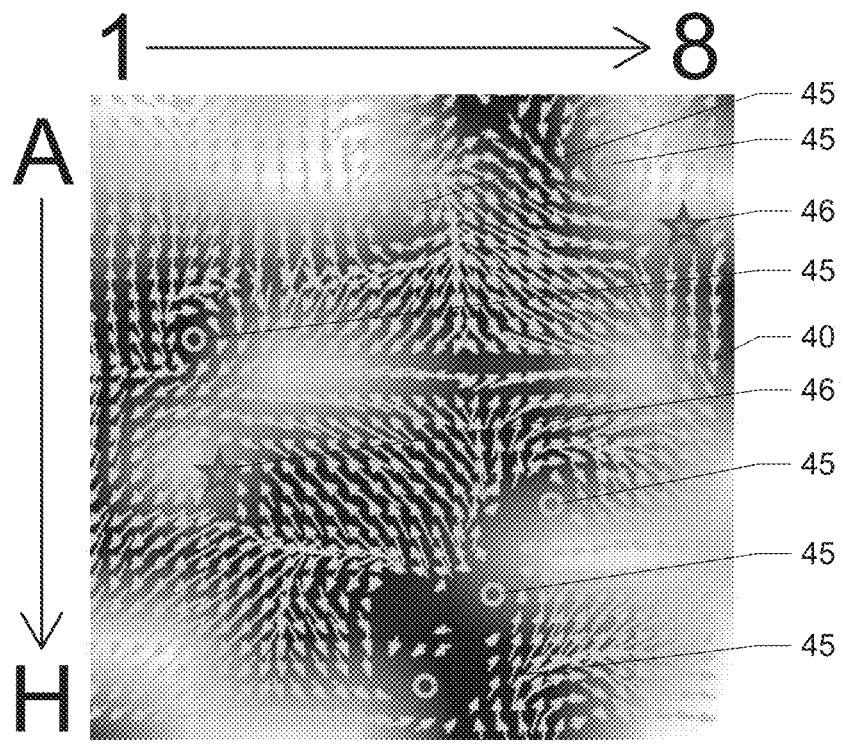

Upon applying smoothed surface calculations and fitting (as shown in FIG. 7(i)), method 200 is seen to detect only five of the seven active rotors shown in FIG. 7(a). One additional active rotor, however, was detected at a different location (see FIG. 7(i)).

Figure 7J:
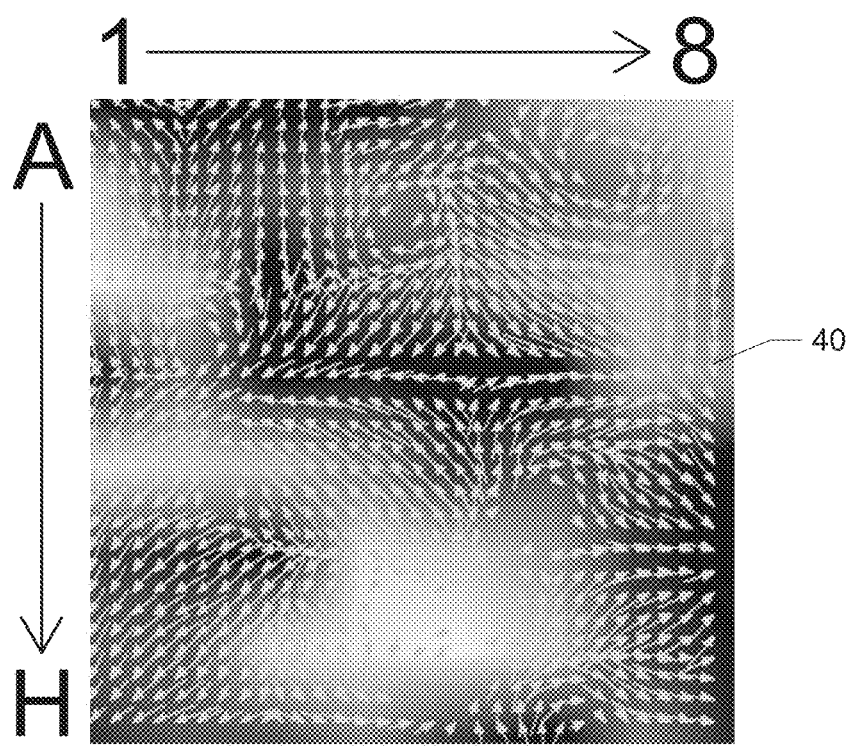

The largest variation in results was seen at positions where the introduction of the artifacts and noise reduced relative amplitude values by the greatest amount, as indicated by the white areas shown in FIG. 7(j). The white areas shown in FIG. 7(j) were generated by using the sliding-window amplitude-adjusted electrogram signal techniques described above, where electrograms processed using sliding-window techniques were used to generate the image background (including the white areas) shown in the velocity vector map of FIG. 7(j). The white areas in FIG. 7(j) thus correspond to low amplitude areas potentially indicative of valve defects or artifacts, loose electrode contact, and/or areas of fibrosis in the patient's myocardium. It is important to point out that the low-amplitude areas shown in white in the various velocity vector maps presented herein are not calculated using Green's function or optical flow data processing techniques. Instead, and as described above, these low-amplitude regions or areas may be detected by assessing the relative amplitudes of electrogram signals in step 210.

In the white areas of FIG. 7(j), the resulting velocity vector map shows that the active rotors indicated therein are slightly moved closer together than in FIG. 7(i), and on the left center side of FIG. 7(j) two rotors appearing in FIG. 7(i) are revealed as a single active rotor n FIG. 7(j). FIGS. 7(a) through 7(j) show that there are limits to the resolution that can be achieved using a conventional 8×8 array of sensing electrodes in a basket catheter having standard inter-electrode spacing. Thus, higher electrode densities and more recording channels could increase the resolution and accuracy of the results obtained using method 200.

After confirming that method 200 was capable of detecting complex rotor structures accurately in a patient's myocardium—even in the presence of strong artifacts and noise—method 200 was applied to different time portions of the actual patient data shown in FIG. 5(b) so as to test further the method's efficacy and accuracy. A velocity vector map corresponding to data acquired between 4,700 milliseconds and 5,100 milliseconds in the original EP recording of FIG. 5(b) is shown in FIG. 8(a).

Figure 8A:
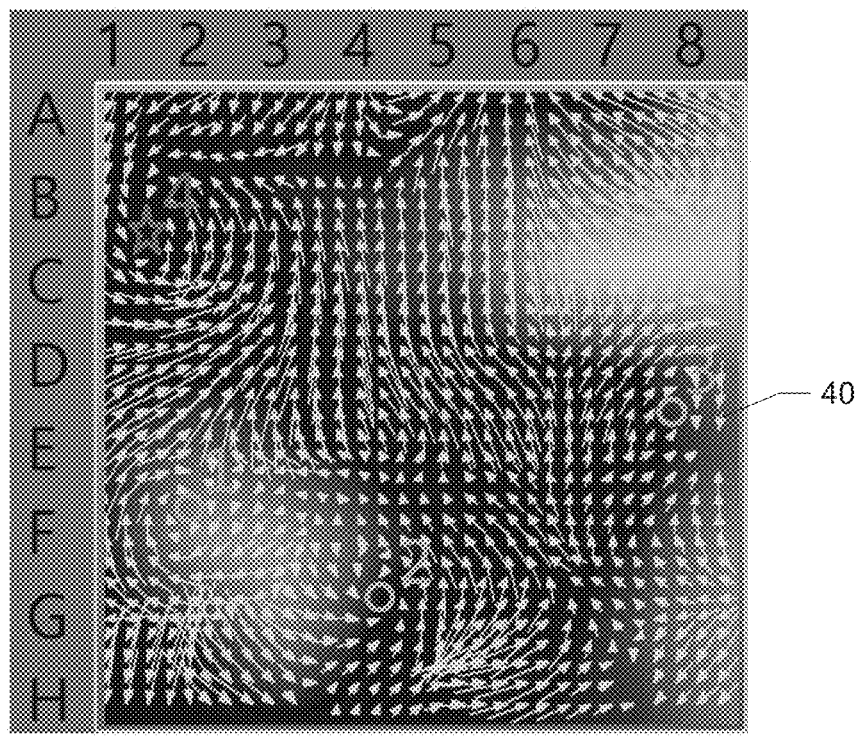
FIGS. 8(a) and 8(b) show velocity vector maps generated from actual patient data using different time windows and method 200.

As shown in FIG. 8(a), four rotors indicated by circles 1, 2 and 3 and a star 4 were detected. Circles 1 and 2 in FIG. 8(a) appear to denote active rotors that are interacting with one another. Circle (3) in FIG. 8(a) may be an active rotor, but exhibits some centripetal components. Star 4 in FIG. 8(a) clearly corresponds to a passive rotor. Next, a velocity vector map corresponding to the same data set for data acquired between samples 0 seconds and 400 milliseconds was generated, the results of which are shown in FIG. 8(b).

Figure 8B:
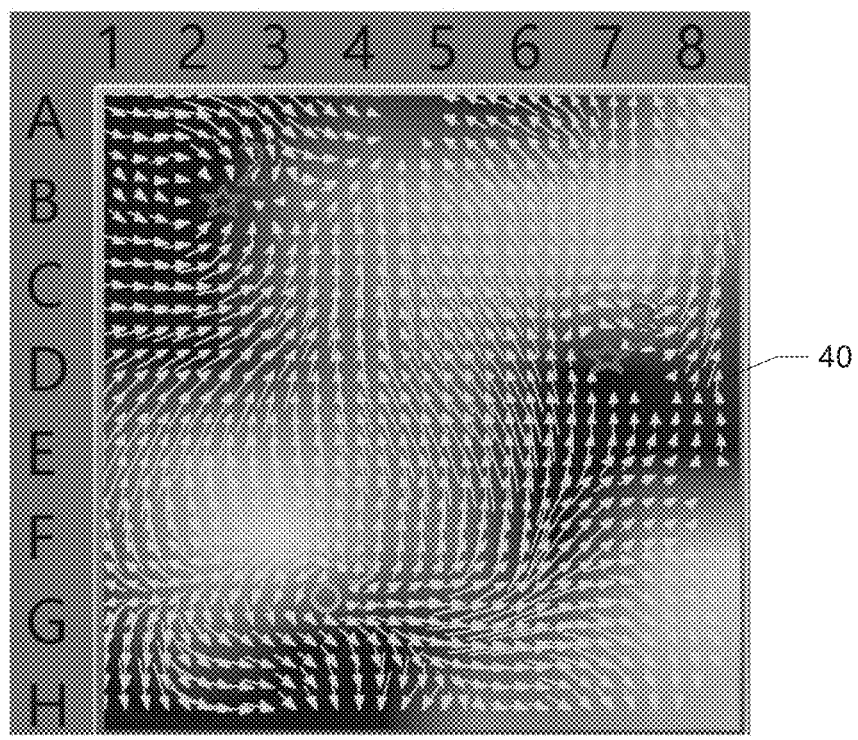

Differences between the results shown in FIGS. 8(a) and 8(b) permit a deeper insight into the true rotor structure of this patient's myocardium, as best shown in FIG. 8(b). In the earlier time interval (0 msec. to 400 msec.) of FIG. 8(b), the two associated rotors 1 and 2 shown in FIG. 8(a) are not yet active, while there is only a single active rotor 5 in FIG. 8(b) located between the positions of rotors 1 and 2 shown in FIG. 8(a). Rotors 1 and 2 in FIG. 8(b) show up at slightly different positions, but now appear clearly as passive rotors representing likely turbulences generated at the border of a mitral valve artifact.

Thus, a health care professional can select differing time windows over which to apply method 200 to an EP mapping data set as a means of gaining a better understanding of the behavior of active and passive rotors, fibrotic regions, areas affected by valve defects or artifacts, breakthrough points and areas or defects that are at work in the patient's myocardium. The velocity vector or other maps generated by method 200 permit a health care professional to identify such cardiac rhythm disorders in a patient's myocardium with a degree of precision and accuracy that has heretofore not been possible using conventional EP mapping and intravascular basket or spline catheter devices and methods.

Figure 9:
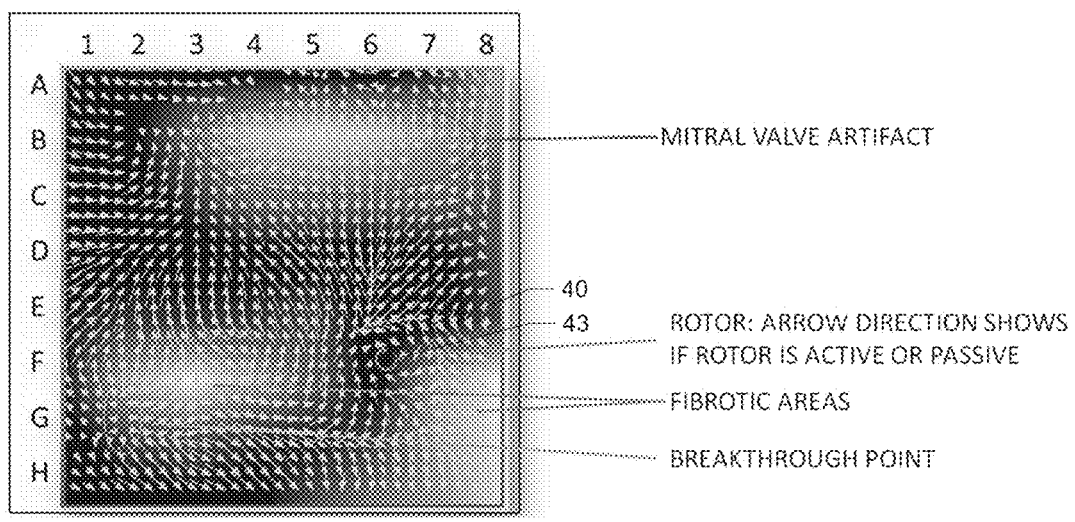
FIG. 9 shows another vector velocity map generated from actual patient data using of method 200.

Referring now to FIG. 9, there is shown another example of a vector velocity map generated from actual patient data using method 200. In FIG. 9, arrows 40 correspond to action potential wavefront velocity vectors, which as illustrated have differing magnitudes and directions associated herewith. As shown in FIG. 9, various cardiac rhythm defects and disorders become apparent as a result of the generated vector velocity map. The defects and disorders revealed by the vector velocity map of FIG. 9 include an active rotor (where the active rotor propagation direction is indicated in the bottom right of FIG. 9 by green circle 43 rotating in a clockwise or centrifugal direction), a breakthrough point in the bottom left of FIG. 9, fibrotic areas indicted by low-amplitude white areas in the lower portion of FIG. 9, and a mitral valve defect indicted by the white area in the upper portion of FIG. 9.

Figure 10A:
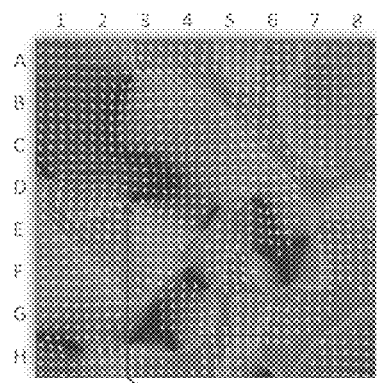
FIGS. 10(a) through 10(d) show further results obtained using actual patient data.
Figure 10B:
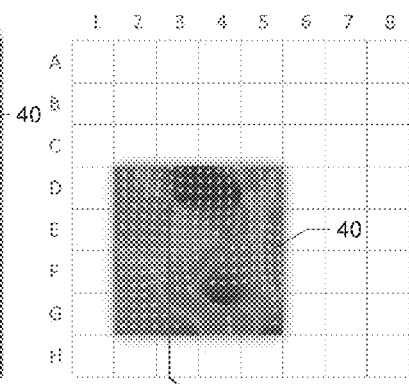
Figure 10C:
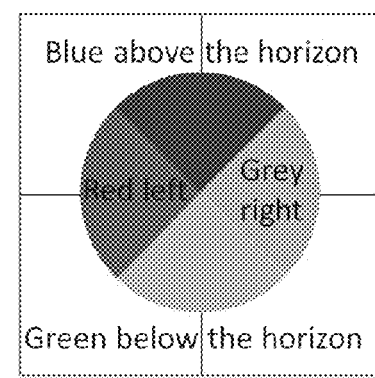
Figure 10D:
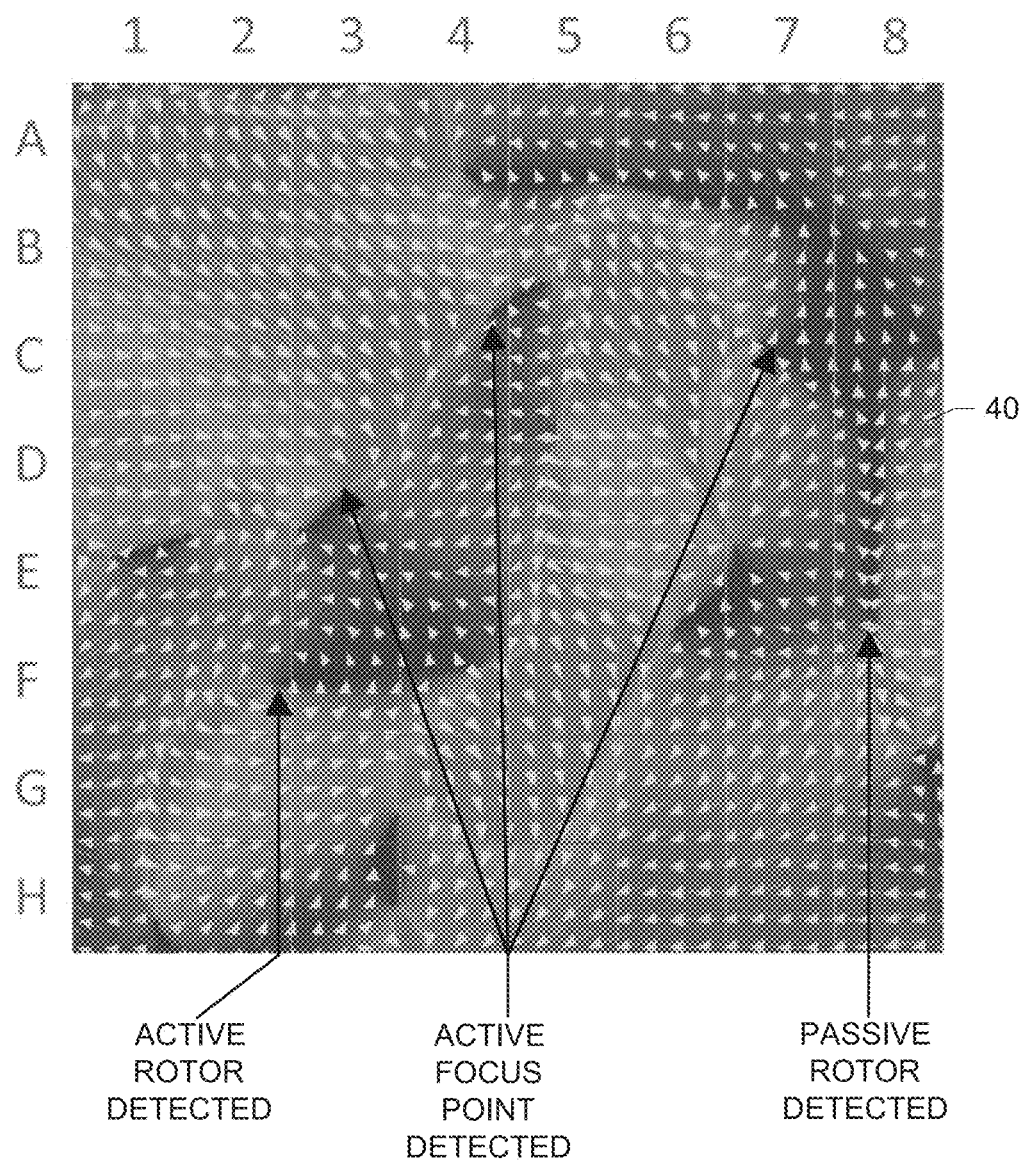

Referring now to FIGS. 10(a) through 10(d), there are shown further results obtained using actual patient data. The raw data corresponding to FIGS. 10(a) through 10(d) were acquired from a single patient's right atrium using a 64-electrode basket catheter and corresponding EP mapping/recording system. Data were acquired at a 1 millisecond rate over a time period of 60 seconds in all 64 channels. FIGS. 10(a) and 10(b) correspond to one selected 2 second time window, and FIG. 10(d) corresponds to another time window from the same data set. FIG. 10(d) shows the color-schemes employed in FIGS. 10(a), 10(b), and 10(d).

The vector velocity map of FIG. 10(a) generated using method 200 clearly reveals an active rotor located at chess board position D/E, 2/3. The vector velocity map of FIG. 10(b) was also generated using method 200, but using data acquired from only 16 electrodes in grid D –G, 2 –5. As shown in FIG. 10(b), the active rotor evident in FIG. 10(a) is nearly equally evident in FIG. 10(b) despite the significantly more sparse data grid employed to produce the velocity vector map. These remarkable results obtained using a sparse electrode grid are due in large part to the robustness, stability and accuracy of method 200, as it has been applied to electrographical flow problems.

FIG. 10(d) shows another example of results obtained using method 200 and EP mapping data obtained from the same patient as in FIGS. 10(a) and 10(b), but over a different time window. Note also that FIG. 10(d) shows that method 200 has successfully detected one active rotor (at chess board location F2/3), three active focus points, and one passive rotor (at chess board location F8).

It will now be seen that method 200 provides not only rotational direction information, but in at least some embodiments can also provide high-resolution spatial information regarding the presence and location of rotors despite the use of sparse electrode grid spacing. Rotors can also move over time in a patient's myocardium, even during the time interval over which EP mapping is being carried out. The increased spatial and temporal resolution of method 200 permits such shifts in rotor location to be detected.

In some embodiments, and as described above, multiple or different types of EP mapping and ablation catheters can be used sequentially or at the same time to diagnose and/or treat the patient. For example, a 64-electrode CONSTELLATION basket catheter can be used for EP mapping in conjunction with a PENTARAY16- or 20-electrode EP mapping catheter, where the PENTARAY EP mapping catheter is used to zero in on, and provide fine detail regarding, a particular region of the patient's myocardium that the basket catheter has revealed as the location of a source of a cardiac rhythm disorder or irregularity. In addition, catheter 110 or any other EP mapping catheter used in system 100 may be configured to provide ablation therapy (in addition to EP mapping functionality). The various catheters employed in system 100 may also include navigation elements, coils, markers and/or electrodes so that the precise positions of the sensing, pacing and/or ablation electrodes inside the patient's heart 10 are known. Navigational data can be employed by computer 300 in method 200 to provide enhanced estimates of the locations of the electrodes in the representations, maps or grids generated thereby, which in turn increases the accuracy and efficacy of the resulting velocity vector maps generated in method 200.

In another embodiment, computing device/system 300 is operably connected to a storage medium such as a hard drive or non-volatile memory located in, or operably connected to, data acquisition device 140, where computing device 300 is configured to trigger an external switch operably connected to data acquisition device 140 which permits the upload of conditioned electrogram signal data from data acquisition device 140 to computing device 300. According to such a configuration, computing device 300 and data acquisition device 140 can remain galvanically isolated from one another, and the need to physically swap USB memory sticks between data acquisition device 140 and computing device 300 is eliminated. This, in turn, permits system 100 to operate more efficiently and quickly, and to provide vector velocity maps to the health care professional in near-real-time while the EP mapping procedure is being carried out within the patient's heart 10.

In method 200, electrogram signals and processed data may be delivered or communicated to system 100, e.g., via a data carrier, after they have been acquired by the electrodes and stored for later processing. The various steps recited in the claims, and the sub-steps recited in each step, need not necessarily be carried out in the precise order in which they are recited.

The various systems, devices, components and methods described and disclosed herein may also be adapted and configured for use in electrophysiological mapping applications other than those involving the interior of a patient's heart, more about which is said below. These alternative applications can include internal or external EP mapping and diagnosis of a patient's epicardium or other portions of the patient's heart, a patient's spinal cord or other nerves, or a patient's brain or portions thereof.

Referring now to FIGS. 1(a) through 10(d), and also referring to the foregoing portions of the specification, it will now be seen that various embodiments of EGF and other optical flow, flow, tracking, capture, and flow estimation techniques, methods, systems, devices, and components are described and disclosed herein, which can be employed to reveal the locations of sources of cardiac rhythm disorders in a patient's heart, including, but not limited to, rotors and sources that cause or contribute to AF.

Moreover, note that the various data processing steps described and disclosed above explicitly in connection with FIGS. 1(a) through 10(d) in furtherance of providing useful EGF results can be carried out using numerous permutations, combinations, variations, adaptations, and modifications, and signal conditioning and/or filtering techniques, which though they may not be specifically or explicitly mentioned in the specification hereof, are nonetheless contemplated and fall within the spirit and scope of the various inventions described and disclosed herein. By way of example, a variety of two-dimensional digital filtering, image filtering, and/or digital signal processing (DSP) techniques are also contemplated that may be employed in one or more the data conditioning and/or processing steps disclosed and described above, such as phase correlation, block-based methods, motion estimation, measuring visual motion, autocorrelation, cross-correlation, convolution, deconvolution, adaptive deconvolution, wavelet deconvolution, source deconvolution, and/or median filtering. By way of further example, at least some of these alternative signal processing techniques may be used to effect or aid in surface and/or data grid processing steps, and/or optical flow processing steps.

There are now described in greater detail various embodiments of, and details concerning, electrographic flow (EGF) and other types of analysis, which broadly may employ some or many of the techniques and concepts described above. EGF analysis and mapping, and other suitable techniques described above, provide novel methods to identify Atrial Fibrillation (AF) drivers based on modeling electrical potential surfaces and subsequent flow analysis. Sources of excitation during AF can be characterized and monitored. Some of the EGF and other flow and tracking embodiments described and disclosed below employ some of the data acquisition, processing and interpretation techniques described above, which are applied to the problem of efficiently and cost-effectively screening patients for atrial fibrillation without undertaking costly invasive medical procedures, such as EP mapping using intra-cardiac basket catheters.

Recent work in the field of atrial fibrillation using EGF and other techniques, conducted to further validate and test the various inventions described and disclosed herein, has revealed highly useful results. Described below in detail are recent results obtained using raw intra-cardiac EP mapping data that were originally obtained using conventional EP mapping techniques and systems (i.e., the TOPERA® cardiac arrhythmia mapping system), but which were subsequently processed and analyzed using the novel EGF techniques disclosed and described herein (hereafter "the EGF studies"). The original intra-cardiac EP mapping data were acquired from 108 patients in three different studies in hospitals located in Hamburg, Germany, Berlin, Germany, and Rotterdam, The Netherlands, using a conventional basket catheter system; namely, the aforementioned TOPERA system utilizing FIRMap catheters and RhythmView workstations. In the original TOPERA-based studies, focal impulse and rotor-mapping (FIRM) were performed in addition to pulmonary vein isolation. In the studies, one-minute epochs of unipolar electrograms were recorded using a 64-pole FIRMap basket catheter in both atria.

The aim of the retrospective EGF-based studies described herein was to evaluate the correlation between EGF velocities around given sources and their corresponding spatial variabilities (SV) and stabilities (SST). SST was calculated as a percentage of time over which a source was detected. AF sources identified with EGF mapping showed a wide range of SV and SST. Less stable AF sources with high spatial variability showed reduced excitation propagation velocity, while very stable AF sources displayed a high average velocity in their vicinity. Catheter ablation was shown to reduce the stability of sources and velocities, suggesting a role of these parameters in guidance of ablation.

More about these retrospective EGF studies is said below. However, some details regarding recent EGF-based studies may be found in the following publications:
(a) "Velocity characteristics of atrial fibrillation sources determined by electrographic flow mapping before and after catheter ablation" to Bellmann et al., International Journal of Cardiology, Jul. 1, 2019, Volume 286, Pages 56-60, DOI: https://doi.org/10.1016/j.ijcard.2019.02.006 (hereafter "the Bellman I publication);
(b) Identification of active atrial fibrillation sources and their discrimination from passive rotors using electrographical flow mapping, Clinical Research in Cardiology, May 2018, DOI: 10.1007/s00392-018-1274-7 (hereafter "the Bellman H publication), and
(c) "Electrographic Flow Mapping—A Novel Technology for Endocardial Driver Identification in Patients with Persistent Atrial Fibrillation" to Bellmann et al., Poster Session IV, C-PO04-76, S356 Heart Rhythm, Vol. 14, No. 5, May Supplement 2017 (hereafter "the Bellman III publication);

Each of the foregoing Bellmann I, Bellmann II, and Bellmann III publications is hereby incorporated by reference herein, each in its respective entirety.

The EGF studies described and disclosed herein show that EGF techniques and analysis can be used as a powerful tool to characterize AF sources, and to sort patients into different types; namely, A-type patients, B-type patients, and C-type patients. A- and B-type patients are characterized by well-defined and steady EGF patterns and sources in the atria, which in some embodiments, and as described above, can be presented as 2D or 3D EGF maps. Contrariwise, C-type patients exhibit chaotic EGF patterns that do not exhibit stationary or stable sources in the atria. In the EGF studies, FIRM data from 108 patients with known outcomes were processed and analyzed using EGF technology.

The best predictor for outcome (freedom from AF) turns out to be EGF Source Activity at the end of each procedure (Final Activity). Source Activity is defined as the percent of active time per minute (or other suitable unit of time) that a leading source has been detected. EGF steadiness, E/s (or electrodes/second), is a parameter relevant for the characterization of flow, and therefore finds use in patient stratification or classification (e.g., into A, B, or C types). Flow angle stability (FAS) over time, or flow angle stability per suitable unit of time, is another parameter that can be used to evaluate outcome or freedom from AF, and has proved to be a more useful predictor of outcome (freedom from AF) than steadiness or E/s.

EGF Source Activity, and how it is computed, requires no further explication. Obviously, different time periods can be used to estimate EGF Activity. Source Activity is the percentage of time a source is detectable. Final activity is the activity that is measured after all intra-cardiac ablation and PVI procedures have been completed.

Steadiness (or E/s) is essentially a measure of velocity (or the rate at which a detected signal moves from one electrode to another), and the consistency or steadiness thereof. If E/s is low, then detected flow signals are low in amplitude or inconsistent. If E/s is high, then detected flow signals are strong. Examples of low E/s values range between about 0 and about 5. Examples of high E/s values are those greater than about 10 or 15.

Flow angle stability (FAS) is computed by determining, for a given pixel or point in a flow or vector field, the angular displacement that occurs between successive time samples for the same pixel or point, over a given recording period (e.g., one minute, with each pixel being sampled, e.g. at a rate of 1 msec.). The maximum angular displacement that can occur between successive time samples in a sequence of vector fields, given a reference direction, is equal to $\pi$ radians (or 180 degrees). FAS can be computed for each pixel or point in a flow field to produce an FAS map. Some examples of FAS values produced using 1-minute recordings and 1 msec. sample rates are: (a) about 0 to about $\pi/4$ for a high FAS (i.e., a very stable source that does not move much), and (b) about $\pi/4$ to about $\pi/2$ for an unstable, chaotic, or highly variable source.

EGF Activity levels combined with, for example, one or more of the number detected sources, the activity of detected sources, the flow angle stability of detected sources, and the steadiness of detected sources permits a classification of patients into three types (A, B and C). A- and B-type patients (e.g., 56% of analyzed patient population) significantly benefited from source ablation in addition to PVI, and exhibited an increase in freedom from AF after 12 months, rising from 19% to 81% (p value=0.0000016), C-type patients (44% of analyzed patient population) showed no significant source ablation benefit after successful PVI. Moreover, in C-type patients, source ablation had no significant effect, and on average these patients exhibited 73% freedom from AF after 12 months. In other words, there is no need or benefit for most C-type patients to undergo either: (a) invasive intra-cardiac basket catheter EP mapping procedures, or (b) intra-cardiac ablation procedures (more about which is said below).

The EGF studies and the corresponding EGF technology employed therein are now described in further detail.

Figure 11A:
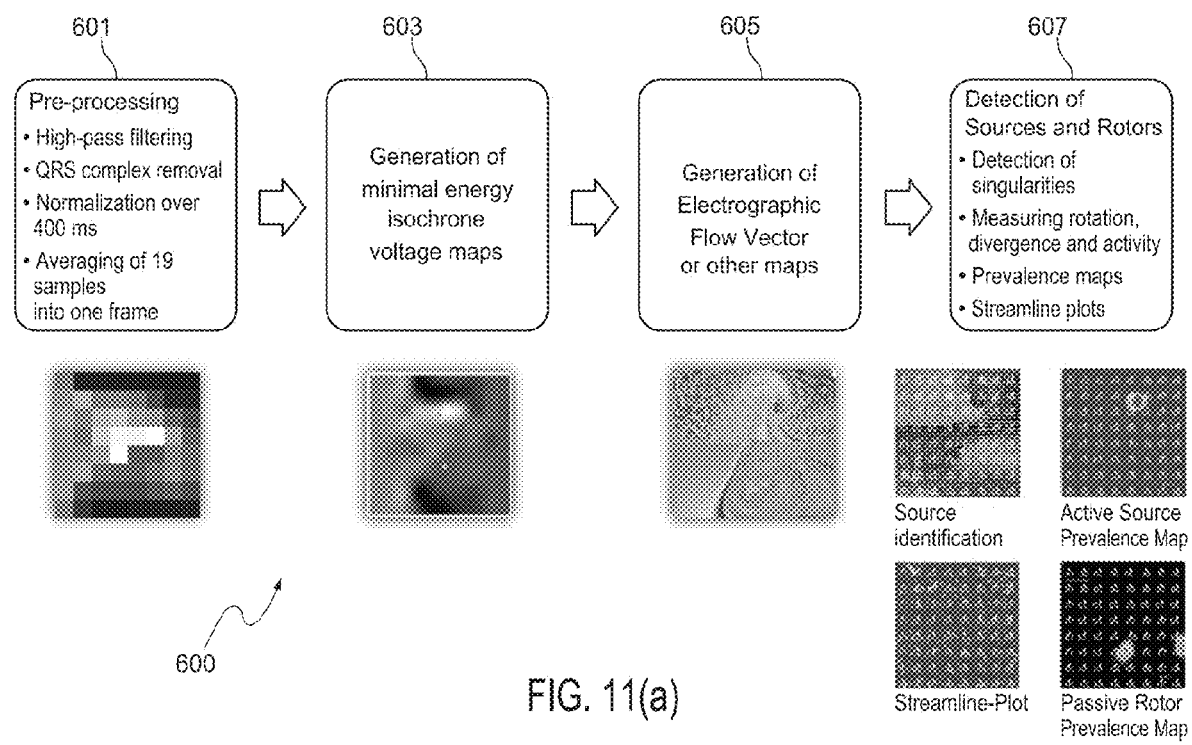
FIG. 11(a) shows one embodiment of an example of EGF data processing and analysis 600.

FIG. 11(a) shows one embodiment of an example of EGF data processing and analysis 600, as will become apparent after having read and understood the preceding portions of the specification and accompanying Figures, and with further reference to the portions of the specification and accompanying Figures that follow. Method 600 of FIG. 11(a) was employed in the EGF studies. Moving from left to right in FIG. 11(a), at step 601 intra-cardiac electrogram signals are first pre-processed, and as described above in detail, minimal energy isochrones voltage maps are generated at step 603. Next electrographic flow vector flow maps are generated at step 605, followed by the detection of sources and rotors at step 607, which as shown in FIG. 11(a) can involve, by way of non-limiting example, the generation of source identification maps, active source prevalence maps, streamline-plot maps, and/or passive rotor prevalence maps. Although FIGS. 11(a) through 11(h) refer to and are based upon intra-cardiac basket catheter data acquired during the aforementioned EGF studies (and subsequent corresponding EGF data processing and analysis), the same or similar techniques can also be applied to electrograms acquired from at or near the external body surface of a patient (more about which is said below).

Figure 11B:
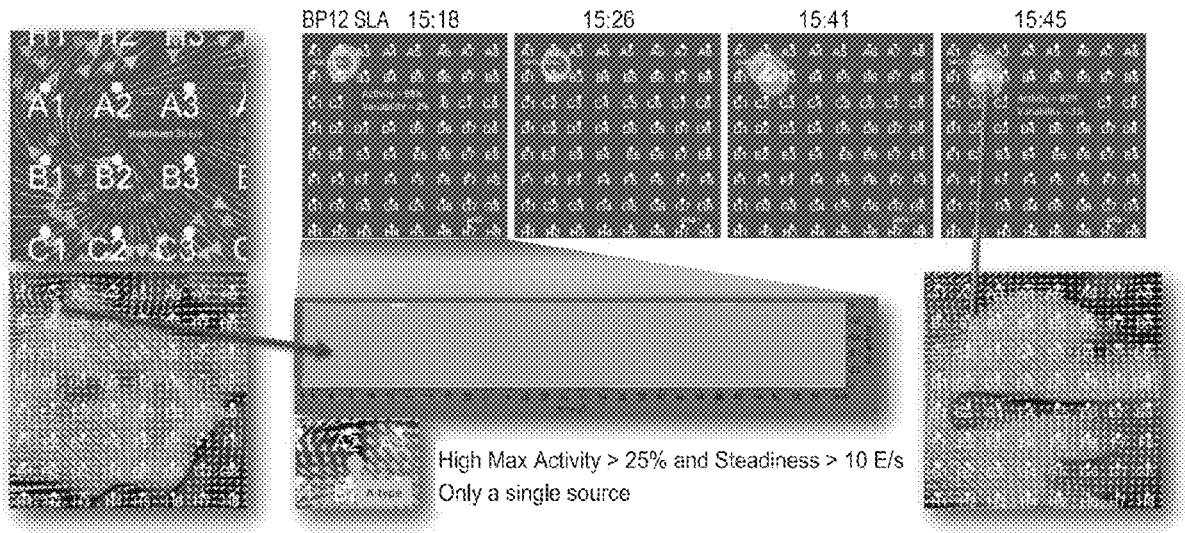
FIG. 11(b) shows EGF results obtained in a Type-A patient before and after intra-cardiac ablation has been performed on a detected leading source.

FIG. 11(b) shows EGF results obtained in a Type-A patient involved in the studies before and after intra-cardiac ablation has been performed on the detected leading source. As shown in FIG. 11(b), activity has dropped from 41.7% to 15.8%, and steadiness has decreased from 19 E/s to 11 E/s post-ablation. In other words, the detected leading source has essentially been neutralized and eliminated by ablation, as shown by the displayed EGF results.

Figure 11C:
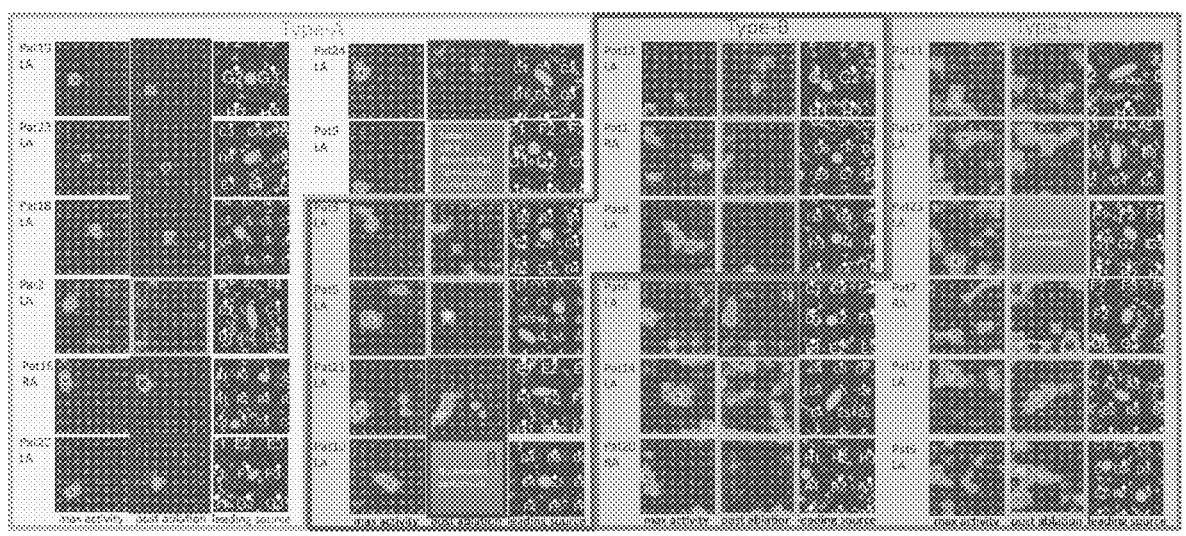
FIG. 11(c) shows some EGF results obtained in a pilot study.

FIG. 11(c) shows some EGF results obtained in a pilot study forming a portion of the EGF studies that was conducted in Hamburg. In the pilot study, 24 patients were sorted and classified into A-, B- and C-type groups according to Steadiness (left panel) and Final Activity (right panel), which both showed clear correlations with outcome. In one embodiment, steadiness means EGF velocity in the source vicinity during an active 2s segment: other such active segments are also contemplated, including, but not limited to, about 1 second, about 2 seconds, about 3, seconds, about 4 seconds, about 5 seconds, between about 0.5 seconds and about 10 seconds, and between about 1 second and about 5 seconds. Spatial Variability or Steadiness means surface coverage of 80% of a detected activity over a one-minute time period. Other such time periods for detected activities are contemplated, including, but not limited to, about 10 seconds, about 20 seconds, about 30 seconds, about 40 seconds, about 50 seconds, about 70 seconds, about 80 seconds, about 90 seconds, between about 20 seconds and about 3 minutes, between about 30 seconds and about 2 minutes, and between about 30 seconds and about 90 seconds. Changing the selected active segment percentages and/or the detected activity time periods can also lead to changes in calculated Steadiness and Final Activity values. A-type patients exhibited Final Activity z 25%, (the highest specificity for recurrence). B-type patients exhibited Steadiness ≤10.0 E/s (the highest sensitivity for recurrence). These threshold values were subsequently confirmed in validation studies conducted with 78 further patients from Berlin and Rotterdam (as described above, and which also comprised portions of the EGF studies).

FIGS. 19 and 20 set forth further data and statistics regarding the pilot study conducted in Hamburg. FIG. 19 shows the recurrence of AF or AT after 3, 6 or 12 months, where the symbol "*" denotes paroxysmal AF, and sources in the PV were ablated by PVI to termination. FIG. 20 shows freedom from AF or AT after 3, 6 and 12 months, where the symbol also "*" denotes paroxysmal AF, and where sources in the PV were also ablated by PVI to termination.

In the validation studies conducted with 78 patients in Berlin and Rotterdam, patients were once again sorted and classified according to Final Activity, and the following results were obtained:
Final activity >25%;
19% free of AF after 3+6+12 m
53% free of AF after 12 m.
Final activity 25% to 20%:
55% free of AF after 3+6+12 m
80% free of AF after 12 m
(p=0.04).
Final activity <20%:
77% free of AF after 3+6+12 m
95% free of AF after 12 m
(p=0.0007).

Figure 22:
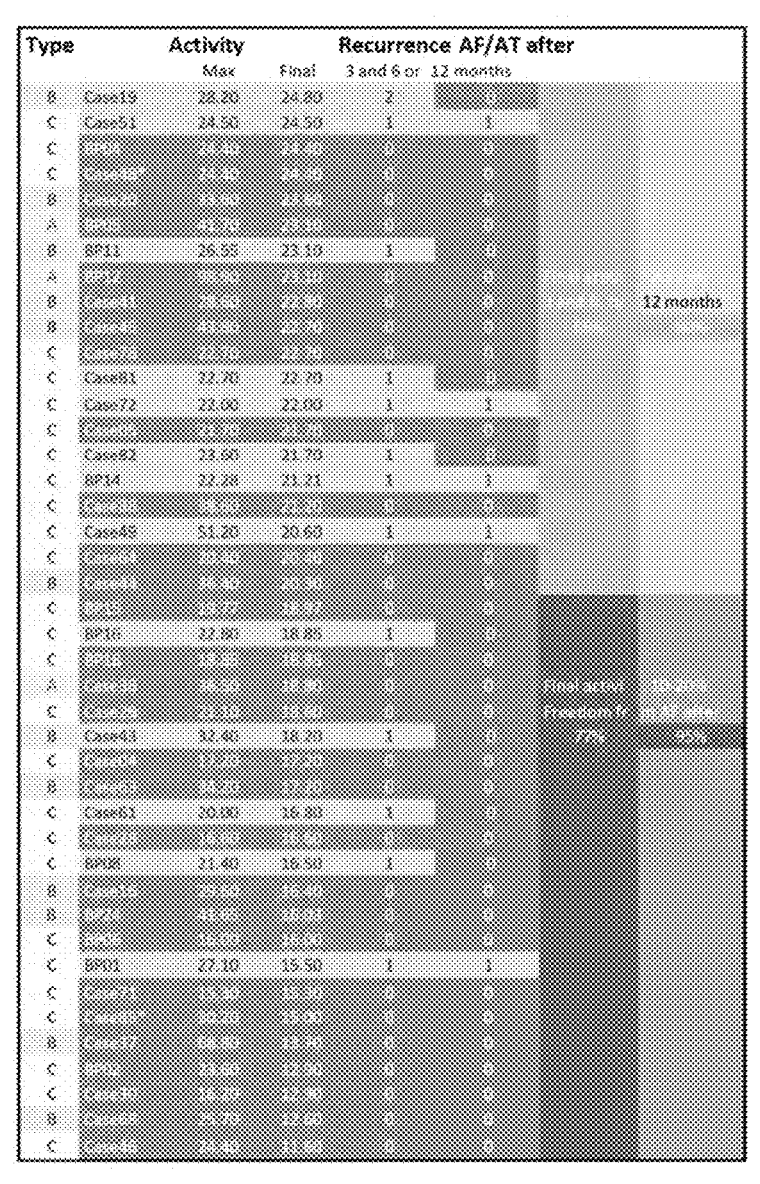

FIGS. 21 and 22 show some data from the validation studies. FIG. 21 shows data corresponding to patients in the validation study where FIRM ablation was ineffective. FIG. 22 shows data corresponding to patients in the validation study where FIRM ablation was effective. From among the 78 patients in the validation study, 45 patients were classified as A- or B-type patients (58% of the validation study population). FIG. 21 data represent 29 patients where: (a) FIRM ablation was not effective (Final Activity >25% and Steadiness >10); (b) 14% of patients exhibited freedom from AF/AT after 3, 6 and 12 months, and 69% of patients suffered a recurrence of AF/AT after 12 months. FIG. 22 data represent 16 patients where: (a) FIRM ablation was effective (Final Activity <25% or Steadiness <10); (b) 75% of the 16 patients were free from AF/AT after 3, 6 and 12 months (p=0.00004); and (c) 0% of the 16 patents suffered a recurrence of AF/AT after 12 months (p=0.00015).

In the validation studies, patients were classified as A-, B- or C-type patients according to the following criteria:
Type-A or B patients:
Maximal Activity of leading source >25% and Steadiness >10 E/s)
A-type: single source only
B-type: two or more sources
Type-C:
Maximal Activity of leading source <25% or
<Spatial Variability or Steadiness <10 E/s).

The data in FIGS. 21 and 22 indicate that source ablation of A- and B-type patients significantly improves outcomes. Moreover, the validation studies confirm the strong correlation discovered in the pilot study between outcome and Final Activity.

Figure 11D:
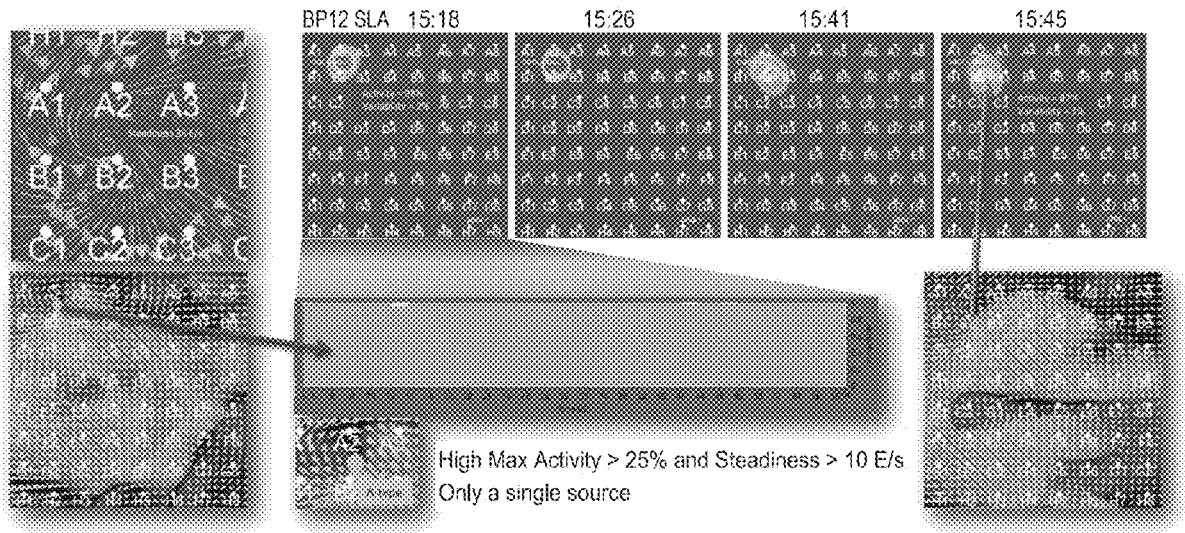
FIGS. 11(d) through 11(f) show EGF results obtained in selected patients from EGF studies.
Figure 11E:
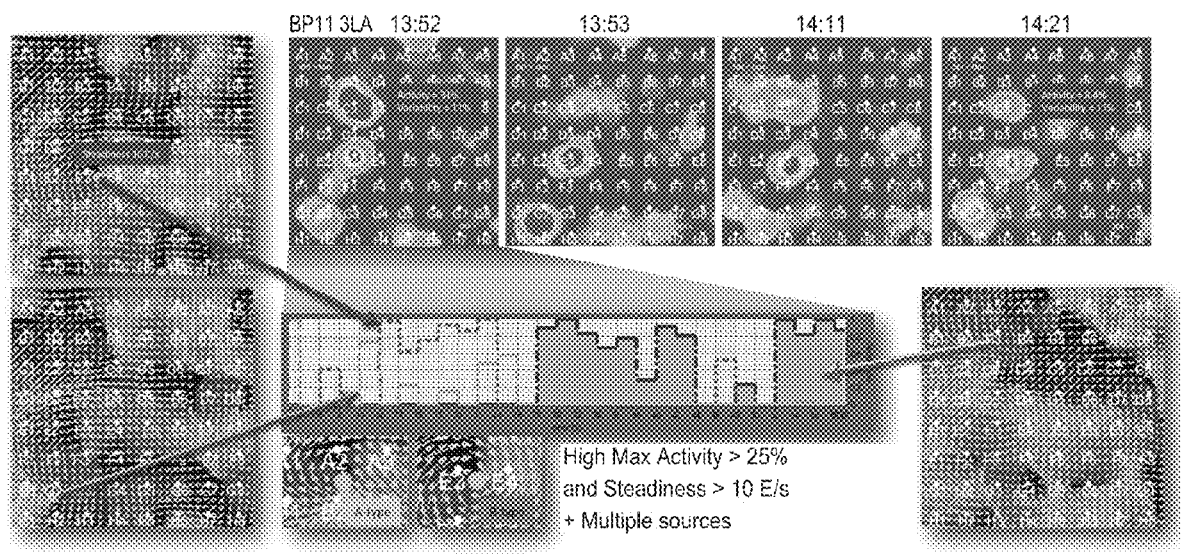
Figure 11F:
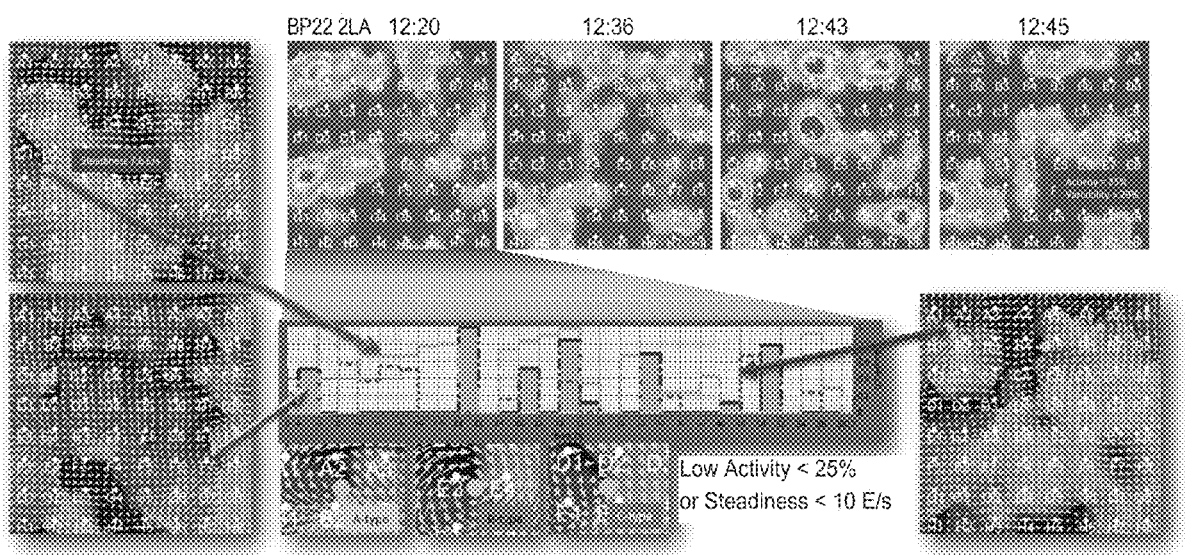

FIGS. 11(d) through 11(f) show EGF results obtained in selected patients from the EGF studies, where EGF techniques were employed to provide the displayed velocity vector maps. (Note that other types of vector maps may also be generated using EGF techniques.)

FIG. 11(d) shows one example or embodiment of EGF results obtained in an "A-type" patient involved in the studies, where high maximum activity exceeding 25% and a steadiness value exceeding 10 E/s are detected for a single source.

FIG. 11(e) shows one example or embodiment of EGF results obtained in an "B-type" patient involved in the studies, where high maximum activity exceeding 25% and a steadiness value exceeding 10 E/s are detected, but where multiple sources (not a single source, as in A-type patients) switch on and off.

FIG. 11(f) shows one example or embodiment of EGF results obtained in an "C-type" patient involved in the studies, where low activity less than 25% and a steadiness value less than 10 E/s are detected, and where multiple sources exhibiting chaotic variability are detected.

FIG. 11(g) summarizes EGF results and conclusions from the EGF studies; namely, that EGF analysis can be used to define the therapy a particular patient receives. A- and B-type patients will generally profit or benefit from targeted intra-cardiac ablations of stable atrial sources. C-type patients are generally cured by pulmonary vein isolation (PVI) only, and do not additionally profit or benefit from targeted ablation. This means that in comparison to invasive surgical procedures such as intra-cardiac EP mapping and catheter ablation, significantly less expensive and significantly less time consuming extracorporeal methods can first be employed, where practicable, to prescreen AF patients. Such an extracorporeal pre-classification method (e.g., employing body surface electrodes in combination with EGF techniques, as described below, for example) can be used to funnel some patients towards no invasive treatment, others towards rapid PVI procedures using only single-shot devices, and still others towards full-scale basket catheter EGF-guided procedures. Such pre-screening extracorporeal methods can save time, money, and improve outcomes.

Figure 11H:
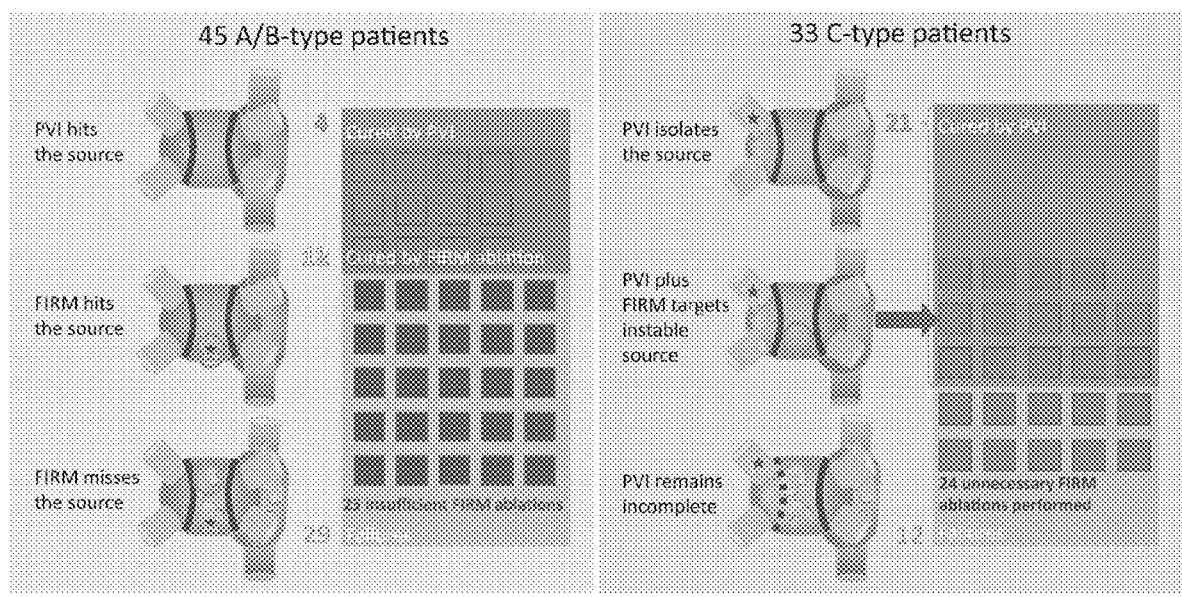

Additionally, and referring to FIGS. 11(g) and 11(h), comparative outcome data show that using EGF technology for therapy guidance improved TOPERA FIRM outcomes by about 25% (19% vs 81% treatment success of the AB1 patients who represent 40% of the 108-patient cohort). Still further, and as shown in FIG. 11(h), a comparison of NB-type patients to C-type patients shows that PVI alone can cure EGF C-type patients, while NB-type patients are best treated with EGF-guided source ablation. Finally, in the validation studies, 25 NB-type patients were found to have been treated with insufficient FIRM ablation (or 32% of the study population). These patients would very likely have benefited significantly from EGF-guided therapy.

Referring now to FIGS. 12(a) through 14(b), there are shown and illustrated various aspects of extracorporeal or body surface electrode EGF systems, devices, components, and methods, which may be employed, by way of non-limiting example, to pre-screen AF patients as described above, or as diagnostic tools for determining whether a patient has AF or AT before more complicated, involved, invasive, and/or time-consuming procedures might be employed (e.g., employing an intra-cardiac basket catheter to map a patient's atrium).

Figure 12A:
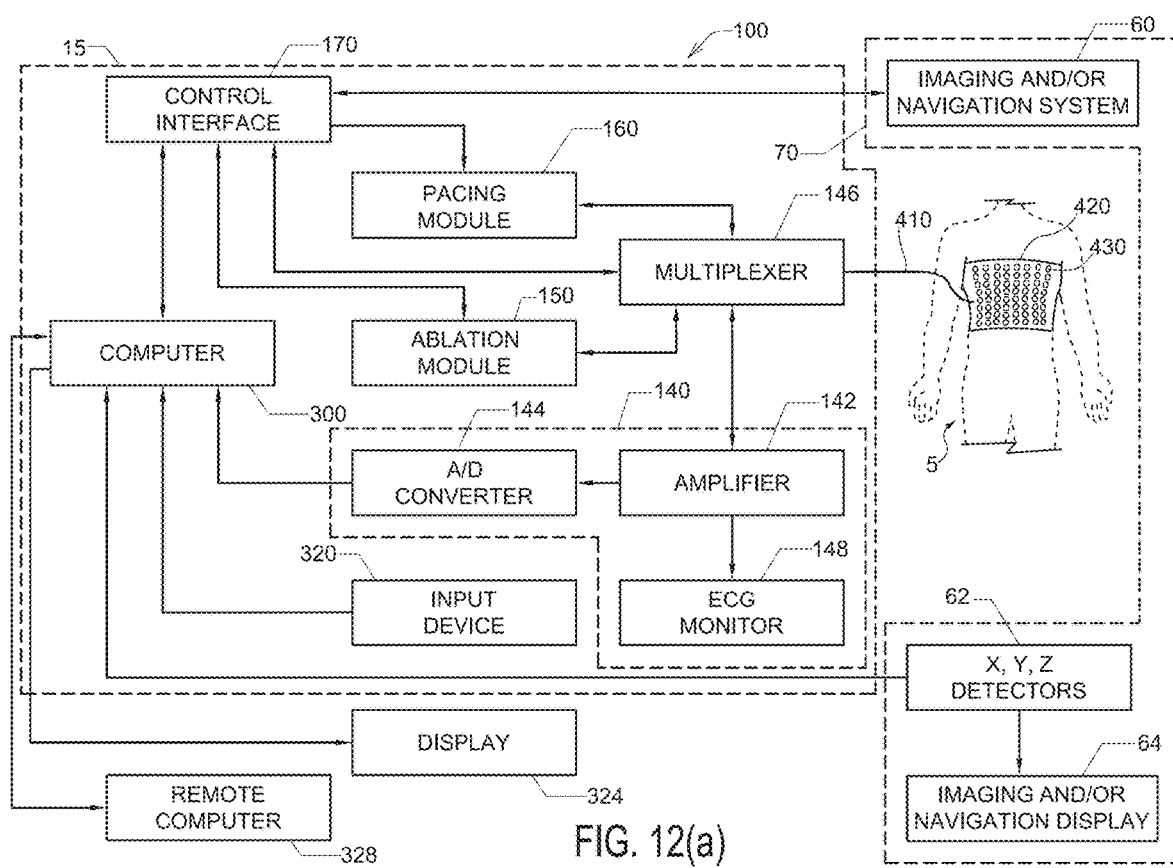
FIGS. 12(a) and 12(b) illustrate two different embodiments of a combined extracorporeal body surface electrode EGF and/or cardiac electrophysiological mapping (EP), pacing and ablation system 100.
Figure 12B:
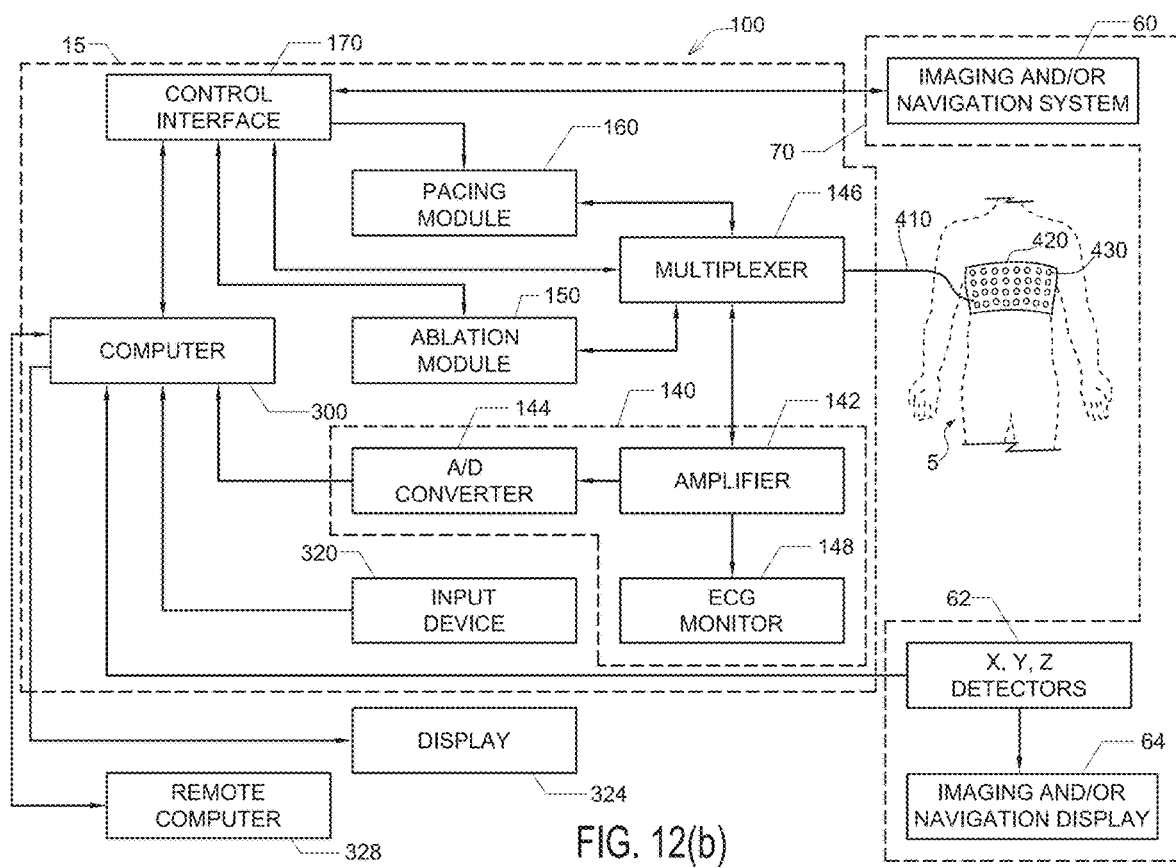
Figure 12C:
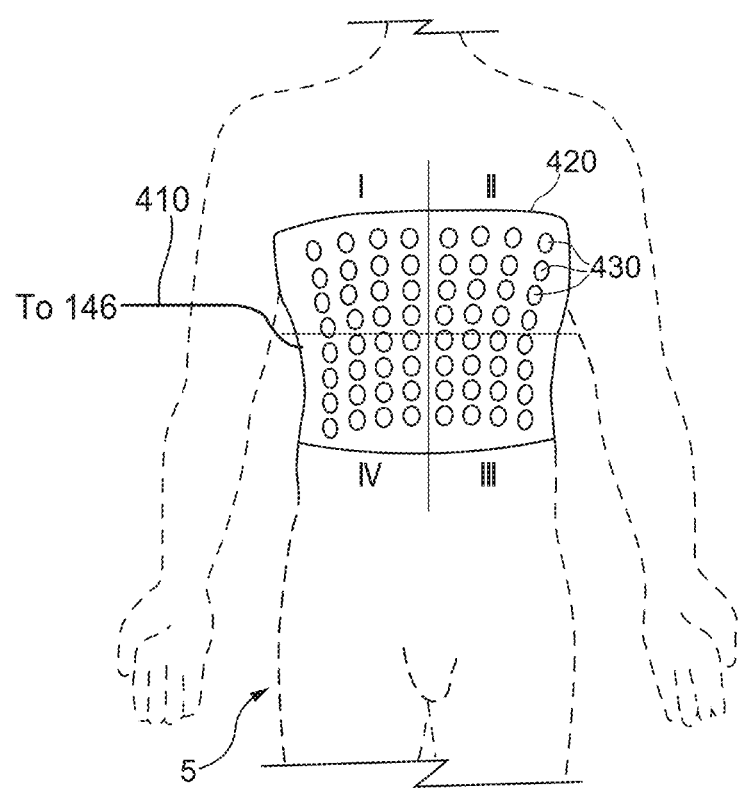
FIGS. 12(c) and 12(d) show respective anterior and posterior views of a patient's thorax with vest 420 worn on or attached thereto.
Figure 12D:
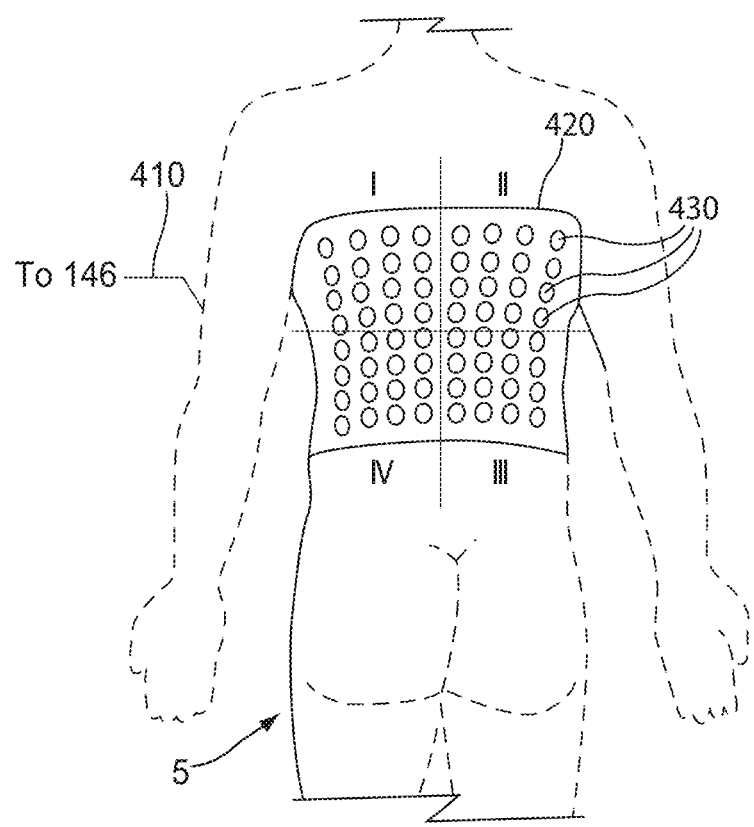

FIGS. 12(a) and 12(b) illustrate two different embodiments of a combined extracorporeal body surface electrode EGF and/or cardiac electrophysiological mapping (EP), pacing and ablation system 100. System 100 shown in FIGS. 12(a) and 12(b) shares many aspects and features with system 100 shown in FIG. 1(a), where certain portions thereof may be interchanged, such as, by way of example, intra-cardiac pacing or ablation catheter 110 with external extracorporeal electrode vest 420, or may be removed, such as, by way of example, ablation module 150, pacing module 160, etc., depending of course on the particular application at hand. There is no need to repeat all the descriptions of the portions of systems 100 and 300 that are described above in connection with FIGS. 1(a) and 1(b), but that are shown in FIGS. 12(a) and 12(b).

In FIGS. 12(a) and 12(b) there is shown a patient 5 wearing a body surface electrode vest 420 comprising a plurality of body surface electrodes 430, which are operably connected through electrical connection 410 to multiplexer 146, and thence to modules 140 and 300. Body surface electrodes 430 are configured to sense ECGs or body surface electrogram signals originating from the patient's heart. Module 140 is configured to receive such ECGs or electrogram signals through electrical connection or cable 410, and to condition such signals for further processing by computer 300. In some embodiments, electrical connection or cable 410 is replaced by a wireless connections, such as BLUETOOTH® connection.

In FIG. 12(a), there are shown 64 body surface electrodes 430 mounted on the anterior portion of vest 420, which in turn is worn on or attached to the thorax of patient 5. In some embodiments, another 64 body surface electrodes 430 may be mounted on the posterior surface of vest 420 (not shown in FIG. 12(a)).

In FIG. 12(b), there are shown 32 body surface electrodes 430 mounted on the anterior portion of vest 420, which in turn is worn on or attached to the thorax of patient 5. In some embodiments, another 32 body surface electrodes 430 may be mounted on a posterior surface of vest 420 (not shown in FIG. 12(a)).

Continuing to refer to FIGS. 12(a) and 12(b), any suitable number of body surface electrodes 430 may be employed in system 100. Generally, the more body surface electrodes 430 employed the better so as to improve resolution and avoid, for example, spatial aliasing of electrical signals originating from patient's heart 10 arriving at the surface of the patient's thorax. Other numbers, arrangements, configurations, and types of body surface electrodes 430 are also contemplated, however. In some embodiments, at least some body surface electrodes 430 and vest 420 are together configured to detect cardiac activation or electrical signals, and to generate electrocardiograms or body surface electrogram signals, which are then relayed by electrical conductors in cable 410 from the individual electrodes 430 to data acquisition device 140.

It is further contemplated that body surface electrodes 430 may be mounted, attached or coupled to the patient's thorax by means other than a vest, such as electrode strips, individually, or by other means known in the art. For example, electrode strips manufactured by Goltec GmbH of Cremlingen, Germany can be used. Carbon and metal body surface electrode strips are available from Goltec GmbH. Carbon electrode strips have the advantage of being radio-translucent, i.e., being transparent or substantially transparent during X-ray imaging.

Electrodes may be provided only on the anterior portion of the patient's thorax, only on the posterior portion of the patient's thorax, on side or lateral portions of the patient's thorax, or on any suitable combination of anterior, posterior and/or lateral portions of the patient's thorax.

Continuing to refer to FIGS. 12(a) and 12(b), and as mentioned above, electrodes 430 are configured to sense electrical activity originating in patient's heart 10. In addition to sensing electrodes 430, other types of devices and/or transducers, such as ground electrodes, navigation patches, position markers, or other devices may be configured to operate in conjunction with, be incorporated into, or form a portion of vest 420, electrodes 430, and/or system 10. Electrodes 430 may be reusable or disposable, unipolar or bipolar, and may be configured for use with MRT/MRI, X-Ray, and/or CAT scanning imaging systems or other types of imaging systems 60. Imaging and/or navigation system 60 may be employed used to help identify and determine the precise positions of the various electrodes 430 or position markers included in vest 430. Gels, adhesives, and liquids may be employed to improve electrical coupling of electrodes 430 with the patient's body, as is well known in the art.

Note that in some embodiments, system 100 of FIGS. 12(a) and 12(b) may not include multiplexer 146, ablation module 150, pacing module 160, imaging and/or navigation system, 60, or other modules or components shown in FIGS. 12(a) and 12(b). Among other things, the embodiments of system 100 shown in FIGS. 12(a) and 12(b) are configured to detect and reconstruct cardiac activation information acquired from a patient's heart relating to cardiac rhythm disorders and/or irregularities, and are further configured to detect and discover the location of the source of such cardiac rhythm disorders and/or irregularities with enhanced precision relative to prior art techniques using body surface electrodes 430. In some embodiments, system 100 is further configured to treat the location of the source of the cardiac rhythm disorder or irregularity, for example by ablating the patient's heart at the detected source location.

The embodiment of system 100 shown in FIGS. 12(a) and 12(b) comprises five main functional units: electrophysiological mapping (EP mapping unit) 140 (which is also referred to herein as data acquisition device 140), ablation module 150, pacing module 160, imaging and/or navigation system 70, and computer or computing device 300. Data acquisition, processing and control system 15 comprises data acquisition device 140, ablation module 150, pacing module 160, control interface 170 and computer or computing device 300. In one embodiment, at least one computer or computing device or system 300 is employed to control the operation of one or more of systems, modules and devices 140, 150, 160, 170 and 70. Alternatively, the respective operations of systems, modules or devices 140, 150, 160, 170 and 70 may be controlled separately by each of such systems, modules and devices, or by some combination of such systems, modules and devices.

Computer or computing device 300 may be configured to receive operator inputs from an input device 320 such as a keyboard, mouse and/or control panel. Outputs from computer 300 may be displayed on display or monitor 324 or other output devices (not shown in FIGS. 12(*a*) and 12(*b*)). Computer 300 may also be operably connected to a remote computer or analytic database or server 328. At least each of components, devices, modules and systems 60, 110, 140, 146, 148, 150, 170, 300, 324 and 328 may be operably connected to other components or devices by wireless (e.g., BLUETOOTH) or wired means. Data may be transferred between components, devices, modules or systems through hardwiring, by wireless means, or by using portable memory devices such as USB memory sticks.

During body surface EP mapping, EGF analysis, and/or other flow or tracking analysis and/or procedures, and as described above, body surface electrodes 430 are positioned on the thorax of patient 5, and by way of example may be mounted on a vest 420 that is configured to place individual electrodes 430 in predetermined positions on the patient's body. These predetermined electrode positions can also be provided to imaging and/or navigation system 60 and/or to computer 300 as a data file so that the spatial positions of body surface electrodes 430 are known (at least approximately), and so that EGF analysis can be carried out accordingly as described above in connection with intra-cardiac EGF analysis (e.g., as described above in connection with FIGS. 1(*a*) through 10(*d*)).

When system 100 of FIGS. 12(*a*) and 12(*b*) is operating in an EP mapping mode, EGF mode, or other flow or tracking mode, body surface electrodes 430 function as detectors of electrocardiographic signals. In one embodiment, the analog signals obtained from body surface electrodes 430 are routed by multiplexer 146 to data acquisition device 140, which comprises an amplifier 142 and an A/D converter (ADC) 144. The amplified or conditioned electrogram signals may be displayed by electrocardiogram (ECG) monitor 148. The analog signals are also digitized via ADC 144 and input into computer 300 for data processing, EGF analysis and graphical display (as described above).

Note that in some embodiments of system 100 shown in FIGS. 12(*a*) and 12(*b*), and as described above, multiplexer 146 may not form a portion of system 100. In addition, in some embodiments computing device 300 may be combined or integrated with one or more of data acquisition device 140, ablation module 150, and/or pacing module 160.

Referring now to FIGS. 12(*c*) and 12(*d*), here are shown respective anterior and posterior views of patient 5's thorax with vest 420 worn on or attached thereto. Quadrants I, II, III, and IV are shown in each of FIGS. 12(*c*) and 12(*d*), which delineate quadrants into which electrodes 430 fall. Some quadrants or portions of such quadrants may be more useful or suitable than others for purposes of acquiring body surface electrogram signals of sufficient fidelity that correspond to the patient's right or left atria, for example, or to any other portion of the patient's heart which is desired to analyzed using EGF or EP mapping techniques. See, for example, "Detailed Anatomical and Electrophysiological Models of Human Atria and Torso for the Simulation of Atrial Activation" to Ferrer et al, PLOS One, Nov. 2, 2015, DOI:10.1371/journal.pone.0141573 (hereafter "the Ferrer reference"), the entire disclosure of which is hereby incorporated by reference herein pursuant to an Information Disclosure Statement filed on even date herewith containing a complete copy of such publication. See also "Body surface localization of left and right atrial high-frequency rotors in atrial fibrillation patients: A clinical-computational study" to Rodrigo et al., *Heart Rhythm*, September 2014, 11(9): 1584-1591, doi:10.1016/j.hrthm.2014.05.013 (hereafter "the Rodrigo reference"), the entire disclosure of which is also hereby incorporated by reference herein pursuant to an Information Disclosure Statement filed on even date herewith containing a complete copy of such publication.

By way of non-limiting example, body surface electrodes 430 may be clustered or more densely positioned on those portions of a patient's thorax that are expected to yield, or that are measured to yield, the best or optimum fidelity body surface electrogram signals corresponding to signals originating in a patient's atrium, the two atria, or any other target portion of the patient's heart 10 that is to be analyzed. For example, body surface electrodes 430 can be concentrated on the anterior portion of the patient's thorax in the region where quadrants I, II, III and IV intersect near the middle of the thorax, or at a location slightly upwards from, or slightly upwards and to the left from, such intersection. Note that electrodes 430 can be arranged on the patient's thorax in any suitable pattern or configuration, including, but not limited to, an array of rows and columns (as shown in FIGS. 12(*a*) through 12(*d*)), a rectangular array, a square array, a circular or elliptical array, a cross-shaped array, a star-shaped array, and/or an array with varying electrode density or spacing where electrode spacing is finest in a region of maximum interest and least in a region of less interest. As body surface electrode data from a patient's thorax are analyzed using EGF techniques and/or machine learning techniques (more about which is said below), the locations of electrodes 430 on patient's thorax 5 may also be changed or adjusted so that body surface electrogram signals of the highest fidelity and/or lowest noise are acquired by system 100.

In one embodiment, body surface electrogram signal data are processed by computer 300 to produce a display showing the location(s) of the source(s) of cardiac rhythm disorders and/or irregularities in the patient's heart 10 in real-time or near-real-time, further details of which are provided below. That is, at and between the sampled locations of the patient's endocardium, computer 300 may be configured to compute and display in real-time or near-real-time an estimated, detected and/or determined location(s) of the site(s), source(s) or origin)s) of the cardiac rhythm disorder(s) and/or irregularity(s) within the patient's heart 10. This permits a medical practitioner to select interactively and quickly the electrodes 430 of vest 420 that are best detecting the location of the source(s) of the cardiac rhythm disorder or irregularity. Note that in some embodiments, EGF techniques are utilized to analyze body surface electrogram signal data without having to resort to complicated, lengthy and computationally-intensive tomographic or reverse modeling computations. In some applications, all that is required is to determine whether sources of AF and/or AT are present in a patient's atrium or atria, and whether those sources are stable or unstable. In other embodiments, and assuming sufficient computational power is available to process the acquired body surface electrogram signals, reverse modeling (e.g., "solving the reverse problem"), downward continuation, and/or employing tomographic techniques using a three-dimensional grid of voxels may be employed to yield higher fidelity and more accurate EGF results.

Referring once again to FIGS. 12(*a*) and 12(*b*), EP mapping system or data acquisition device 140 is configured to condition the analog body surface electrogram signals delivered by electrodes 430 to amplifier 142. Conditioning of the analog body surface electrogram signals received by amplifier 142 may include, but is not limited to, low-pass filtering, high-pass filtering, bandpass filtering, and notch filtering. The conditioned analog signals are then digitized in analog-to-digital converter (ADC) 144. ADC 144 may further include a digital signal processor (DSP) or other type of processor which is configure to further process the digitized electrogram signals (e.g., low-pass filter, high-pass filter, bandpass filter, notch filter, automatic gain control, amplitude adjustment or normalization, artifact removal, etc.) before they are transferred to computer or computing device 300 for further processing and analysis.

In some embodiments, the rate at which individual body surface electrogram and/or ECG signals are sampled and acquired by system 100 can range between about 0.25 milliseconds and about 8 milliseconds, and may be about 0.5 milliseconds, about 1 millisecond, about 2 milliseconds or about 4 milliseconds. Other sample rates are also contemplated. While in some embodiments system 100 is configured to provide unipolar signals, in other embodiments system 100 is configured to provide bipolar signals.

In one embodiment, system 100 can include a BARD® LABSYSTEM™ PRO EP Recording System, which is a computer and software driven data acquisition and analysis tool designed to facilitate the gathering, display, analysis, pacing, mapping, and storage of intracardiac EP data. Also, in one embodiment, data acquisition device 140 can include a BARD® CLEARSIGN™ amplifier, which is configured to amplify and condition electrocardiographic signals of biologic origin and pressure transducer input, and transmit such information to a host computer (e.g., computer 300 or another computer).

Computing device or computer 300 is suitably configured and programmed to receive or access the body surface electrogram signals provided by body surface electrodes 430. Computer 300 is further configured to analyze or process such electrogram signals in accordance with the methods, functions and logic disclosed and described herein so as to permit reconstruction of cardiac activation information from the electrogram signals using EGF techniques. This, in turn, makes it possible to locate with at least some reasonable degree of precision the location of the source of a heart rhythm disorder or irregularity. Once such a location has been discovered—or not discovered—the characteristics of the source(s) may be analyzed and the therapy, if any, that is to be delivered to the patient may be determined.

In one embodiment, and as shown in FIGS. 12(*a*) and 12(*b*), system 100 may also comprise a physical imaging and/or navigation system 70. Physical imaging and/or navigation device 60 included in system 70 may be, by way of example, a 2- or 3-axis fluoroscope system, an ultrasonic system, a magnetic resonance imaging (MRI) system, a computed tomography (CT) imaging system, and/or an electrical impedance tomography EIT) system. Operation of system 70 be controlled by computer 300 via control interface 170, or by other control means incorporated into or operably connected to imaging or navigation system 70. In one embodiment, computer 300 or another computer triggers physical imaging or navigation system 60 to take "snap-shot" pictures of the heart 10 of a patient (body not shown). A picture image is detected by a detector 62 along each axis of imaging, and can include a silhouette of the heart as well as a display of the positions of body surface electrodes 430 on the patient's thorax (more about which is said below), which is displayed on imaging or navigation display 64. Digitized image or navigation data may be provided to computer 300 for processing and integration into computer graphics that are subsequently displayed on monitor or display 64 and/or 324.

Medical navigation systems suitable for use in the various embodiments described and disclosed herein include, but are not limited to, image-based navigation systems, model-based navigation systems, optical navigation systems, electromagnetic navigation systems (e.g., BIOSENSE® WEBSTER® CARTO® is system), and impedance-based navigation systems (e.g., the St. Jude® ENSITE™ VELOCITY™ cardiac mapping system), and systems that combine attributes from different types of imaging AND navigation systems and devices to provide navigation within the human body (e.g., the MEDTRONIC® STEALTHSTATION® system).

Figure 13:
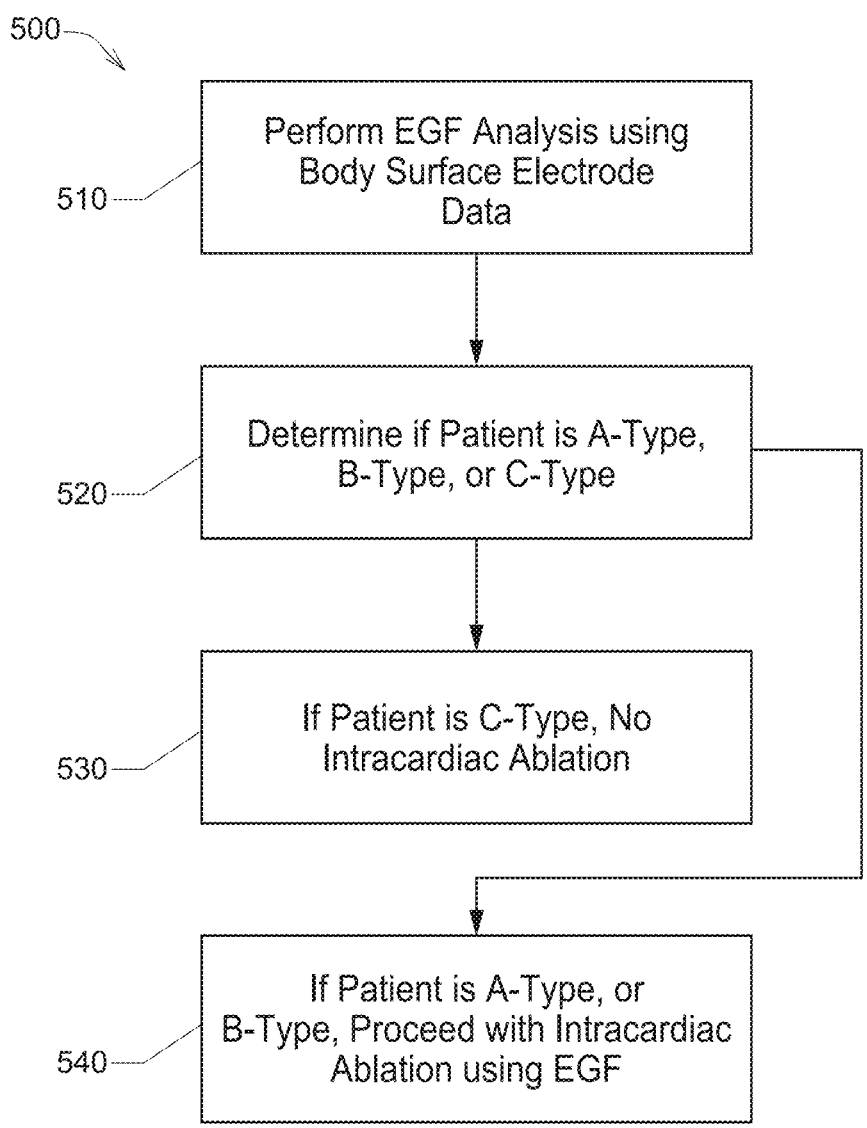
FIG. 13 shows a generalized method 500 of employing EGF techniques in conjunction with body surface electrodes 430.

Referring now to FIG. 13, there is shown one embodiment of a generalized method 500 of employing EGF techniques in conjunction with body surface electrodes 430 to permit patients to be classified as A-type, B-type or C-type patients, which method comports with the EGF patient classification discussion set forth above. At step 510, EGF analysis is performed on body surface electrode data that have been acquired from a patient using, by way of non-limiting example, system 100 of FIG. 12(*a*) or 12(*b*). EGF analysis can be carried out in accordance with the teachings set forth above that relate to, or are described in connection with, FIGS. 1 through 11(*a*). In step 520, it is determined whether the patient is an A-type patient, a B-type patient, or a C-type patient, using EGF techniques (such as those described above in connection with FIGS. 11(*b*) through 11(*h*)). If the patient is determined to be an A- or B-type patient, intra-cardiac ablation of the detected source(s) can be carried out at step 540 with the benefit of the EGF techniques described in detail above. If the patient is determined to be a C-type patient at step 520, no intra-cardiac ablation is carried out at step 530, although PVI for that patient may be well advised depending on the EGF results. After having read and understood the present specification and drawings, those skilled in the art will understand that many variations, combinations, and permutations of method 500 are possible.

Figure 14A:
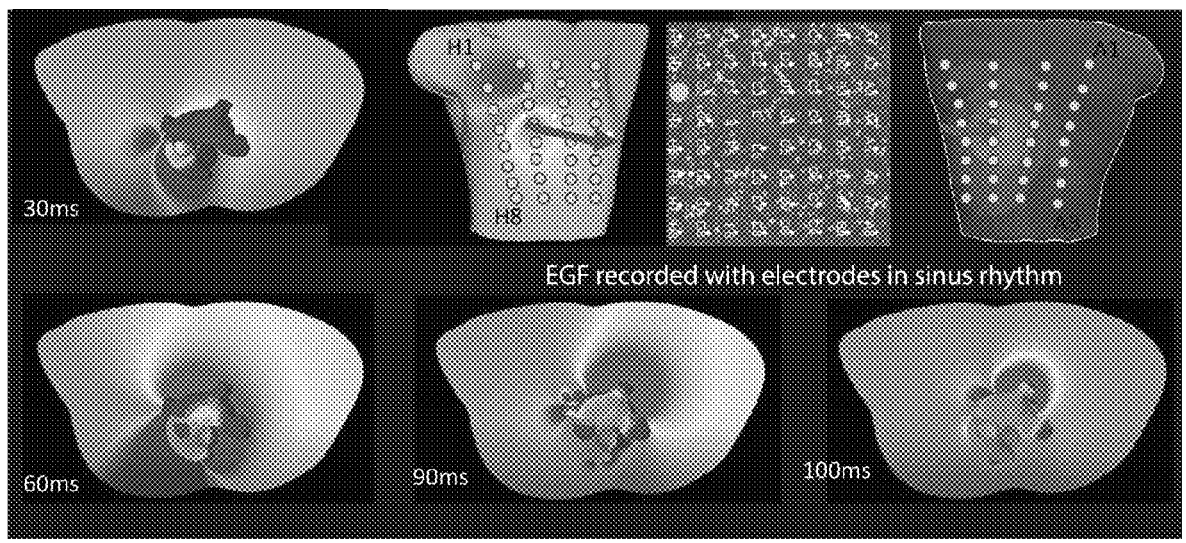
FIGS. 14(a) and 14(b) show examples of EGF analysis carried out using body surface electrodes 430 and EGF techniques
Figure 14B:
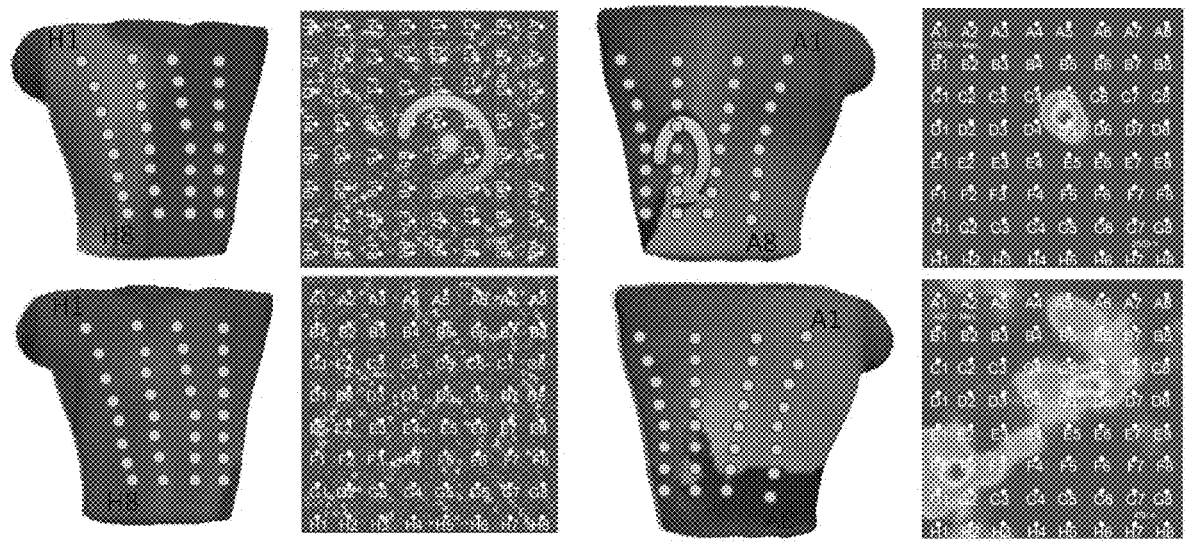

FIGS. 14(*a*) and 14(*b*) show examples of EGF analysis carried out using body surface electrodes and EGF techniques. In FIG. 14(*a*), simulated electrical potential wave propagation from the heart to and across body surface electrodes is illustrated for calculated potential distributions occurring as a normal sinus rhythm P-wave propagates from its source outwardly to 30 msec., 60 msec., 90 msec., and 100 msec. EGF results obtained with surface body electrodes are shown in the upper right central portion of FIG. 14(*a*), where no AF source is indicated or detected. In FIG. 14(*b*), simulated electrical potential wave propagation from the heart to and across body surface electrodes is illustrated for calculated potential distributions occurring in a patient with AF. EGF results obtained from simulated body surface electrodes are shown in the four EGF panels of FIG. 14(*b*), where an AF source is clearly indicated and has been detected. FIGS. 14(*a*) and 14(*b*) show body surface potential distributions sharing some similarities to those discussed above in the Ferrer and Rodrigo references.

With reference to the foregoing discussion and the Figures relating thereto (e.g., FIGS. 1(*a*) through 14(*b*)), and further with respect to other discussions and Figures set forth herein, the following additional embodiments, features, and aspects are also contemplated.

In one embodiment, there is provided a system configured to detect at least one location of at least one source of at least one cardiac rhythm disorder in a patient's heart, the system comprising: (a) at least one computing device; (b) at least one data acquisition device operably connected to the at least one computing device or configured to provide as outputs therefrom body surface electrogram signals; (c) a plurality of body surface electrodes configured to generate body surface electrogram signals and for placement on the patient's body surface, the plurality of body surface electrodes being operably connected to the at least one data acquisition device, and (d) a display or monitor operably connected to the at least one computing device and configured to visually display to the user one or more vector maps generated by the at least one computing device; wherein the computing device comprises at least one non-transitory computer readable medium configured to store instructions executable by at least one processor to determine the at least one location of the at least one source of the at least one cardiac rhythm disorder in the patient's heart, the computing device being configured to: (i) receive the body surface electrogram signals from the plurality of body surface electrodes located on the patient's body, where amplitudes of the body surface electrogram signals received by the at least one computing device have been at least one of conditioned, amplified, normalized, filtered, and adjusted by the data acquisition device before being provided to the computing device; (ii) assign or relate positional data corresponding to predetermined positions of the body surface electrodes on the patient's body to their respective corresponding body surface electrogram signals and body surface electrodes; (iii) generate at least one spatial map of the body surface electrode positions; (iv) for each or selected discrete times over which the body surface electrogram signals are being processed, process the amplitude-adjusted body surface electrogram signals to generate a plurality of electrogram surfaces or data grids, each such surface or data grid corresponding at least partially to the at least one spatial map, at least one surface or data grid being generated for each such time, and (v) process the plurality of electrogram surfaces or data grids through time to generate at least one vector or other map corresponding at least partially to the spatial map, the at least one vector or other map being configured to reveal the at least one location of the at least one source of the at least one cardiac rhythm disorder, the at least one vector map being shown to the user on the display or monitor.

The foregoing embodiment can further comprise: (1) the plurality of electrogram surfaces being a plurality of three-dimensional electrogram surfaces that includes a first three-dimensional electrogram surface corresponding to a first EGF or other recording of a first duration of time and a second three-dimensional electrogram surface corresponding to a second EGF or other recording of a second duration of time, the second duration of time being greater than the first duration of time; (2) the first and second three-dimensional electrogram surfaces facilitating a determination of whether the patient's AF revealed in the velocity vector or EGF map, or other type of map, is characterized by one or more of: (a) atrial behavior exhibiting spatially and temporally stable rotors, drivers or sources (Type A); (b) atrial behavior where spatially stable rotors switch on and off (Type B), and (c) chaotic atrial behavior in which the rotors are spatially and temporally variable (Type C); (3) the first duration of time ranging between about 0.5 seconds and about 30 seconds, between about 1 second and about 5 seconds, or between about 1 second and about three seconds; (4) sources being detected over a duration of between about 0.5 seconds and about 30 seconds, or between about 1 second and about 15 seconds; (5) the second duration of time ranging between about 1 minute and about 3 minutes, between about 30 seconds and about 10 minutes, or between about 15 seconds and about 20 minutes; (6) the vector map being a velocity vector map; (7) at least one of an activity value, a flow angle stability value, and a steadiness value being generated by the computing device for one or more sources corresponding to the at least one cardiac rhythm disorder revealed in the vector map; (8) at least one of the activity value, the flow angle stability value, and the steadiness value being displayed on the display or monitor; (9) on the basis of at least one of the generated activity values, flow angle stability values, and steadiness values the computing device determining whether to classify the patient as an A-type patient, a B-type patient, or a C-type patient; (10) the computing device being configured to determine whether the at least one velocity vector or other map corresponds to an A-type patient, a B-type patient, or a C-type patient; (11) the electrogram surfaces or data grids comprising at least one three-dimensional surface; (12) the electrogram surfaces or data grids being generated by the computing device using Green's function; (13) the vector map generated by the computing device being configured to reveal a location in the patient's heart of one or more of: (a) an active rotor; (b) a passive rotor; (c) a breakthrough point, and (d) a focal point; (14) the velocity vector or other map being generated by the computing device using at least one of an optical flow analysis technique, a video tracking analysis technique, a motion capture analysis technique, a motion estimation analysis technique, a data association and segmentation tracking analysis technique, a particle tracking analysis technique, and a single-particle tracking analysis technique; (15) at least one optical flow analysis technique, if employed, being selected from the group consisting of a Horn-Schunck method, a Buxton-Buston method, a Black-Jepson method, a phase correlation method, a block-based method, a discrete optimization method, a Lucas-Kanade method, and a differential method of estimating optical flow; (16) the at least one processor and the at least one non-transitory computer readable medium being configured to determine, using a trained atrial discriminative machine learning model, predictions or results concerning atrial fibrillation in the patient's heart; (17) the trained atrial discriminative machine learning model having been trained at least partially using data obtained from a plurality of other previous patients, where intracardiac electrophysiological (EP) mapping signals for the other patients have been processed using one or more of electrographic flow (EGF), video tracking analysis, motion capture analysis, motion estimation analysis, a data association and segmentation tracking analysis, particle tracking analysis, and single-particle tracking analysis methods to detect at least one of: (I) the presence of sources of atrial fibrillation in the other patients' hearts; (II) the locations of sources of atrial fibrillation in the other patients' hearts; (III) the activity levels of sources of atrial fibrillation in the other patients' hearts; (IV) the spatial variability levels of sources of atrial fibrillation in the other patients' hearts; (V) the flow angle stability levels of sources of atrial fibrillation in the other patients' hearts; and (VI) the classification of patients as at least one of types A, B and C; (18) paired data sets of body surface electrogram signals and the intracardiac EP mapping signals having been acquired simultaneously from at least some of the plurality of other patients and the paired data sets have been correlated to one another using the trained atrial discriminative machine model; (19) the trained atrial discriminative machine learning model being further configured to generate one or more of the following predictions or results for the patient using the conditioned electrogram signals and positional data corresponding to the patient: (1) Does the patient have atrial fibrillation or not? (2) If the patient has atrial fibrillation, determining at least one of the spatial variability level, the activity level, and the flow angle stability level associated with one or more sources detected in the patient's heart; (3) If the patient has atrial fibrillation, determining the locations of one or more sources detected in the patient's heart; (4) If the patient has atrial fibrillation, whether one or more activation sources detected in the patient's heart are characterized by chaotic flow; and (5) classification of the patient as one of types A, B and C, and (20) the computing device being further configured to: (iv) process the conditioned electrogram data and positional data in the trained machine learning model to generate the one or more predictions or results; and (v) display the one or more predictions or results on the display or monitor to the user.

In another embodiment, there is provided a method of detecting at least one location of at least one source of at least one cardiac rhythm disorder in a patient's heart using a system comprising at least one computing device, the computing device comprising at least one non-transitory computer readable medium configured to store instructions executable by at least one processor to determine the at least one location of the at least one source of the at least one cardiac rhythm disorder in the patient's heart, the system further comprising a plurality of body surface electrodes operably connected to the computing device through a data acquisition device and a monitor or screen operably connected to the computing device, the method comprising: (a) acquiring body surface electrogram signals using the body surface electrodes located on one or more body surfaces of the patient; (b) using at least one of the computing device and the data acquisition device, at least one of conditioning, filtering, normalizing and adjusting the amplitudes of the acquired body surface electrogram signals; (c) using the computing device, assigning positions or identifiers for each of the body surface electrodes to corresponding individual body surface electrogram signals; (d) using the computing device and the assigned positions or identifiers, providing or generating a spatial map of the body surface electrode positions; (e) using the computing device, for each or selected discrete times over which the body surface electrogram signals are being processed, processing the amplitude-adjusted body surface electrogram signals to generate a plurality of electrogram surfaces or data grids corresponding at least partially to the spatial map, one surface or data grid being generated for each such time, and (f) using the computing device, processing the plurality of electrogram surfaces or data grids through time to generate a vector or other map corresponding at least partially to the spatial map, the vector or other map being configured to reveal on the monitor or display to a user the at least one location of the at least one source of the at least one cardiac rhythm disorder.

The foregoing embodiment can further comprise: (1) conditioning the electrogram signals further comprises one or more of amplifying the electrogram signals, notch filtering the electrogram signals, and bandpass, low-pass or high-pass filtering the body surface electrogram signals; (2) generating the electrogram surfaces or data grids using Green's function; (3) showing the at least one cardiac rhythm disorder as an active rotor, a passive rotor, a breakthrough point, or a focal point on the vector map; (4) generating the vector or other map using at least one of an optical flow analysis technique, a video tracking analysis technique, a motion capture analysis technique, a motion estimation analysis technique, a data association and segmentation tracking analysis technique, a particle tracking analysis technique, and a single-particle tracking analysis technique; (5) the at least one optical flow analysis technique, if employed, being selected from the group consisting of a Horn-Schunck method, a Buxton-Buston method, a Black-Jepson method, a phase correlation method, a block-based method, a discrete optimization method, a Lucas-Kanade method, and a differential method of estimating optical flow, and (6) the method further comprising detecting at least one property or characteristic of the at least one source of at least one cardiac rhythm disorder in a patient's heart using the system, where the property or characteristic is, by way of for example, a location, an activity level, a steadiness level, a flow angle stability level, or other property or characteristic disclosed or described herein.

Figure 15:
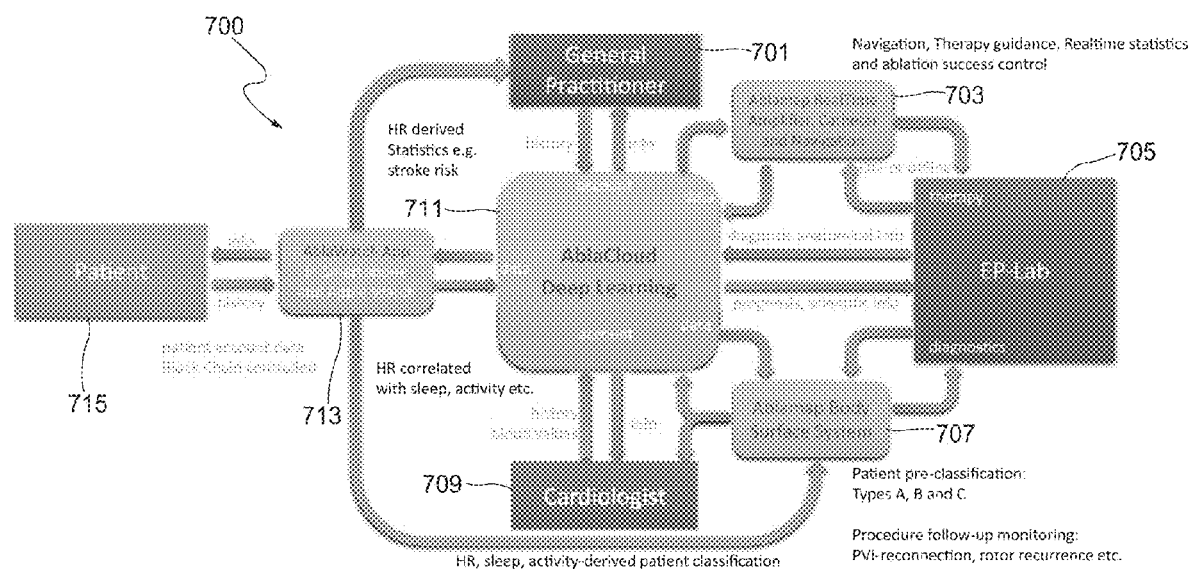
FIG. 15 shows some benefits accruing to one embodiment of an ABLACON EGF analysis system 700.

FIG. 15 shows some benefits accruing to one embodiment of an ABLACON EGF analysis system 700. As shown in the embodiment of FIG. 15, system 700 comprises patient 715, ABLAWATCH app 713, general practitioner 701, ABLAMAP amplifiers, catheters, and navigation systems 703, EP-Lab 705, ABLACLOUD deep learning 711, ABLAMAP body surface system 707, and cardiologist 709. Benefits 720 ("Keep patient safe and informed"), 730 ("Evaluate stroke risk, therapy success forecast, and AF burden (outcome)"), 740 ("Hit extra PV targets"), and 750 ("Avoid needless ablations") arise from use of EGF or other tracking technology when employed in the integrated and holistic manner illustrated in FIG. 15. In system 700, one or more central servers and the Internet can be employed to collect, analyze and disseminate or distribute the various types of information shown in FIG. 15. See, for example, "Association of Atrial Fibrillation Clinical Phenotypes With Treatment Patterns and Outcomes: A Multicenter Registry Study" to Taku Inohara et al., JAMA Cardiol. 2018; 3(1): 54-63, the entirety of which is hereby incorporated by reference herein. Embodiments of system 700 other than that shown explicitly in FIG. 15 are also contemplated, such as systems 700 have more or fewer elements than those shown in FIG. 15.

Figure 16:
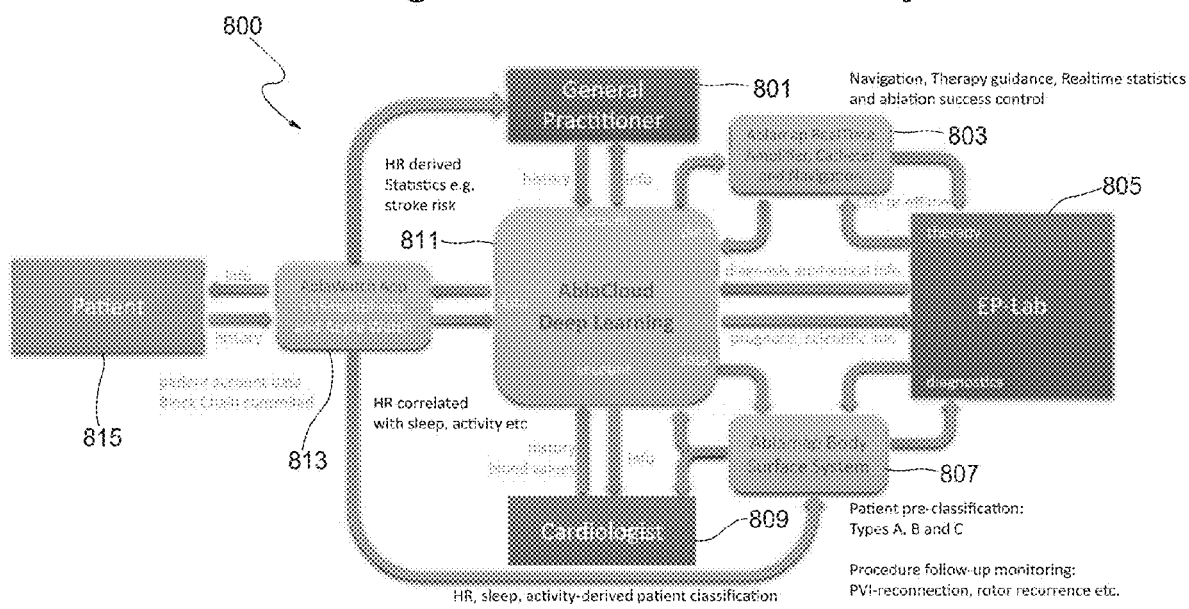
FIG. 16 shows one embodiment of an ABLACON diagnosis and treatment system 800.

FIG. 16 shows one embodiment of an ABLACON diagnosis and treatment system 800, which mirrors at least portions of system 700 shown in FIG. 15. System 800 illustrated in FIG. 16 denotes specific tasks that are carried out in, or results that are provided by, System 700 of FIG. 15 (e.g., history, HR derived statistics, HR correlated with sleep activity, etc.). The holistic and integrated systems illustrated in FIGS. 15 and 16 permit the centralized acquisition, storage, processing, and dissemination of remote information gleaned from hundreds or thousands of patients from around the world. Systems 700 and 800 are configured to permit continuous updating of EGF data and results based on anonymized patient data, and associated deep learning of the system so that EGF results can be improved and made more accurate over time. In addition, EGF results and/or raw or partially processed electrogram signal data from a particular patient can be uploaded to systems 700 and/or 800 for comparison to other data, or for the generation of a diagnosis of the data and/or therapy treatment recommendations or suggestions.

Figure 17:
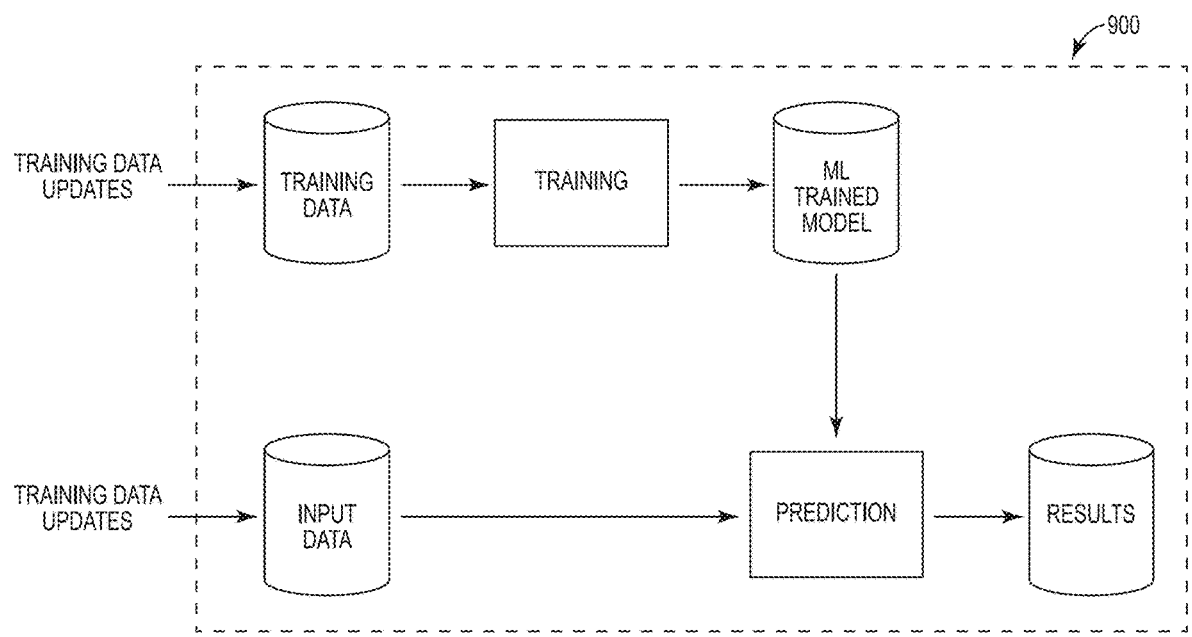
FIG. 17 shows one embodiment of a simplified machine learning system 900 and a corresponding generalized machine learning workflow.
Figure 18:
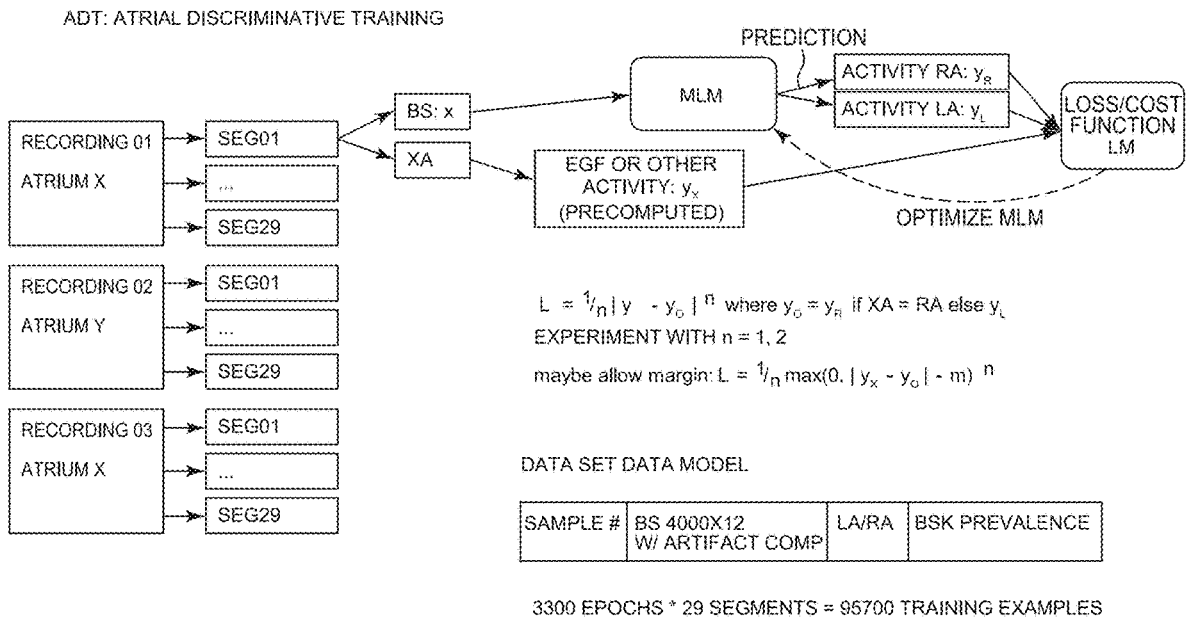
FIG. 18 shows a block diagram and data flow diagram according to one embodiment of a body surface and intra-cardiac electrode machine learning system that employs an atrial discriminative training (ADT) machine learning model (MLM) that works in combination with a loss or cost function module (LM)

Referring now to FIGS. 17 and 18, there are shown various aspects, features and components according to some embodiments of machine learning systems, devices, components, and methods that can be employed to leverage and enhance the benefits and advantages of the body surface electrode and EGF techniques and processes described above so that the natures and types of cardiac rhythm disorders characteristic of patients' hearts can more be more efficiently, accurately, quickly, and cost-effectively detected and diagnosed. In one such embodiment, where a trained atrial discriminative machine learning system is employed, body surface electrode data acquired from a patient serve as the inputs to the trained atrial discriminative machine learning system, which then provides as outputs predicted EGF or other types of flow fields or associated characteristics for the patient's heart and/or a predicted ABC classification of the patient's heart disorders, where such predicted outputs are based upon the body surface electrode and EGF or other suitable flow techniques and processes described above in combination with machine learning techniques, as well as the use of intra-cardiac electrode data (more about which is said below).

FIG. 17 shows one embodiment of a simplified machine learning system 900 and a corresponding generalized machine learning workflow. Training data for system 900 initially comprises paired sets of EGF (or optical flow) results, or other types of flow or tracking techniques described above, obtained from intra-cardiac electrode data and body surface electrode data, where such paired sets of data are acquired and recorded from the same patients at the same time. System 900 is first trained using a sufficiently large number of such sets of paired data until system 900 is capable of providing accurate optical flow or other types of predictions and/or ABC or other suitable patient classifications based upon new body surface electrode data from new patients that are provided later on as input data to system 900. System 900 is preferably configured so that it is continuously and/or periodically updated with new training data. Some generalized types of machine learning methods that can be employed in system 900 include, by way of illustrative but non-limiting example, supervised (e.g., classification or regression) methods, unsupervised (e.g., clustering and estimation of probability density function) methods, and semi-supervised learning (e.g., text/image retrieval system) methods.

Now described are more specific examples of machine learning systems, methods applied to the problem of accurately predicting the presence or classification of cardiac rhythm disorders in a patient's heart based upon input surface body electrode data only (in combination with a trained atrial discriminative machine learning model).

With reference now to FIG. 18, in one embodiment a body surface and intra-cardiac electrode machine learning system and its various components and associated methods are employed to facilitate screening of patients for atrial fibrillation. The system is configured to determine, using only non-invasive body surface electrode data, how best to treat a patient in any subsequent procedures that might be carried out, such as acquiring and analyzing intra-cardiac EP data using a basket catheter, atrial ablation, or pulmonary vein isolation. Such systems and methods may also be employed to determine whether a particular patient is a good or poor candidate for undergoing a further intra-cardiac (e.g., atrial) electrophysiological (EP) mapping diagnostic procedure and/or for an intra-cardiac atrial ablation or PVI procedure. In some embodiments, such a machine learning system and its various components and associated methods are can be used to classify patients potentially suffering from AF as A-, B-, or C-type patients.

In accordance with the teachings and disclosures set forth above and in the Figures, patients who are determined to be C-type patients using the body surface and intracardiac electrode machine learning system described and disclosed herein can be spared the trouble, risk, cost and expense associated with undergoing very likely unnecessary but expensive intra-cardiac EP mapping and/or ablation or PVI procedures that would be unlikely to do anything to improve their state of health. Further in accordance with the teachings and disclosures set forth above and in the Figures, and in contrast, patients who are determined to be A- or B-type patients using the body surface and intracardiac electrode machine learning system described and disclosed herein would be good candidates for intra-cardiac EP mapping and/or ablation or PVI procedures that are very likely to provide them with beneficial results.

FIG. 18 shows a block diagram and data flow diagram according to one embodiment of a body surface and intra-cardiac electrode machine learning system, which employs an atrial discriminative training (ADT) machine learning model (or MLM) that works in combination with a loss or cost function module (or LM). The ADT MLM is configured to provide its results or predictions to the LM, and in turn the LM is configured to provide outputs based on the ADT MLM's results or predictions back to the ADT MLM (more about which is said below). The ADT MLM can be any suitable type of machine learning module or network, such as one or more of the following types of networks or modules: convolutional neural network (CNN), decision tree, support vector machine, logistic regression, mixture of Gaussian, a feedforward neural network or artificial neuron network, a radial basis function neural network, a Kohonen self-organizing neural network, a recurrent neural network (RNN) or long short term memory network, and/or a modular neural network. The ADT MLM and/or the LM can also be configured to employ optimization techniques or schemes such as stochastic gradient descent schemes or decision tree schemes.

Continuing to refer to FIG. 18, in one embodiment of a body surface and intracardiac electrode machine learning system and its various components and associated methods, a goal is to estimate the properties of EGF or other flow or tracking techniques described above using body surface electrodes only. EGF and the other flow or tracking techniques described above can help identify action potential flow patterns for improved understanding and treatment of AF. In some of the embodiments described above, EGF or other types of flow or tracking are estimated using intracardiac unipolar electrodes, which is costly and invasive. By using and leveraging body surface electrode data in combination with intra-cardiac electrode data and EGF or other types of flow results obtained therewith, initial patient evaluation or classification, PVI outcome prediction, coarse or general localization of AF drivers, and more precise follow-up quantification (e.g., "recurrence of AF likely to occur, yes or no) can be carried out at much lower cost, and with essentially no risk to the patient, as compared to conventional invasive intra-cardiac basket catheter EP mapping methods.

Still continuing to refer to FIG. 18, in one embodiment an atrial discriminative (ADT) machine learning model is trained to estimate the correlation of body surface electrode signals to EGF or other flow or tracking properties and characteristics derived from intracardiac electrodes. By way of non-limiting example, such a machine learning model can be a feature extraction method that employs wavelet decomposition and amplitude histograms in combination with a regression or classification model such as a support vector machine, a decision tree or logistic regression, an end-to-end model such as a deep neural network, and/or any combination or permutation of the foregoing.

As shown in FIG. 18, an input signal x to the machine learning model ADT comprises data recorded from body surface electrodes BS (x). In some embodiments, signal x potentially undergoes preprocessing steps, such as a high/ low/band-pass filtering or for the compensation of ventricular artifacts (e.g., removing the QRST complex). The desired output(s) y of the machine learning model provides an estimate(s) for one or more properties of EGF or other types of flow properties in a patient's heart, such as activity or flow angle stability. Training data (x, y) is obtained from simultaneous recordings from body surface electrodes (x) and intracardiac electrodes (y). In one embodiment, the machine learning model is parameterized with parameters W. These can be weights of neural network connections, etc.

The prediction of the machine learning model is then $\hat{y}t=fW(x)$ (or "f of x, parameterized by W"). This prediction should be as close as possible to y. During training, parameters W are optimized so as to minimize the error in estimating y. Such an error can be described as a loss function $L(y, \hat{y})$, for example the modulus of the difference $L(y, \hat{y})=\|y-\hat{y}\|$. Which is carried out in block LM, as described above.

Since the target values y are derived from intracardiac electrodes located in only one atrium, but body surface electrodes pick up signals x from both atria, a mechanism is needed to compensate for this. The idea behind atrial discriminative is training (ADT) is to ask the machine learning model to make two predictions: $fW(x)=(\hat{y}L, \hat{y}R)$, one for each atrium. However, the ground truth y from the intracardiac recording is only known for one atrium (y=yL or y=yR). The cost function therefore separates the two predictions into $L(y, \hat{y})=\alpha\ L(yL, \hat{y}L)+\beta\ L(yR, \hat{y}R)$ and the coefficients are set according to the locations of the intracardiac recordings: $(\alpha, \beta)=(1, 0)$ if y=yL and $(\alpha, \beta)=(0, 1)$ if y=yR.

As a result, at training time, the machine learning model does not know which atrium it is supposed to predict, and predictions for the atrium that was not measured intracardially are not penalized. At test time, the machine learning model will be able to make predictions for both atria simultaneously. Consequently, the foregoing systems and methods can be used to localize and quantify drivers of AF.

It will now be seen that an ADT MLM can be trained to directly predict optical flow from two different input images, which correspond to: (a) optical or other types of flow or tracking images derived from intra-cardiac EP data; and (b) optical or other types of flow or tracking images derived from body surface EP data acquired at the same time and from the same patients. Training data need not be perfect or noise free.

After having read and understood the present specification, drawings and claims, those skilled in the art will now understand that configurations and architectures of MLMs other than those explicitly described and disclosed herein can also be used obtain similarly useful results. Moreover, and with reference to FIGS. 15, 16, and 17, the ADT MLM used to provide optical or other flow or tracking predictions from body surface electrode data can be continuously or periodically updated using intra-cardiac data and/or body surface electrode data, as well as ABC patient classification data, that are or have been obtained from patients. See, is for example, Deep Learning blocks 711 and 811 in FIGS. 15 and 16. Whether located in a remote "cloud" server, a health care facility, or another type of location, machine learning training, updating, computations, and analyses can be are carried out using hardware and computer systems 300 similar those shown in FIGS. 1(a) and 1(b), or using other individual, portable, stationary, conventional, network-based, and/or cloud-based hardware and computer systems, as those skilled in the art will understand.

With respect to the foregoing atrial discriminative machine learning models, and the systems, devices, components, and methods associated therewith, the following additional embodiments, features, and aspects are also contemplated.

In one embodiment, there is provided a system configured to determine and display to a user one or more predictions or results concerning atrial fibrillation in a patient's heart, the system comprising: (a) at least one computing device; (b) at least one data acquisition device operably connected to the at least one computing device or configured to provide as outputs therefrom body surface electrogram signals; (c) a plurality of body surface electrodes configured to generate body surface electrogram signals and for placement on the patient's body surface, the plurality of body surface electrodes being operably connected to the at least one data acquisition device, and (d) a display or monitor operably connected to the at least one computing device and configured to visually display to the user the predictions or results concerning the atrial fibrillation generated by the at least one computing device; wherein the computing device comprises at least one processor and at least one non-transitory computer readable medium configured to store instructions executable by the at least one processor to determine, using a trained atrial discriminative machine learning model, the predictions or results concerning atrial fibrillation in the patient's heart, the computing device being configured to: (i) receive the body surface electrogram signals from the plurality of body surface electrodes located on the patient's body, where the body surface electrogram signals received by the at least one computing device have been at least one of conditioned, amplified, normalized, filtered, and adjusted by the data acquisition device before being provided to the computing device as conditioned electrogram signals; (ii) assign or relate positional data corresponding to positions or estimated positions of the body surface electrodes on the patient's body to their respective corresponding body surface electrogram signals and body surface electrodes; (iii) input the conditioned electrogram signals and positional data into the trained atrial discriminative machine learning model, where the trained atrial discriminative machine learning model has been trained at least partially using data obtained from a plurality of other previous patients, where intracardiac electrophysiological (EP) mapping signals for the other patients have been processed using at least one of electrographic flow (EGF), video tracking analysis, motion capture analysis, motion estimation analysis, data association and segmentation tracking analysis, particle tracking analysis, and single-particle tracking analysis methods to detect at least one of: (I) the presence of sources of atrial fibrillation in the other patients' hearts; (II) the locations of sources of atrial fibrillation in the other patients' hearts; (III) the activity levels of sources of atrial fibrillation in the other patients' hearts; (IV) the spatial variability levels of sources of atrial fibrillation in the other patients' hearts; (V) the flow angle stability levels of sources of atrial fibrillation in the other patients' hearts; and (VI) the classification of patients as at least one of types A, B and C; where paired data sets of body surface electrogram signals and the intracardiac EP mapping signals have been acquired simultaneously from at least some of the plurality of other patients and the paired data sets have been correlated to one another using the atrial discriminative trained machine model, and the trained atrial discriminative machine learning model is further configured to generate one or more of the following predictions or results for the patient using the conditioned electrogram signals and positional data corresponding to the patient: (1)

Does the patient have atrial fibrillation or not? (2) If the patient has atrial fibrillation, determining at least one of the spatial variability level, the activity level, and the flow angle stability level associated with one or more sources detected in the patient's heart; (3) If the patient has atrial fibrillation, determining the locations of one or more sources detected in the patient's heart; (4) If the patient has atrial fibrillation, whether one or more activation sources detected in the patient's heart are characterized by chaotic flow; and (5) classification of the patient as one of types A, B and C; and further wherein the computing device is configured to: (iv) process the conditioned electrogram data and positional data in the trained machine learning model to generate the one or more predictions or results; and (v) display the one or more predictions or results on the display or monitor to the user.

The foregoing embodiment can further comprise: (1) a trained atrial discriminative machine learning model configured to provide the results or predictions therefrom to a loss function module; (2) a loss function module configured to provide outputs based on the results or predictions provided by the trained atrial discriminative machine learning model back to the trained atrial discriminative machine learning model to facilitate optimizing results or predictions subsequently provided thereby; (3) predictions or results generated by an atrial discriminative machine learning model comprising one or more of: (a) the patient has no detectable atrial fibrillation at the present time; (b) the patient has a type of atrial fibrillation having a substantial probability of being treated successfully with pulmonary vein isolation alone; (c) the patient has a type of atrial fibrillation that has a substantial probability of being treated successfully only with atrial ablation or with atrial ablation in combination with pulmonary vein isolation; and (d) providing an estimate of the probability of recurrence of atrial fibrillation in the patient; (4) predictions or results generated by the atrial discriminative machine learning model comprising one or more of: (a) the estimated locations of one or more sources or rotors in the patient's heart; (b) whether one or more sources or rotors in the patient's heart are located in a right atrium or a left atrium of the patient; (c) at least one type of source or rotor in the patient's heart, including active rotors or sources, passive rotors or sources, focal points, breakthrough points, and chaotic rotors or sources; (d) activity levels of one or more sources or rotors in the patient's heart; (d) spatial variability levels of one or more sources or rotors in the patient's heart, and (e) flow angle stabilities of one or more sources or rotors in the patient's heart; (5) a trained atrial discriminative machine learning model being updated at least partially using data obtained from a plurality of new patients, where paired data sets of body surface electrogram signals and intracardiac electrophysiological (EP) mapping signals have been acquired simultaneously from each of the plurality of new patients, and the paired data sets have been correlated to one another using machine learning; (6) a trained atrial discriminative machine learning model is updated or trained at least partially using MRI data obtained from a plurality of new patients, where areas or regions of fibrosis in the plurality of new patients have been identified in the MRI data and are correlated using machine learning to one or more of the body surface electrogram signals and the EP mapping signals; (7) a trained atrial discriminative machine learning model is updated or trained at least partially using one or more of body surface electrogram data and intracardiac EP mapping signals obtained from a plurality of new patients, where a first portion of the new patients have no atrial fibrillation and are identified in the data as being atrial-fibrillation-free, and a second portion of the new patients have atrial fibrillation and are identified in the data as having atrial fibrillation, and the paired data sets have been correlated to one another using machine learning; (8) a trained atrial discriminative machine learning model being updated or trained at least partially using body surface electrogram data and intracardiac EP mapping signals obtained from a plurality of new patients determined to have atrial fibrillation prior to being treated by intra-cardiac ablation, where body surface electrogram data and intracardiac EP mapping signals are obtained from the plurality of new patients before and after atrial ablation procedures are performed in at least one atrium of each such new patient, and the resulting body surface electrogram data and intracardiac EP mapping signals have been correlated to one another using machine learning; (9) a trained atrial discriminative machine learning model being updated or trained at least partially using body surface electrogram data and intracardiac EP mapping signals obtained from a plurality of new patients determined to have had atrial fibrillation previously, who were treated with a pulmonary vein isolation procedure previously, and who have been atrial-fibrillation-free for at least one year after being treated by the pulmonary vein isolation procedure, where body surface electrogram data and intracardiac EP mapping signals have been obtained from the plurality of new patients before and one year after the pulmonary vein isolation procedures, and the resulting body surface electrogram data and intracardiac EP mapping signals have been correlated to one another using machine learning; (10) a trained atrial discriminative machine learning model being updated or trained at least partially using simulated body surface electrograms generated using a heart and torso model having one or more known origins of rotors or sources in one or more atria thereof; (11) a trained atrial discriminative machine learning model being updated or trained at least partially using data from a plurality of patients, where the data from the patients relate to one or more of atrial volume, atrial dimensions, patient age, patient weight, patient height, and patient body mass index; (12) a trained atrial discriminative machine learning model comprising one or more of: (a) a neural network, (b) a generative neural network; (c) a recurrent neural network, and (d) a feed-forward neural network; (13) a trained atrial discriminative machine learning model comprising a recurrent neural network employing long short-term memory (LSTM); (14) a trained atrial discriminative machine learning model comprising one or more of: (a) a nearest neighbor model; (b) a naive Bayes model; (c) a decision tree model; (d) a linear regression model; (e) a support vector machine (SVM) model, and (f) a neural network; (15) a trained atrial discriminative machine learning model being generated at least partially using supervised learning or unsupervised learning; (16) a trained atrial discriminative machine learning model comprising convolutional layers; (17) conditioned electrogram signals being processed by the at least one computing device to remove or substantially remove at least portions of the ORS or QRST complex from at least some of the electrogram signals; (18) Green's function being employed in the EGF or other flow or tracking methods; (19) at least one of video tracking analysis techniques, motion capture analysis techniques, motion estimation analysis techniques, data association and segmentation tracking analysis techniques, particle tracking analysis techniques, and single-particle tracking analysis techniques being employed to determine one or more of flow direction, vector fields, and vector maps; (19) EGF methods, if employed, including at least one optical flow analysis technique selected from the group consisting of a Horn-Schunck method, a Buxton-Buston method, a Black-Jepson method, a phase correlation method, a block-based method, a discrete optimization method, a Lucas-Kanade method, and a differential method of estimating optical flow.

In another embodiment, there is provided a method of determining and displaying to a user one or more predictions or results concerning atrial fibrillation in a patient's heart using a system comprising at least one computing device, at least one data acquisition device operably connected to the at least one computing device or configured to provide as outputs therefrom body surface electrogram signals, a plurality of body surface electrodes configured to generate body surface electrogram signals and for placement on the patient's body surface, the plurality of body surface electrodes being operably connected to the at least one data acquisition device, and a display or monitor operably connected to the at least one computing device and configured to visually display to the user the predictions or results concerning the atrial fibrillation generated by the at least one computing device, the computing device comprising at least one processor and at least one non-transitory computer readable medium configured to store instructions executable by the at least one processor to determine, using a trained atrial discriminative machine learning model, the predictions or results concerning atrial fibrillation in the patient's heart, the method comprising: (a) acquiring body surface electrogram signals using the body surface electrodes located on one or more body surfaces of the patient; (b) using at least one of the computing device and the data acquisition device, at least one of conditioning, filtering, normalizing and adjusting the amplitudes of the acquired body surface electrogram signals; (c) using the computing device, assigning positions or identifiers for each of the body surface electrodes to corresponding individual body surface electrogram signals; (d) using the computing device and the assigned positions or identifiers, providing or generating a 2D or 3D spatial map of the body surface electrode positions; (e) using the computing device and the trained atrial discriminative machine learning model, inputting the conditioned electrogram signals and positional data into the trained atrial discriminative machine learning model, where the trained atrial discriminative machine learning model has been trained at least partially using data obtained from a plurality of other previous patients, intracardiac electrophysiological (EP) mapping signals for the other patients have been processed using one or more of electrographic flow (EGF), video tracking analysis, motion capture analysis, motion estimation analysis, data association and segmentation tracking analysis, particle tracking analysis, and single-particle tracking analysis methods to detect at least one of the presence of sources of atrial fibrillation in the other patients' hearts, the locations of sources of atrial fibrillation in the other patients' hearts, the activity levels of sources of atrial fibrillation in the other patients' hearts, the spatial variability levels of sources of atrial fibrillation in the other patients' hearts, the flow angle stability levels of sources of atrial fibrillation in the other patients' hearts, and the classification of patients as at least one of types A, B and C, where paired data sets of body surface electrogram signals and intracardiac electrophysiological (EP) mapping signals have been acquired simultaneously from at least some of the plurality of other patients and the paired data sets have been correlated to one another using machine learning, and the trained atrial discriminative machine learning model is to generate one or more of the following predictions or results: (1) Does the patient have atrial fibrillation or not? (2) If the patient has atrial fibrillation, determining at least one of the spatial variability level, the flow angle stability level, and the activity level associated with one or more sources detected in the patient's heart; (3) If the patient has atrial fibrillation, determining the locations of one or more sources detected in the patient's heart; (4) If the patient has atrial fibrillation, whether one or more sources detected in the patient's heart are characterized by chaotic behavior; (f) processing the conditioned electrogram data and positional data in the trained machine learning model to generate the one or more predictions or results; and (g) displaying the one or more predictions or results on the display or monitor to the user.

The foregoing embodiment can further comprise: (1) a trained machine learning model having been trained at least partially using data obtained from the plurality of other previous patients, where intracardiac electrophysiological (EP) mapping signals for the other patients have been processed using one or more of electrographic flow (EGF), video tracking analysis, motion capture analysis, motion estimation analysis, data association and segmentation tracking analysis, particle tracking analysis, and single-particle tracking analysis methods to detect at least one of the presence of sources of atrial fibrillation in the other patients' hearts, the locations of sources of atrial fibrillation in the other patients' hearts, the activity levels of sources of atrial fibrillation in the other patients' hearts, the spatial variability levels of sources of atrial fibrillation in the other patients' hearts, and the flow angle stability levels of sources of atrial fibrillation in the other patients' hearts (2) generating predictions or results using the machine learning model that comprise one or more of: (a) the patient has no detectable atrial fibrillation at the present time; (b) the patient has a type of atrial fibrillation having a substantial probability of being treated successfully with pulmonary vein isolation alone; (c) the patient has a type of atrial fibrillation that has a substantial probability of being treated successfully only with atrial ablation or with atrial ablation in combination with pulmonary vein isolation; (d) providing an estimate of the probability of recurrence of atrial fibrillation in the patient; (3) generating predictions or results using the machine learning model that comprise one or more of: (a) the estimated locations of one or more sources or rotors in the patient's heart; (b) whether one or more sources or rotors in the patient's heart are located in a right atrium or a left atrium of the patient; (c) at least one type of source or rotor in the patient's heart, including active rotors or sources, passive rotors or sources, focal points, break-through points, and chaotic rotors or sources; (d) activity levels of one or more sources or rotors in the patient's heart; (e) spatial variability levels of one or more sources or rotors in the patient's heart, and (f) flow angle stability levels of one or more sources or rotors in the patient's heart; (4) updating or training the trained machine learning model at least partially using MRI data obtained from a plurality of new patients, where areas or regions of fibrosis in the plurality of new patients have been identified in the MRI data and have been correlated using machine learning to one or more of body surface electrogram signals and EP mapping signals acquired from the plurality of new patients; (5) updating or training the trained machine learning model at least partially using one or more of body surface electrogram data and intracardiac EP mapping signals obtained from a plurality of new patients, where a first portion of the new patients have no atrial fibrillation and are identified in the data as being atrial-fibrillation-free, and a second portion of the new patients have atrial fibrillation and are identified in the data as having atrial fibrillation, and the paired data sets have been correlated to one another using machine learning; (6) updating or training the trained machine learning model at least partially using MRI data obtained from at least some of the plurality of new patients, and areas or regions of atrial fibrosis have been identified in the MRI data for such new patients, and the MRI data concerning areas or regions of fibrosis have been correlated to one or more of the body surface electrogram signals and the EP mapping signals using machine learning; (7) updating or training the trained machine learning model at least partially using body surface electrogram data and intracardiac EP mapping signals obtained from a plurality of new patients determined to have atrial fibrillation prior to being treated by intra-cardiac ablation, where body surface electrogram data and intracardiac EP mapping signals are obtained from the plurality of new patients before and after atrial ablation procedures are performed in at least one atrium of each such new patient, and the resulting body surface electrogram data and intra-cardiac EP mapping signals have been correlated to one another using machine learning; (8) updating or training the trained machine learning model at least partially using body surface electrogram data and intracardiac EP mapping signals obtained from a plurality of new patients determined to have atrial fibrillation prior to being treated by intra-cardiac ablation, where body surface electrogram data and intracardiac EP mapping signals are obtained from the plurality of new patients before and after atrial ablation procedures are performed in at least one atrium of each such new patient, and the resulting body surface electrogram data and intra-cardiac EP mapping signals have been correlated to one another using machine learning; (9) updating or training the trained machine learning model at least partially using body surface electrogram data and intracardiac EP mapping signals obtained from a plurality of new patients determined to have had atrial fibrillation previously, who were treated with a pulmonary vein isolation procedure previously, and who have been atrial-fibrillation-free for at least one year after being treated by the pulmonary vein isolation procedure, where body surface electrogram data and intracardiac EP mapping signals have been obtained from the plurality of new patients before and one year after the pulmonary vein isolation procedures, and the resulting body surface electrogram data and intracardiac EP mapping signals have been correlated to one another using machine learning; (10) updating or training the trained machine learning model at least partially using simulated body surface electrograms generated using a heart and torso model having one or more known origins of rotors or sources in one or more atria thereof; (11) updating or training the trained machine learning model at least partially using data from a plurality of patients, where the data from the patients relate to one or more of atrial volume, atrial dimensions, patient age, patient weight, patient height, and patient body mass index; (12) a trained machine learning model comprising one or more of: (a) a neural network, (b) a generative neural network; (c) a recurrent neural network, and (d) a feed-forward neural network; (13) a trained machine learning model comprising a recurrent neural network employing long short-term memory (LSTM); (14) a trained machine learning model comprising one or more of: (a) a nearest neighbor model; (b) a naive Bayes model; (c) a decision tree model; (d) a linear regression model; (e) a support vector machine (SVM) model, and (f) a neural network; (15) at least partially generating the trained machine learning model using supervised or unsupervised learning; (16) a trained machine learning model comprising convolutional layers; (17) removing or substantially removing at least portions of the QRS or QRST complex from at least some of the conditioned electrogram signals; (18) processing the EP mapping signals for at least some of the other patients using electrographic flow (EGF) methods to detect at least one of the presence of sources of atrial fibrillation in the other patients' hearts, the locations of sources of atrial fibrillation in the other patients' hearts, the activity levels of sources of atrial fibrillation in the other patients' hearts, the steadiness levels of sources of atrial fibrillation in the other patients' hearts, the flow angle stability levels of sources of atrial fibrillation in the other patients' hearts, and a classification of the other patients as A-type patients, B-type patients, or C-type patients, at least one of which sources, source locations, source activity levels. source steadiness levels, flow angle stability levels, and patient classifications have then been correlated with their corresponding body surface electrogram signals in the trained machine learning model; (19) employing Green's function in processing the EP mapping signals; (20) employing one or more of video tracking analysis, motion capture analysis, motion estimation analysis, data association and segmentation tracking analysis, particle tracking analysis, and single-particle tracking analysis methods to estimate flow or direction, or to generate vector or other maps; (20) EGF methods including at least one optical flow analysis technique selected from the group consisting of a Horn-Schunck method, a Buxton-Buston method, a Black-Jepson method, a phase correlation method, a block-based method, a discrete optimization method, a Lucas-Kanade method, and a differential method of estimating optical flow.

In yet other embodiments utilizing EGF techniques, there are provided systems, devices, components, and methods for detecting the locations of epileptogenic and seizure onset zones in a patient's brain. These can include diagnosing and treating epilepsy in a patient using electroencephalographic (EEG) mapping techniques in conjunction with EGF techniques, as well as in some embodiments using imaging, navigation, electrical stimulation and other types of medical systems, devices, components, and methods. Such embodiments relate to systems, devices, components and methods for discovering with enhanced precision the location(s) of the source(s) of epileptic seizure onset zones (SOZs), and other types of epileptogenic zones, in a patient's brain.

In some embodiments configured to detect the source(s) of epileptic seizure onset zones (SOZs), and other types of epileptogenic zones, in a patient's brain, there are provided at least one computing device comprising at least one non-transitory computer readable medium configured to store instructions executable by at least one processor to determine the location of the at least one epileptogenic zone in the patient's brain, the computing device being configured to: (a) receive a plurality of electroencephalogram (EEG) signals representative of the electrical activity of the patient's brain; (b) normalize or adjust amplitudes of the EEG signals; (c) assign predetermined positions of electrodes employed to acquire the EEG signals; (c) provide or generate a two-dimensional (2D) or three-dimensional (3D) spatial map of the electrode positions; (d) for each or selected discrete times over which the EEG signals are being processed, process the amplitude-adjusted EEG signals to generate a plurality of three-dimensional EEG surfaces corresponding at least partially to the 2D or 3D map, one surface being generated for each such time, and (e) process the plurality of three-dimensional EEG surfaces through time to generate a velocity vector or other type of flow or flow direction or magnitude map corresponding at least partially to the 2D or 3D map, the velocity vector or other type of flow or flow direction or magnitude map being configured to reveal the location of the at least one epileptogenic zone within the patient's brain using EGF techniques.

These embodiments aimed at diagnosing epilepsy can also include one or more of non-invasive electrodes configured to be located on the exterior of a patient's skull; invasive electrodes configured to be implanted within the patient's brain; at least portions of the generated EEG surfaces generated by the computing device being configured to correspond to estimated wave shapes or wavefronts; EEG surfaces generated by the computing device using Green's function; EEG surfaces generated by the computing device using a two-dimensional or three-dimensional biharmonic spline interpolation function; vector maps generated by the computing device comprising arrows or colors representative of directions of electrical potential propagation; vector maps generated by the computing device comprising arrows or colors having attributes representative of velocities of electrical potential propagation; vector maps generated by the computing device being configured to reveal the at least one epileptogenic zone as one or more of a symptomatogenic zone, an irritative zone, a seizure-onset zone, a structurally abnormal zone, and a functional deficit zone in the patient's brain; vector maps generated by the computing device being configured to reveal a location of an epileptic focal point in the patient's brain; vector maps generated by the computing device being configured to reveal a location of an epileptogenic lesion in the patient's brain; vector maps being generated by the computing device using at least one of an optical flow analysis technique, a video tracking analysis technique, a motion capture analysis technique, a motion estimation analysis technique, a data association and segmentation tracking analysis technique, a particle tracking analysis technique, and a single-particle tracking analysis technique; the at least one optical flow analysis technique, if employed, is selected from the group consisting of a Horn-Schunck method, a Buxton-Buston method, a Black-Jepson method, a phase correlation method, a block-based method, a discrete optimization method, a Lucas-Kanade method, and a differential method of estimating optical flow; the plurality of EEG signals are processed by the computing device to generate an averaged EEG signal, and the averaged EEG signal is subtracted from each of the individual EEG signals to generate artifact- or far-field adjusted individual EEG signals; the artifact-adjusted individual EEG signals are processed by the computing device with a high-pass filter to remove DC offsets; the high-pass filter applied by the computing device removes frequencies below between about 5 Hz and about 20 Hz; interpolated or estimated values are generated by the computing device for positions in between the measured or calculated grid values corresponding to one or more of the EEG signals, the plurality of smoothed EEG surfaces, and the vector map; a representative amplitude value is generated by the computing device for each individual EEG signal, and the representative amplitude value generated for each EEG signal is stored for later use in image backgrounds that show low signal amplitude areas of the 2D representation, the low signal amplitude areas being indicative of one or more of low electrical activity areas or regions of the patient's brain, poor electrode contact, and areas of the patient's brain that have sustained trauma, injury or neural damage; electrode positions in the 2D representation are modified by the computing device based upon navigational or positional data corresponding to measured or sensed actual electrode positions; the navigational data are provided to the computing device by a medical navigation system, a computed tomography scanner, a magnetic resonance image scanner, or an X-ray fluoroscopy system;

In view of the structural and functional descriptions provided herein, those skilled in the art will appreciate that portions of the described devices and methods may be configured as methods, data processing systems, or computer methods. Accordingly, these portions of the devices and methods described herein may take the form of a hardware embodiment, a software embodiment, or an embodiment combining software and hardware, such as shown and described with respect to computer system 300 illustrated in FIG. 1(*b*). Furthermore, portions of the devices and methods described herein may be a computer method stored in a computer-usable storage medium having computer readable program code on the medium. Any suitable computer-readable medium may be utilized including, but not limited to, static and dynamic storage devices, hard disks, optical storage devices, and magnetic storage devices.

Certain embodiments of portions of the devices and methods described herein are also described with reference to block diagrams of methods, systems, and computer methods. It will be understood that such block diagrams, and combinations of blocks diagrams in the Figures, can be implemented using computer-executable instructions. These computer-executable instructions may be provided to one or more processors of a general purpose computer, a special purpose computer, or any other suitable programmable data processing apparatus (or a combination of devices and circuits) to produce a machine, such that the instructions, which executed via the processor(s), implement the functions specified in the block or blocks of the block diagrams.

These computer-executable instructions may also be stored in a computer-readable memory that can direct computer 300 or other programmable data processing apparatus to function in a particular manner, such that the instructions stored in the computer-readable memory result in an article of manufacture including instructions which implement the function specified in an individual block, plurality of blocks, or block diagram. The computer program instructions may also be loaded onto computer 300 or other programmable data processing apparatus to cause a series of operational steps to be performed on the computer or other programmable apparatus to produce a computer implemented process such that the instructions which execute on computer 300 or other programmable apparatus provide steps for implementing the functions specified in the an individual block, plurality of blocks, or block diagram.

In this regard, FIG. 1(*b*) illustrates only one example of a computer system 300 (which, by way of example, can include multiple computers or computer workstations) that can be employed to execute one or more embodiments of the devices and methods described and disclosed herein, such as devices and methods configured to acquire and process sensor or electrode data, to process image data, and/or transform sensor or electrode data and image data associated with the analysis of cardiac electrical activity and the carrying out of the combined electrophysiological mapping and analysis of the patient's heart 10 and ablation therapy delivered thereto.

Additionally, any one or more of the visualization systems, devices, components, and methods disclosed and described in the '588 patent (U.S. patent application Ser. No. 16/918,588 entitled "Methods, Systems, Devices, and Components for Visualizing Electrographic Flow (EGF)" to Haeusser et al. filed on Dec. 21, 2019) may be readily adapted for use in conjunction with the various non-optical-flow (e.g., tracking and other flow) data processing embodiments disclosed and described herein, as those skilled in the art will understand after having read and understood the present specification, drawings, and claims.

It will now be seen that the various systems, devices, components and methods disclosed and described herein are capable of detecting with considerable accuracy and precision the locations of sources of cardiac rhythm disorders in a patient's heart.

What have been described above are examples and embodiments of the devices and methods described and disclosed herein. It is, of course, not possible to describe every conceivable combination of components or methodologies for purposes of describing the invention, but one of ordinary skill in the art will recognize that many further combinations and permutations of the devices and methods described and disclosed herein are possible. Accordingly, the devices and methods described and disclosed herein are intended to embrace all such alterations, modifications and variations that fall within the scope of the appended claims. In the claims, unless otherwise indicated, the article "a" is to refer to "one or more than one."

The foregoing outlines features of several embodiments so that those skilled in the art may better understand the detailed description set forth herein. Those skilled in the art will now understand that many different permutations, combinations and variations of hearing aid 10 fall within the scope of the various embodiments. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

After having read and understood the present specification, those skilled in the art will now understand and appreciate that the various embodiments described herein provide solutions to long-standing problems, both in the use of electrophysiological mapping systems and in the use of cardiac ablation systems.

We claim:

1. A system configured to detect at least one location of at least one source of at least one cardiac rhythm disorder in a patient's heart, the system comprising:
   (a) at least one computing device;
   (b) at least one data acquisition device operably connected to the at least one computing device or configured to provide as outputs therefrom at least one of intracardiac electrophysiological EP mapping signals (EP mapping signals) and body surface electrogram signals;
   (c) a display or monitor operably connected to the at least one computing device and configured to visually display to the user one or more maps generated by the at least one computing device;
   wherein the computing device comprises at least one non-transitory computer readable medium configured to store instructions executable by at least one processor to determine the at least one location of the at least one source of the at least one cardiac rhythm disorder in the patient's heart, the computing device being configured to: (i) receive at least one of the intracardiac EP mapping signals and the body surface electrogram signals from at least one of a plurality of intracardiac electrodes located inside the patient's heart and a plurality of body surface electrodes located on the patient's body, where amplitudes of at least one of the intracardiac EP mapping signals and the body surface electrogram signals received by the at least one computing device have been at least one of conditioned, amplified, normalized, filtered, and adjusted by the data acquisition device before being provided to the computing device; (ii) assign or relate positional data corresponding to predetermined positions of at least one of the intracardiac electrodes in the patient's heart and the body surface electrodes on the patient's body to their respective corresponding: (1) intracardiac EP mapping signals and intracardiac electrodes, and (2) body surface electrogram signals and body surface electrodes; (iii) generate at least one spatial map of at least one of the intracardiac electrode positions and the body surface electrode positions; (iv) for each or selected discrete times over which at least one of the intracardiac EP mapping signals and the body surface electrogram signals are being processed, process at least one of the amplitude-adjusted intracardiac EP mapping signals and the amplitude-adjusted body surface electrogram signals to generate a plurality of electrogram surfaces or data grids, each such surface or data grid corresponding at least partially to the at least one spatial map, at least one surface or data grid being generated for each such time, and (v) using at least one of electrographic flow (EGF), video tracking analysis, motion capture analysis, motion estimation analysis, data association and segmentation tracking analysis, particle tracking analysis, and single-particle tracking analysis methods to process the plurality of electrogram surfaces or data grids through time to generate at least one map corresponding at least partially to the spatial map, the at least one map being configured to reveal the at least one location of the at least one source of the at least one cardiac rhythm disorder, the at least one map being shown to the user on the display or monitor.

2. The system of claim 1, wherein a trained atrial discriminative machine learning model has been trained at least partially using data obtained from a plurality of other previous patients, where intracardiac electrophysiological (EP) mapping signals for the other patients have been processed using one or more of electrographic flow (EGF), video tracking analysis, motion capture analysis, motion estimation analysis, data association and segmentation tracking analysis, particle tracking analysis, and single-particle tracking analysis methods to detect at least one of: (I) the presence of sources of atrial fibrillation in the other patients' hearts; (II) the locations of sources of atrial fibrillation in the other patients' hearts; (III) the activity levels of sources of atrial fibrillation in the other patients' hearts; (IV) the spatial variability levels of sources of atrial fibrillation in the other patients' hearts; (V) the flow angle stability levels of sources of atrial fibrillation in the other patients' hearts; and (VI) the classification of patients as at least one of types A, B and C.

3. The system of claim 2, wherein paired data sets of body surface electrogram signals and the intracardiac EP mapping signals have been acquired simultaneously from at least some of the plurality of other patients and the paired data sets have been correlated to one another using the trained atrial discriminative machine learning model.

4. The system of claim 3, wherein the trained atrial discriminative machine learning model is further configured to generate one or more of the following predictions or results for the patient using the conditioned electrogram signals and positional data corresponding to the patient: (1) Does the patient have atrial fibrillation or not? (2) If the patient has atrial fibrillation, determining at least one of the spatial variability level, the activity level, and the flow angle stability level associated with one or more sources detected in the patient's heart; (3) If the patient has atrial fibrillation, determining the locations of one or more sources detected in the patient's heart; (4) If the patient has atrial fibrillation, whether one or more activation sources detected in the patient's heart are characterized by chaotic flow; and (5) classification of the patient as one of types A, B and C.

5. The system of claim 4, wherein the computing device is further configured to: (iv) process the conditioned electrogram data and positional data in the trained machine learning model to generate the one or more predictions or results; and (v) display the one or more predictions or results on the display or monitor to the user.

6. The system of claim 1, wherein the plurality of electrogram surfaces is a plurality of three-dimensional electrogram surfaces that includes a first three-dimensional electrogram surface corresponding to a first EP mapping signal recording of a first duration of time and a second three-dimensional electrogram surface corresponding to a second EP mapping signal recording of a second duration of time, the second duration of time being greater than the first duration of time.

7. The system of claim 6, wherein the first and second three-dimensional electrogram surfaces facilitate a determination of whether the patient's AF revealed in the map is characterized by one or more of: (a) atrial behavior exhibiting spatially and temporally stable rotors, drivers or sources (Type A): (b) atrial behavior where spatially stable rotors switch on and off (Type B), and (c) chaotic atrial behavior in which the rotors are spatially and temporally variable (Type C).

8. The system of claim 1, wherein at least one of an activity value, a flow angle stability value, and a steadiness value are generated by the computing device for one or more sources corresponding to the at least one cardiac rhythm disorder revealed in the map.

9. The system of claim 8, wherein at least one of the activity value, the flow angle stability value, and the steadiness value are displayed on the display or monitor.

10. The system of claim 8, wherein on the basis of at least one of the generated activity values, flow angle stability values, and steadiness values the computing device determines whether to classify the patient as an A-type patient, a B-type patient, or a C-type patient.

11. The system of claim 8, wherein the computing device is configured to determine whether the at least one map corresponds to an A-type patient, a B-type patient, or a C-type patient.

12. The system of claim 1, wherein the electrogram surfaces or data grids comprise at least one three-dimensional surface.

13. The system of claim 1, wherein the electrogram surfaces or data grids are generated by the computing device using Green's function.

14. The system of claim 1, wherein the vector map generated by the computing device is configured to reveal a location in the patient's heart of one or more of: (a) an active rotor; (b) a passive rotor; (c) a breakthrough point, and (d) a focal point.

15. The system of claim 1, wherein the EGF method is selected from the group consisting of a Horn-Schunck method, a Buxton-Buston method, a Black-Jepson method, a phase correlation method, a block-based method, a discrete optimization method, a Lucas-Kanade method, and a differential method of estimating optical flow.

16. A method of detecting at least one location of at least one source of at least one cardiac rhythm disorder in a patient's heart using a system comprising at least one computing device, the computing device comprising at least one non-transitory computer readable medium configured to store instructions executable by at least one processor to determine the at least one location of the at least one source of the at least one cardiac rhythm disorder in the patient's heart, the system further comprising at least one of a plurality intracardiac electrodes and a plurality of body surface electrodes operably connected to the computing device through a data acquisition device and a monitor or screen operably connected to the computing device, the method comprising:
(a) acquiring, using the data acquisition device, at least one of intracardiac electrophysiological mapping signals (EP mapping signals) and body surface electrogram signals using at least one of the intracardiac electrodes located within the patient's heart and the body surface electrodes located on one or more body surfaces of the patient;
(b) using at least one of the computing device and the data acquisition device, at least one of conditioning, filtering, normalizing and adjusting the amplitudes of at least one of the acquired EP mapping signals and the body surface electrogram signals;
(c) using the computing device, assigning positions or identifiers for each of at least one of the intracardiac electrodes and the body surface electrodes to corresponding to at least one of individual EP mapping signals and individual body surface electrogram signals;
(d) using the computing device and the assigned positions or identifiers, providing or generating a spatial map of at least one of the intracardiac electrode positions and the body surface electrode positions;
(e) using the computing device, for each or selected discrete times over which at least one of the EP mapping signals and the body surface electrogram signals are being processed, processing at least one of the amplitude-adjusted EP mapping signals and the amplitude-adjusted body surface electrogram signals to generate a plurality of electrogram surfaces or data grids corresponding at least partially to the spatial map, one surface or data grid being generated for each such time, and
(f) using the computing device, and using at least one of electrographic flow (EGF), video tracking analysis, motion capture analysis, motion estimation analysis, data association and segmentation tracking analysis, particle tracking analysis, and single-particle tracking analysis methods, processing the plurality of electrogram surfaces or data grids through time to generate a map corresponding at least partially to the spatial map, the map being configured to reveal on the monitor or display to a user the at least one location of the at least one source of the at least one cardiac rhythm disorder.

17. The method of claim 16, further comprising generating the electrogram surfaces or data grids using Green's function.

18. The method of claim 16, further comprising showing the at least one cardiac rhythm disorder as an active rotor, a passive rotor, a breakthrough point, or a focal point on the vector map.

19. The method of claim 16, wherein the EGF method is selected from the group consisting of a Horn-Schunck method, a Buxton-Buston method, a Black-Jepson method, a phase correlation method, a block-based method, a discrete optimization method, a Lucas-Kanade method, and a differential method of estimating optical flow.

20. The method of claim 19, wherein a trained atrial discriminative machine learning model has been trained at least partially using data obtained from a plurality of other previous patients, where intracardiac electrophysiological (EP) mapping signals for the other patients have been processed using at least of electrographic flow (EGF), video tracking analysis, motion capture analysis, motion estimation analysis, data association and segmentation tracking analysis, particle tracking analysis, and single-particle tracking analysis methods to detect at least one of: (I) the presence of sources of atrial fibrillation in the other patients' hearts; (II) the locations of sources of atrial fibrillation in the other patients' hearts; (III) the activity levels of sources of atrial fibrillation in the other patients' hearts; (IV) the spatial variability levels of sources of atrial fibrillation in the other patients' hearts; (V) the flow angle stability levels of sources of atrial fibrillation in the other patients' hearts; and (VI) the classification of patients as at least one of types A, B and C.

21. The method of claim 20, wherein paired data sets of body surface electrogram signals and the intracardiac EP mapping signals have been acquired simultaneously from at least some of the plurality of other patients and the paired data sets have been correlated to one another using the trained atrial discriminative machine model.

22. The method of claim 21, further comprising, using the trained atrial discriminative machine learning model, generating one or more of the following predictions or results for the patient using the conditioned electrogram signals and positional data corresponding to the patient: (1) Does the patient have atrial fibrillation or not? (2) If the patient has atrial fibrillation, determining at least one of the spatial variability level, the activity level, and the flow angle stability level associated with one or more sources detected in the patients heart; (3) If the patient has atrial fibrillation, determining the locations of one or more sources detected in the patients heart; (4) If the patient has atrial fibrillation, whether one or more activation sources detected in the patients heart are characterized by chaotic flow; and (5) classification of the patient as one of types A, B and C.

* * * * *